(12) United States Patent
Santa Maria et al.

(10) Patent No.: US 11,998,615 B2
(45) Date of Patent: Jun. 4, 2024

(54) FUNCTIONALIZED NANOPARTICLES AND THEIR USE IN TREATING BACTERIAL INFECTIONS

(71) Applicant: The Board of Trustees of the Leland Stanford Junior University, Stanford, CA (US)

(72) Inventors: Peter Luke Santa Maria, Redwood City, CA (US); Laurent Bekale, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/719,727

(22) Filed: Apr. 13, 2022

(65) Prior Publication Data

US 2022/0339293 A1    Oct. 27, 2022

Related U.S. Application Data

(60) Provisional application No. 63/174,964, filed on Apr. 14, 2021.

(51) Int. Cl.
*A61K 47/69*  (2017.01)
*A61K 47/60*  (2017.01)
*A61P 31/04*  (2006.01)

(52) U.S. Cl.
CPC .......... *A61K 47/6929* (2017.08); *A61K 47/60* (2017.08); *A61P 31/04* (2018.01)

(58) Field of Classification Search
CPC ............................ A61K 47/6929; A61P 31/00
See application file for complete search history.

(56) References Cited

U.S. PATENT DOCUMENTS

| | | |
|---|---|---|
| 2006/0148104 A1 | 7/2006 | Marini et al. |
| 2010/0298536 A1 | 11/2010 | Park et al. |
| 2016/0046936 A1 | 2/2016 | Li et al. |
| 2018/0078510 A1 | 3/2018 | Alonso Fernandez et al. |
| 2018/0326050 A1 | 11/2018 | Blander et al. |

FOREIGN PATENT DOCUMENTS

| | | |
|---|---|---|
| WO | 2019076125 A1 | 4/2019 |
| WO | 2021011398 A1 | 1/2021 |

OTHER PUBLICATIONS

Pradeepa, S.M. Vidya, et al. "Preparation of gold nanoparticles by novel bacterial exopolysaccharide for antibiotic delivery." Life Sciences. (2016), vol. 153, pp. 171-179. (Year: 2016).*
European Pharmaceutical Review. "The central role of excipients in drug formulation." (Apr. 18, 2013). Accessed Sep. 13, 2023. Available from: < https://www.europeanpharmaceuticalreview.com/article/18434/the-central-role-of-excipients-in-drug-formulation-2/ > . (Year: 2013).*
"Dosage Forms/Routes of Administration." (Oct. 14, 2010). Accessed Jul. 5, 2018. Accessed from: < https://www.pharmacy-tech-study.com/dosage-forms.html > . (Year: 2010).*
Khatoon, Zohra, et al. "Bacterial biofilm formation on implantable devices and approaches to its treatment and prevention." Heliyon. 4 (2018), (Year: 2018).*
Liu et al. (2019) Nanotechnology-based antimicrobials and delivery systems for biofilm-infection control. Chemical Society Reviews 48:428-446.
Teirlinck et al. (2018) Laser-induced vapour nanobubbles improve drug diffusion and efficiency in bacterial biofilms. Nature Communications 9:1-12.
Kumar et al. (2018) Insights into cell penetrating peptide conjugated gold nanoparticles for internalization into bacterial cells. Biophys. Chem. 237:38-46.
Santos et al. (2018) Nanomaterials and molecular transporters to overcome the bacterial envelope barrier: Towards advanced delivery of antibiotics. Adv. Drug Deliv. Rev. 136-137:28-48.
Pelgrift et al. (2013) Nanotechnology as a therapeutic tool to combat microbial resistance. Adv. Drug Deliv. Rev. 65(13-14):1803-1815.
Abenojar et al. (2018) Magnetic Glycol Chitin-Based Hydrogel Nanocomposite for Combined Thermal and D-Amino-Acid-Assisted Biofilm Disruption. ACS Infect Dis. 4(8):1246-1256.
Wei et al. (2015) Near infrared-caged D-amino acids multifunctional assembly for simultaneously eradicating biofilms and bacteria. Chem Commun (Camb) 51(63):12677-12679.
Smekalova et al. (2016) Enhanced antibacterial effect of antibiotics in combination with silver nanoparticles against animal pathogens. Vet J. 209:174-179.
Pusic et al. (2016) Cross-regulation by CrcZ RNA controls anoxic biofilm formation in Pseudomonas aeruginosa. Sci Rep. 6:39621.
Pusic et al. (2018) Harnessing Metabolic Regulation to Increase Hfq-Dependent Antibiotic Susceptibility in Pseudomonas aeruginosa. Front Microbiol. Nov. 9, 2018;9:2709.

(Continued)

*Primary Examiner* — John S Kenyon
(74) *Attorney, Agent, or Firm* — Jenny L. Buchbinder; Bozicevic, Field & Francis LLP

(57) ABSTRACT

Compositions, methods, and kits are provided for treating bacterial infections with nanoparticles comprising a thiol-binding metallic core conjugated to a fluoroquinolone antibiotic. Recalcitrant infections are often difficult to treat because of the presence of persister cells, a subpopulation of bacterial cells that is highly tolerant of traditional antibiotics. Persister cells are dormant, which makes them less susceptible to many antibiotics, which are designed to kill growing cells. Administration of nanoparticles comprising a thiol-binding metallic core conjugated to fluoroquinolone antibiotics was found to be highly efficacious in eradicating persister cells and for treating infections for a broad range of bacterial species, including Gram-positive and Gram-negative bacteria. Such treatment was effective not only in eradicating planktonic bacteria but also bacteria in biofilms.

23 Claims, 20 Drawing Sheets

Specification includes a Sequence Listing.

(56) References Cited

OTHER PUBLICATIONS

Jayawardana et al. (2015) Aggregation-based detection of *M. smegmatis* using D-arabinose-functionalized fluorescent silica nanoparticles. Chem. Commun. (Camb). 51(88):15964-6.
Walkenhorst et al. (2016) Using adjuvants and environmental factors to modulate the activity of antimicrobial peptides. Biochim Biophys Acta. 1858(5):926-35.
Yan et al. (2018) The Pathways for Layered Double Hydroxide Nanoparticles to Enhance Antigen (Cross)-Presentation on Immune Cells as Adjuvants for Protein Vaccines. Front. Pharmacol. 9:1060.
Varela-Aramburu et al. (2020) Targeting and Inhibiting Plasmodium falciparum Using Ultra-small Gold Nanoparticles. ACS Appl Mater Interfaces 12(39):43380-43387.
Tom et al. (2004) Ciprofloxacin-protected gold nanoparticles. Langmuir 20(5):1909-1914.
Weber et al. (2014) Effect of gold nanoparticles and ciprofloxacin on microbial catabolism: a community-based approach. Environ. Toxicol. Chem. 33(1):44-51.
Nisar et al. (2016) Robust Synthesis of Ciprofloxacin-Capped Metallic Nanoparticles and Their Urease Inhibitory Assay. Molecules 21(4):411.

\* cited by examiner

SEQUENCE LISTING

```
<160> NUMBER OF SEQ ID NOS: 15

<210> SEQ ID NO 1
<211> LENGTH: 407
<212> TYPE: DNA
<213> ORGANISM: Pseudomonas aeruginosa

<400> SEQUENCE: 1
gcacaacaac aataacaagc aacgacgaag acaataaaaa caacacgtaa cgactccagc    60
acaacaaaaa caaaatcgcg gaggcgcagc taactgattc ttttggagag gagttgctgt   120
cgggacccgt cccgcagcca gtcggaagaa gaataaaaact gccttgaggc agcgcacaga   180
ctggttggat cgctcgacga tcatggcagc atcagcgacc aaagcaatcc gtttgctatt   240
gaactcccag cctgggagat atccctgaag cgactggctc aagggacggg tcgacaaaca   300
aaaacaacaa gcccgaaatc ataataaaaa caaagcacgc acctacttgg gggggagctt   360
cggctccccc agtagcttca cccctccct ccgttttccc cgttttt                  407

<210> SEQ ID NO 2
<211> LENGTH: 16
<212> TYPE: DNA
<213> ORGANISM: Pseudomonas aeruginosa

<400> SEQUENCE: 2
acaacaacaa taacaa                                                   16

<210> SEQ ID NO 3
<211> LENGTH: 11
```

```
<212> TYPE: DNA
<213> ORGANISM: Pseudomonas aeruginosa

<400> SEQUENCE: 3
aacaagaaca a                                                           11

<210> SEQ ID NO 4
<211> LENGTH: 12
<212> TYPE: DNA
<213> ORGANISM: Pseudomonas aeruginosa

<400> SEQUENCE: 4
agaacaacaa aa                                                          12

<210> SEQ ID NO 5
<211> LENGTH: 13
<212> TYPE: DNA
<213> ORGANISM: Pseudomonas aeruginosa

<400> SEQUENCE: 5
acaacaagaa caa                                                         13

<210> SEQ ID NO 6
<211> LENGTH: 13
<212> TYPE: DNA
<213> ORGANISM: Pseudomonas aeruginosa

<400> SEQUENCE: 6
agaacaagaa caa                                                         13

<210> SEQ ID NO 7
<211> LENGTH: 11
<212> TYPE: PRT
<213> ORGANISM: Artificial Sequence
<220> FEATURE:
<223> OTHER INFORMATION: TAT cell-penetrating peptide

<400> SEQUENCE: 7

Tyr Gly Arg Lys Lys Arg Arg Gln Arg Arg Arg
1               5                   10

<210> SEQ ID NO 8
<211> LENGTH: 18
<212> TYPE: DNA
<213> ORGANISM: Artificial Sequence
<220> FEATURE:
<223> OTHER INFORMATION: ahpB forward primer
<220> FEATURE:
<221> NAME/KEY: source
<222> LOCATION: (1)..(18)
<223> OTHER INFORMATION: sequence is synthesized

<400> SEQUENCE: 8
ccttgcgtgc ttcgttcc                                                    18

<210> SEQ ID NO 9
<211> LENGTH: 19
<212> TYPE: PRT
<213> ORGANISM: Artificial Sequence
<220> FEATURE:
<223> OTHER INFORMATION: ahpB reverse primer
<220> FEATURE:
<221> NAME/KEY: SIGNAL
<222> LOCATION: (1)..(19)
<223> OTHER INFORMATION: sequence is synthesized

<400> SEQUENCE: 9
```

Ala Gly Ala Cys Cys Thr Cys Gly Cys Gly Thr Gly Thr Thr Cys
1               5                   10                  15

Cys Thr Cys

<210> SEQ ID NO 10
<211> LENGTH: 19
<212> TYPE: DNA
<213> ORGANISM: Artificial Sequence
<220> FEATURE:
<223> OTHER INFORMATION: ahpCF forward primer
<220> FEATURE:
<221> NAME/KEY: source
<222> LOCATION: (1)..(19)
<223> OTHER INFORMATION: sequence is synthesized

<400> SEQUENCE: 10
gcaagtggtc ggtcctgat                                            19

<210> SEQ ID NO 11
<211> LENGTH: 19
<212> TYPE: DNA
<213> ORGANISM: Artificial Sequence
<220> FEATURE:
<223> OTHER INFORMATION: ahpCF reverse primer
<220> FEATURE:
<221> NAME/KEY: source
<222> LOCATION: (1)..(19)
<223> OTHER INFORMATION: sequence is synthesized

<400> SEQUENCE: 11
agaagtgggt gtcggtggt                                            19

<210> SEQ ID NO 12
<211> LENGTH: 20
<212> TYPE: DNA
<213> ORGANISM: Artificial Sequence
<220> FEATURE:
<223> OTHER INFORMATION: katA forward primer
<220> FEATURE:
<221> NAME/KEY: source
<222> LOCATION: (1)..(20)
<223> OTHER INFORMATION: sequence is synthesized

<400> SEQUENCE: 12
gcggctacct atcgctacaa                                           20

<210> SEQ ID NO 13
<211> LENGTH: 19
<212> TYPE: DNA
<213> ORGANISM: Artificial Sequence
<220> FEATURE:
<223> OTHER INFORMATION: katA reverse primer
<220> FEATURE:
<221> NAME/KEY: source
<222> LOCATION: (1)..(19)
<223> OTHER INFORMATION: sequence is synthesized

<400> SEQUENCE: 13
tccggcgaga aaccgatac                                            19

<210> SEQ ID NO 14
<211> LENGTH: 20
<212> TYPE: DNA
<213> ORGANISM: Artificial Sequence
<220> FEATURE:
<223> OTHER INFORMATION: katB forward primer
<220> FEATURE:
<221> NAME/KEY: source

```
<222> LOCATION: (1)..(20)
<223> OTHER INFORMATION: sequence is synthesized

<400> SEQUENCE: 14
gaaacaggtg gctgaagtcc                                              20

<210> SEQ ID NO 15
<211> LENGTH: 19
<212> TYPE: DNA
<213> ORGANISM: Artificial Sequence
<220> FEATURE:
<223> OTHER INFORMATION: katB reverse primer
<220> FEATURE:
<221> NAME/KEY: source
<222> LOCATION: (1)..(19)
<223> OTHER INFORMATION: sequence is synthesized

<400> SEQUENCE: 15
cgacctgttc ggtttcctg                                               19
```

FUNCTIONALIZED NANOPARTICLES AND THEIR USE IN TREATING BACTERIAL INFECTIONS

CROSS-REFERENCE TO RELATED APPLICATION

This application claims benefit under 35 U.S.C. § 119(e) of provisional application 63/174,964, filed Apr. 14, 2021, which application is hereby incorporated by reference in its entirety.

STATEMENT REGARDING FEDERALLY SPONSORED RESEARCH OR DEVELOPMENT

This invention was made with Government support under contract AI154097 awarded by the National Institutes of Health. The Government has certain rights in the invention.

BACKGROUND

Antibiotics are the mainstay of modern clinical medicine. However, bacteria develop resistance to both natural and synthetic antibiotics within years of their first clinical use (Walsh (2003) Nature Reviews Microbiology 1:65-70). Current mechanisms of antibiotic resistance include: decreased uptake by changes in outer membrane permeability; antibiotic excretion by activation of efflux pump-proteins; enzymatic modification of the antibiotic; modification of antibiotic targets; and bacterial physiology such as biofilm (van Hoek et al. (2011) Front. Microbiol. 2:203).

In the United States and Europe alone, over 50,000 people die every year because of resistant infections (The Review on Antimicrobial Resistance. Antimicrobial Resistance: Tackling a crisis for the health and wealth of nations (2014), amr-review.org/Publications.html)). Lengths of stays in a hospital are prolonged by antibiotic-resistant infections, and these same infections are often acquired in hospitals. The economic impact of antibiotic resistant infections is estimated to be between US $5 billion and US $24 billion per year in the United States alone (Hall (2004) Nature Reviews Microbiology 2:430-435). However, the drug pipelines of pharmaceutical companies have not kept pace with the evolution of antibiotic resistance. In 2004, only 1.5% of all the drugs in development by the world's 15 largest pharmaceutical companies were antibiotics (Smith and Coast, "The economic burden of antimicrobial resistance: why it is more serious than current studies suggest." (2012), researchgate.net/publication/291413454). The new reality that we must face is that the pharmaceutical companies are not presently aligned for the discovery of new antibiotics. A strategy to protect our existing antibiotics is through the use of antibiotic adjuvants, compounds that enhance the activity of current drugs and minimize, and even directly block resistance (Lu et al. (2009) Proc. Natl. Acad. Sci. U.S.A. 106(12):4629-4634, Gonzalez-Bello (2017) Bioorg. Med. Chem. Lett. 27(18):4221-4228). Another strategy is the used of ant-virulence agents. These agents can circumvent antibiotic resistance by disarming pathogens of virulence factors that facilitate human disease while leaving bacterial growth pathways (Dickey et al. (2017) Nat. Rev. Drug Discov. 16(7):457-471).

Bacterial cells, attached to a surface, can aggregate to each other to form biofilms. Bacteria growing biofilms may exhibit increased tolerance to antimicrobial agents, it is very difficult or eliminate substantially reduce. Biofilm bacteria have two dormant phenotypes: the viable but non-culturable (VBNC) state and the persister state. Dormant phenotypes (VBNC and persisters) allow bacteria to survive in conditions that are deadly to the rest of their genetically identical lineage. Once in biofilms, they can escape the immune system. Thus, one of the main roles of biofilm is to provide a protective habitat for persisters and VBNC by shielding them from the immune system (Lewis (2010) Microbe (Washington, D.C.) 5(10):429-437). Another property of biofilms is their capacity to be more resistant to antimicrobial agents than planktonic cells (Spoering et al. (2001) J. Bacteriol. 183(23):6746-6751). Thus, there is an ongoing and unmet need for an improved approach to treating antibiotic resistant infections.

SUMMARY

Compositions, methods, and kits are provided for treating bacterial infections with nanoparticles comprising a thiol-binding metallic core conjugated to a fluoroquinolone antibiotic. Recalcitrant infections are often difficult to treat because of the presence of persister cells, a subpopulation of bacterial cells that is highly tolerant of traditional antibiotics. Persister cells are dormant, which makes them less susceptible to many antibiotics, which are designed to kill growing cells. Administration of nanoparticles comprising a thiol-binding metallic core conjugated to fluoroquinolone antibiotics was found to be highly efficacious in eradicating persister cells and for treating infections for a broad range of bacterial species, including Gram-positive and Gram-negative bacteria. Such treatment was effective not only in eradicating planktonic bacteria but also bacteria in biofilms.

In one aspect, a nanoparticle is provided comprising a thiol-binding metallic core conjugated to a fluoroquinolone antibiotic. In certain embodiments, the fluoroquinolone antibiotic is selected from the group consisting of ciprofloxacin, ofloxacin, moxifloxacin, gemifloxacin, levofloxacin, and finafloxacin.

In certain embodiments, the thiol-binding metallic core comprises one or more of gold, silver, nickel, copper, aluminum, or cobalt, or an oxide, carbide, nitride, or alloy thereof. In certain embodiments, the nanoparticle is biocompatible with human cells.

In one embodiment, the nanoparticle comprises a gold metallic core conjugated to 47 ciprofloxacin molecules (see, e.g., Example 2). The ciprofloxacin can be conjugated to the gold metallic core, for example, through a bond between an amino group of the ciprofloxacin and a gold atom of the metallic core.

In certain embodiments, the metallic core has a diameter of less than 10 nm. In some embodiments, the diameter ranges from about 1 nm to about 5 nm, including any diameter within this range such as 1 nm, 2 nm, 3 nm, 4 nm, or 5 nm. In one embodiment, the metallic core has a diameter of about 4 nm.

In certain embodiments, the nanoparticle further comprises a cell penetrating peptide attached to the outer surface of the nanoparticle. Exemplary cell penetrating peptides include, without limitation, HIV-Tat, penetratin, transportan, octaarginine, nonaarginine, antennapedia, TP10, Buforin II, MAP (model amphipathic peptide), K-FGF, Ku70, mellittin, pVEC, Pep-1, SynB1, Pep-7, CADY, GALA, pHLIP, KALA, R7W, and HN-1, which can readily transport nanoparticles across plasma membranes.

In certain embodiments, the nanoparticle further comprises an anionic moiety attached to the outer surface of the nanoparticle. The anionic moiety may include for example, without limitation, a carboxylate functional group, a phosphate functional group, or a sulfate functional group.

In certain embodiments, the nanoparticle further comprises a nucleotide, wherein the nucleotide is conjugated to the thiol-binding metallic core. In some embodiments, the nucleotide is adenosine triphosphate (ATP), adenosine monophosphate (AMP), adenosine diphosphate (ADP), or an analog thereof. Exemplary nucleotide analogs include, without limitation, a phosphorothioate analog (e.g., ATPαS, ATPβS, ATPγS, ADPαS, ADPβS, AMPS), a deoxyribonucleotide analog (e.g., 2'-deoxyATP, 2'-deoxyADP, 2'-deoxyAMP), a 7-deaza purine nucleotide analog (e.g., 7-deazaadenosine-5'-triphosphate (7-deaza-ATP)), a phosphomethylphosphonic acid adenylate ester analog (e.g., β,γ-methyleneadenosine 5'-triphosphate (AMP-PCP)). In one embodiment, the nanoparticle comprises a gold metallic core conjugated to ATP (AuNC@ATP), AMP (AuNC@AMP), or ADP (AuNC@ADP). In another embodiment, the nanoparticle comprises a gold metallic core conjugated to a nucleotide analog such as a phosphorothioate analog (e.g., ATPαS, ATPβS, ATPγS, ADPαS, ADPβS, AMPS), a deoxyribonucleotide analog (e.g., 2'-deoxyATP, 2'-deoxyADP, 2'-deoxyAMP), a 7-deaza purine nucleotide analog (e.g., 7-deazaadenosine-5'-triphosphate (7-deaza-ATP)), a phosphomethylphosphonic acid adenylate ester analog (e.g., β,γ-methyleneadenosine 5'-triphosphate (AMP-PCP)), or a combination thereof.

In certain embodiments, the nanoparticle further comprises a polyethylene glycol (PEG) polymer, wherein the PEG polymer is attached to the outer surface of the nanoparticle. In some embodiments, the PEG polymer is functionalized with the anionic moiety. For example, the PEG polymer may be functionalized with an acid moiety. In some embodiments, the PEG polymer comprises a carboxylate group (e.g., PEG carboxylic acid (PEG-COOH), hydroxyl PEG carboxylic acid, PEG-acetic acid, PEG glutaric acid, PEG succinic acid, PEG glutaramide acid, PEG succinamide acid). In some embodiments, the PEG polymer is functionalized with a thiol group and an anionic moiety (e.g., thiol-carboxyl polyethylene glycol (COOH-PEG-SH)). In other embodiments, the PEG polymer is functionalized with a cationic moiety such as an amine group (PEG-NH₂) or a neutral moiety such as a hydroxyl group (PEG-OH).

In certain embodiments, the nanoparticle is further functionalized with a D-carbohydrate including, without limitation, D-glucose, D-mannitol, D-arabinose, or D-xylose.

In certain embodiments, the nanoparticle is further functionalized with a D-amino acid including, without limitation, D-glutamic acid, D-leucine, D-methionine, D-tyrosine and D-tryptophan.

In certain embodiments, the nanoparticle is further functionalized with a nucleic acid comprising a CrcZ RNA sequence or a CrcZ A-rich motif sequence. In certain embodiments, the CrcZ RNA sequence comprises the nucleotide sequence of SEQ ID NO:1, or a or sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto; or an RNA equivalent thereof. In certain embodiments, the CrcZ A-rich motif sequence comprises: a) ACAACAACAATAACAA (SEQ ID NO:2); b) CAATAAGAA; c) AACAAGAACAA (SEQ ID NO:3); d) AGAACAACAAAA (SEQ ID NO:4); e) ACAACAAGAACAA (SEQ ID NO:5); f) AGAACAAGAACAA (SEQ ID NO:6); g) AACAACAA; h) AAAAACAA; or i) an RNA equivalent of a)-i).

In certain embodiments, the nanoparticle further comprises an antimicrobial agent having bactericidal activity against persister cells or bacteria residing in biofilms, wherein the antimicrobial agent is attached to the outer surface of the nanoparticle.

In certain embodiments, the nanoparticle further comprises a linker connecting a functionalization agent (e.g., cell penetrating peptide, nucleic acid comprising CrcZ RNA, an antimicrobial agent) to the outer surface of the nanoparticle.

In certain embodiments, the nanoparticle ranges in size from about 1 nm to about 500 nm in length, including any length within this range such as 1, 2, 3, 4, 5, 6, 7, 8, 9, 10, 12, 14, 16, 18, 20, 30, 40, 50, 60, 70, 80, 90, 100, 120, 140, 160, 180, 200, 220, 240, 260, 280, 300, 320, 340, 360, 380, 400, 420, 440, 460, 480, or 500 nm in length. In some embodiments, the nanoparticle is less than 10 nm in length. In some embodiments, the nanoparticles are about 1 to about 5 nm in length.

In another aspect, a composition comprising a nanoparticle described herein is provided. In certain embodiments, the composition further comprises a pharmaceutically acceptable excipient or carrier.

In certain embodiments, the composition further comprises an antibiotic. Exemplary antibiotics include, without limitation, fluoroquinolones, aminoglycosides, penicillins, tetacyclines, cephalosporins, macrolides, sulfonamides, carbapenems, ansamycins, carbacephems, carbapenems, lincosamides, monobactams, and oxazolidinones. For example, the antibiotic may include a fluoroquinolone such as ofloxacin, moxifloxacin, ciprofloxacin, gemifloxacin, levofloxacin, or finafloxacin, or a derivative thereof.

In another aspect, a method of treating an infection in a subject is provided, the method comprising administering a therapeutically effective amount of a composition comprising a nanoparticle described herein to the subject. In some embodiments, the method further comprises administering a therapeutically effective amount of at least one antibiotic in combination with the composition comprising the nanoparticle.

Exemplary antibiotics include, without limitation, fluoroquinolones, aminoglycosides, penicillins, tetacyclines, cephalosporins, macrolides, sulfonamides, carbapenems, ansamycins, carbacephems, carbapenems, lincosamides, monobactams, and oxazolidinones. For example, the antibiotic may include a fluoroquinolone such as ofloxacin or a derivative thereof.

In certain embodiments, the subject has a chronic infection. In some embodiments, the subject has an infection including, without limitation, an ear infection, a cutaneous infection, a lung infection, chronic suppurative otitis media (CSOM), an infection associated with cystic fibrosis, tuberculosis, or an infection in a wound. In some embodiments, the infection is associated with formation of a bacterial biofilm in the subject. In certain embodiments, the infection comprises pathogenic bacteria that are resistant to one or more antibiotics. In some embodiments, the subject has previously been treated for the infection with one or more antibiotics that have not successfully cleared the infection. In another embodiment, the infection is an infection (e.g. *Pseudomonas*) in a subject who has cystic fibrosis.

In certain embodiments, the treatment eradicates all or most biofilm bacteria and planktonic bacteria. In some embodiments, the treatment eradicates all or most persister cells, which may be, for example, in a biofilm or internalized by a macrophage. In some embodiments, the persister cells that are eradicated by the treatment described herein are multidrug tolerant persister cells. Treatment may eradiate persister cells comprising either Gram-negative or Gram-positive bacteria, including, without limitation, *Pseudomonas aeruginosa* persister cells.

In certain embodiments, multiple cycles of treatment are administered to the subject. For example, nanoparticles described herein may be administered alone or in combination with an antibiotic either intermittently or according to a daily dosing regimen.

Compositions comprising nanoparticles may be administered by any suitable mode of administration. For example, the composition may be administered intravenously, subcutaneously, by inhalation, or topically. Alternatively, the composition may be administered locally at the site of infected tissue. For example, for an ear infection, the composition comprising nanoparticles may be administered locally into the ear canal.

In another embodiment, a method of eradicating bacteria in a biofilm is provided, the method comprising contacting the biofilm with an effective amount of a composition comprising a nanoparticle described herein. In some embodiments, the method further comprises contacting the biofilm with an effective amount of at least one antibiotic. The methods described herein may be used to eradicate bacteria, for example, in a biofilm on a medical device, a personal hygiene article, a toiletry, a cosmetic, a disinfectant, a cleaning solution, or in a water treatment or distribution system.

In another embodiment, a method of eradicating dormant bacteria comprising persister cells is provided, the method comprising contacting the dormant bacteria with an effective amount of a composition comprising a nanoparticle described herein. In some embodiments, the method further comprises contacting the dormant bacteria with an effective amount of at least one antibiotic. The dormant bacteria may be present, for example, in a biofilm, in a liquid culture, or on an inanimate surface.

In another aspect, a method of killing fluoroquinolone-resistant bacteria is provided, the method comprising contacting the fluoroquinolone-resistant bacteria with a nanoparticle described herein.

In another aspect, a method of increasing production of oxygen species (ROS) in a macrophage infected with persister bacteria is provided, the method comprising contacting the macrophage with an effective amount of a nanoparticle described herein.

In another aspect, a method of increasing autophagy in a macrophage infected with persister bacteria is provided, the method comprising contacting the macrophage with an effective amount of a nanoparticle described herein.

In another aspect, a method of increasing secretion of tumor necrosis factor-alpha (TNF-α) from a macrophage infected with persister bacteria is provided, the method comprising contacting the macrophage with an effective amount of a nanoparticle described herein.

In certain embodiments, a nanoparticle described herein (e.g., AuNC@ATP) is used in combination with a DNA-damaging antimicrobial agent to increase persistent bacterial infections treatment efficiency. The nanoparticle can also be used as a monotherapy to selectively kill persister cells with DNA damage (see, e.g., Example AuNC@ATP). In some embodiments, the nanoparticle is used in combination with a DNA-damaging antimicrobial agent to decrease classical bacterial resistance development due to a genetic mutation.

In another aspect, a kit is provided comprising a nanoparticle described herein and instructions for treating a bacterial infection. In some embodiments, the kit further comprises an antibiotic.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF EMBODIMENTS

Figure 1:
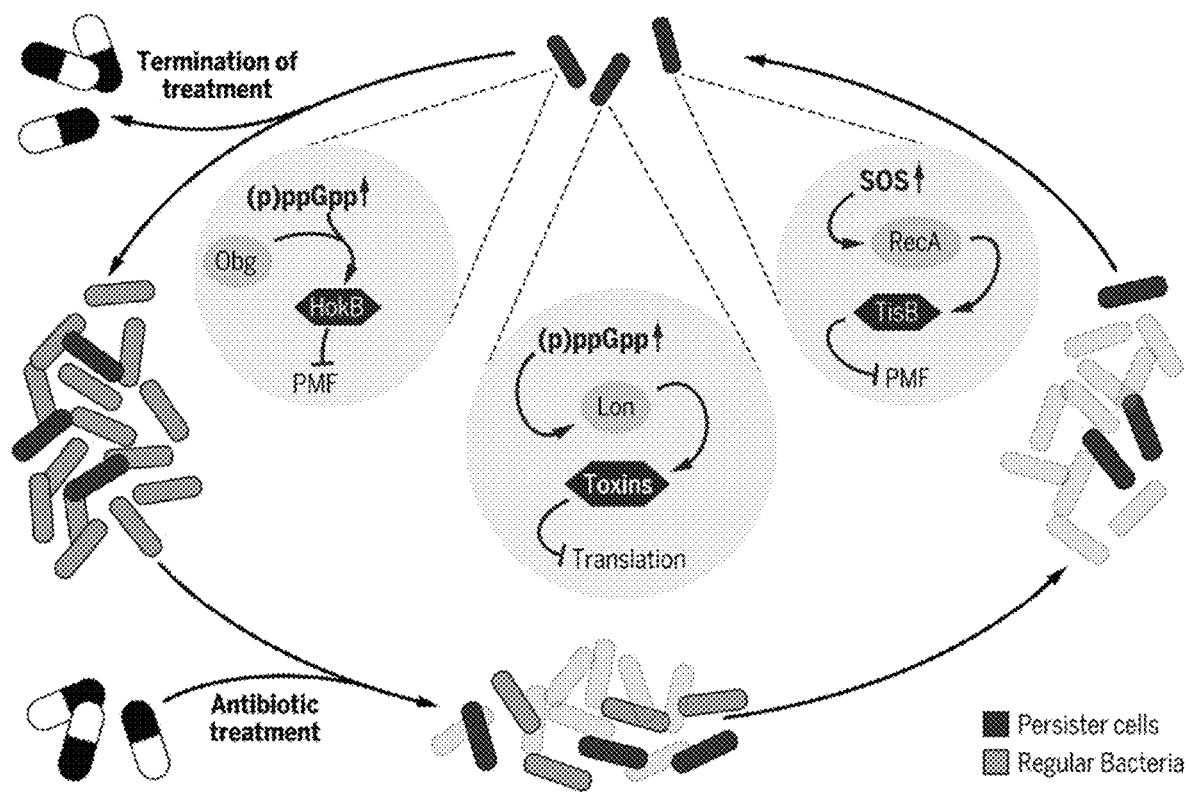
FIG. 1. Bacterial persister cells defy antibiotic treatment. Dead bacteria after antibiotic treatment (light gray).
Figure 2A:
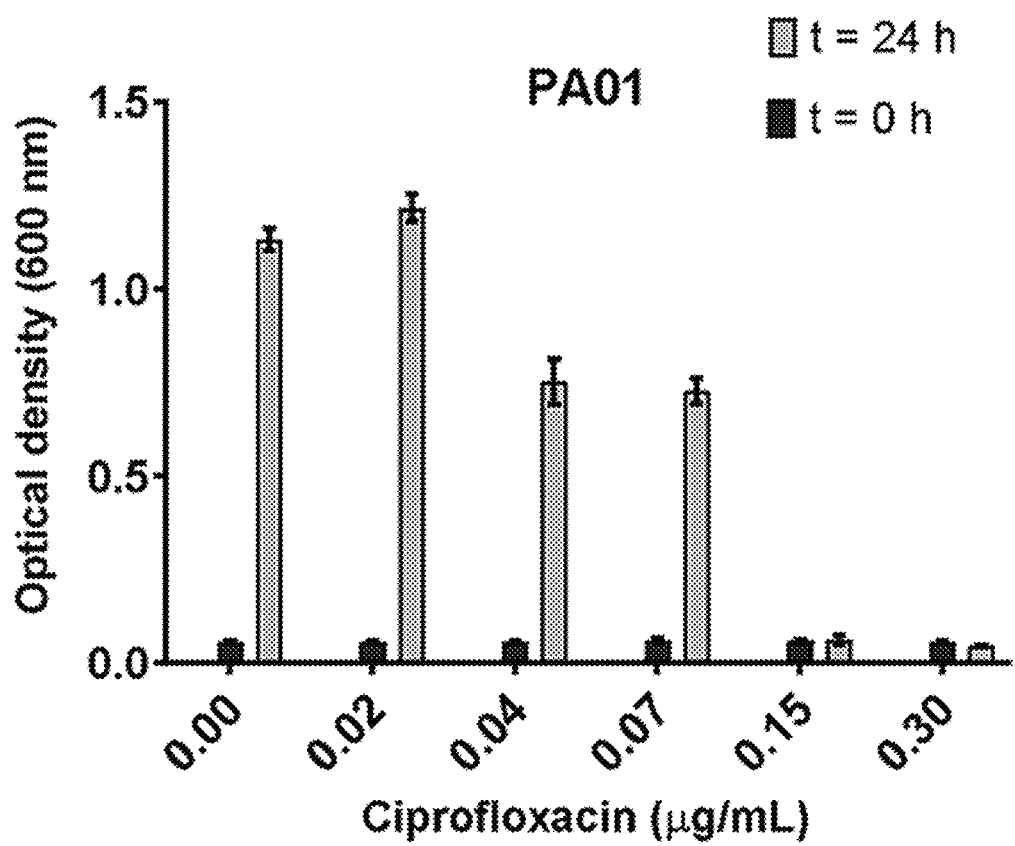
FIGS. 2A-2F. Ciprofloxacin nanoformulation (AuNC) hypersensitizes both PA01 and extensively drug-resistant (XDR) PA (FIGS. 2A-2D). PA01 is sensitized (FIGS. 2A-2B). PA (XDR) is not susceptible to 127.6 µg/ml of ciprofloxacin (FIG. 2C). Whereas 0.62 µg/ml of ciprofloxacin within the AuNC can inhibit the growth of PA (XDR) (FIG. 2D). The IC50 (half-maximal cytotoxic concentration) of ciprofloxacin and AuNC against murine macrophage RAW 264.7 cells are 77.36 µg/ml and 8.375 µg/ml, respectively (FIGS. 2E-2F). The higher the selectivity index (SI=IC50/MIC), the more effective and safe an antibiotic would be during in vivo treatment for a given bacterial infection. The SI value of ciprofloxacin and AuNC for PA (XDR) are 0.6 and 13, respectively. This suggest that AuNC is safer that ciprofloxacin. Data shown reflect mean±SD of three replicates.
Figure 2B:
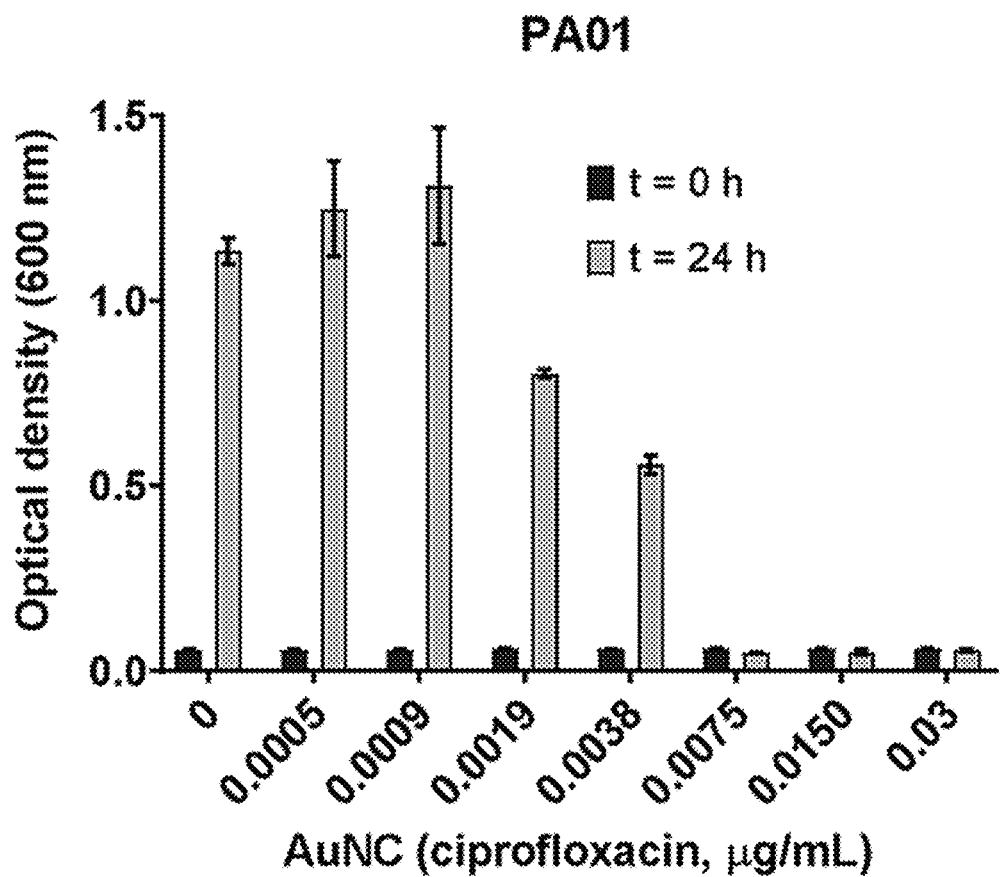
Figure 2C:
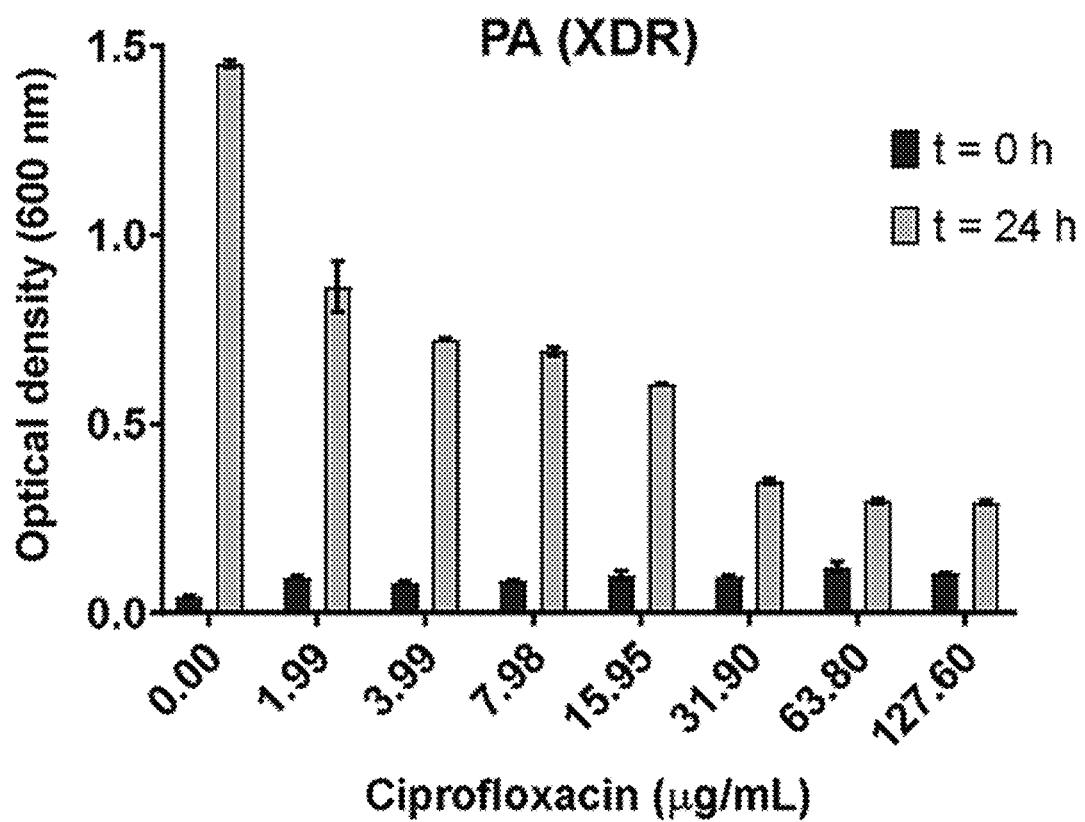
Figure 2D:
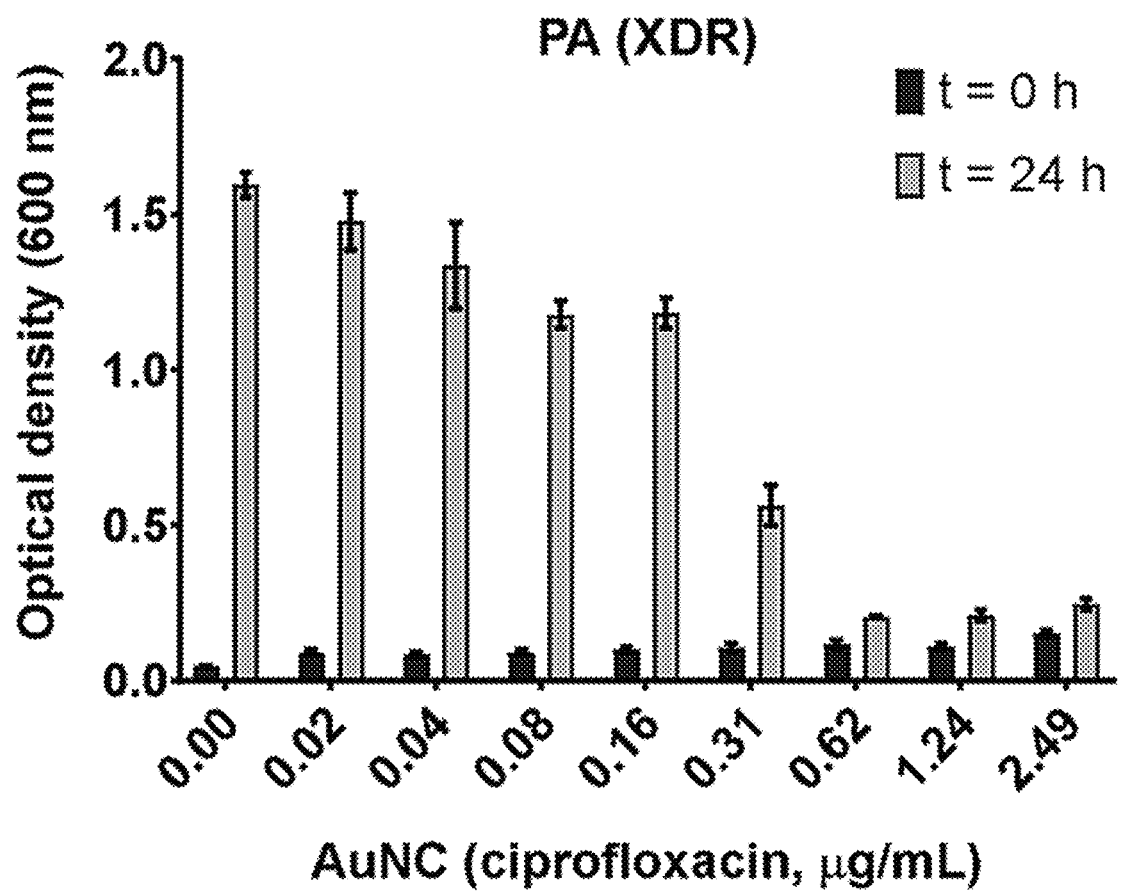
Figure 2E:
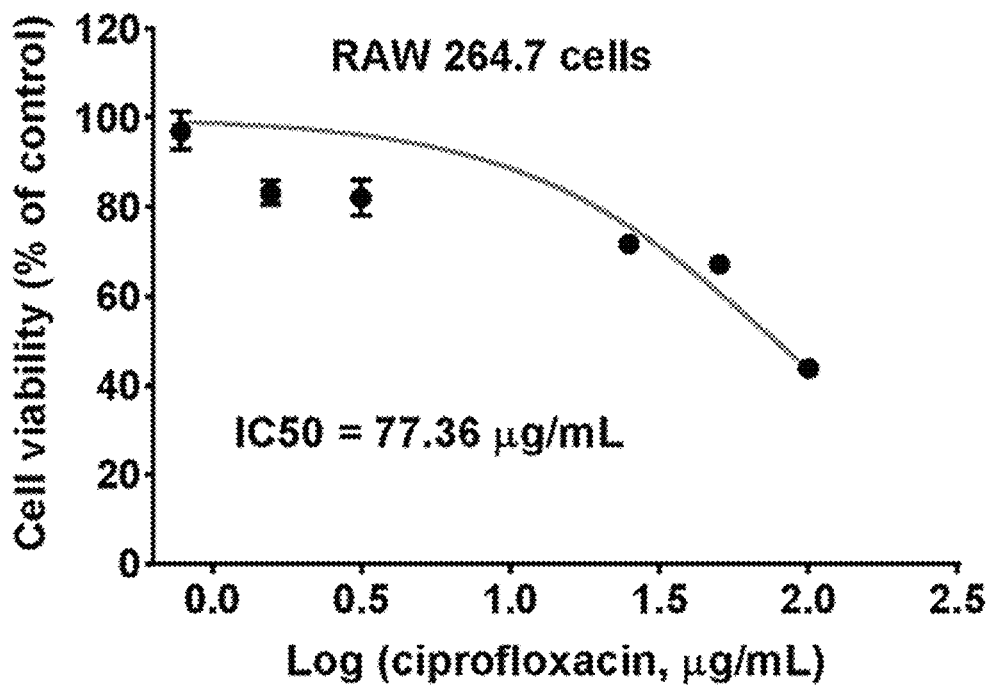
Figure 2F:
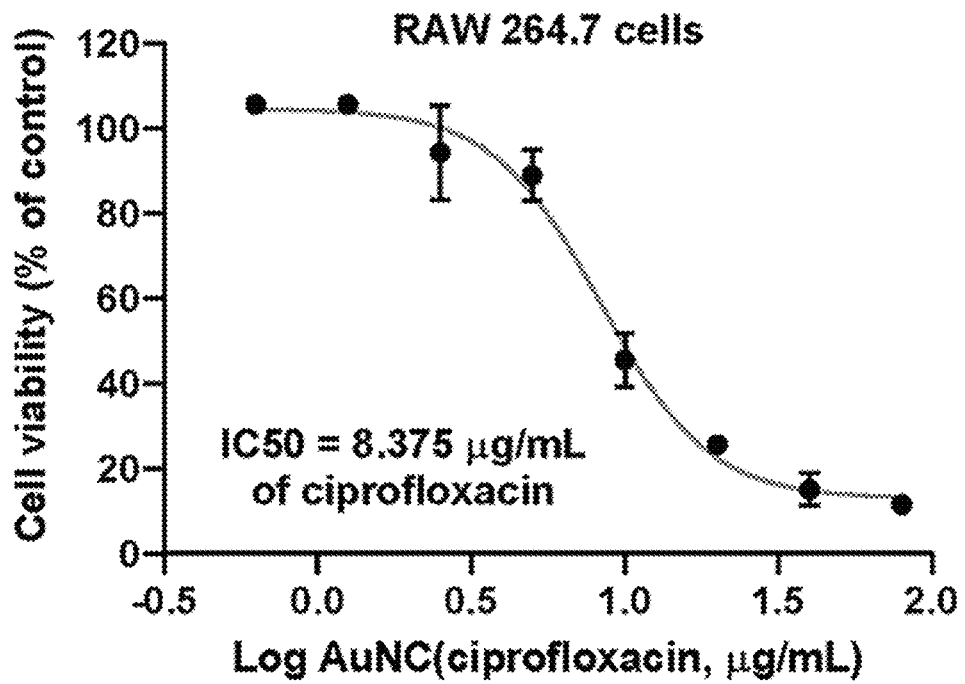

Compositions comprising nanoparticles comprising a thiol-binding metallic core conjugated to fluoroquinolone antibiotics and methods of using them in treating bacterial infections are provided.

Before the present compositions comprising nanoparticles comprising a thiol-binding metallic core conjugated to fluoroquinolone antibiotics and methods of using them in treating bacterial infections are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a bacterial cell" includes a plurality of such bacterial cells and reference to "the nanoparticle" includes reference to one or more nanoparticles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "nanoparticle" refers to an organic, inorganic, or hybrid nanoparticle having a size ranging from about 1 nm to about 500 nm in length. Nanoparticles may have dimensions of 500 nm or less, including 250 nm or less, or 200 nm or less, or 150 nm or less, or 100 nm or less, or 50 nm or less, or 40 nm or less, or 30 nm or less, or 25 nm or less, or 20 nm or less, or 15 nm or less, or 10 nm or less, or 5 nm or less, or 4 nm or less, or 3 nm or less, or 2 nm or less, or 1 nm or less. In some instances, the nanoparticle has dimensions of 2 nm or less.

"Diameter" as used in reference to a shaped structure (e.g., nanoparticle) refers to a length that is representative of the overall size of the structure. The length may in general be approximated by the diameter of a circle or sphere that circumscribes the structure.

The term "persister cells" refers to cells that have entered a non-growing (i.e., dormant) or extremely slow-growing physiological state that renders them less susceptible or resistant to antimicrobial drugs. Such cells may "persist" after planktonic bacterial cells have been eradicated by the immune system or conventional treatment with an antimicrobial agent. Persister cells are commonly found in biofilms.

As used herein, the term "antimicrobial agent" is interchangeable with the term "antibiotic" and refers to any agent capable of having bactericidal or bacterial static effects on growth. Antibiotics include, but are not limited to, a β-lactam antibiotic, an aminoglycoside, an aminocyclitol, a quinolone, a tetracycline, a macrolide, a lincosamide, a glycopeptide, a lipopeptide, a polypeptide antibiotic, a sulfonamide, trimethoprim, chloramphenicol, isoniazid, a nitroimidazole, a rifampicin, a nitrofuran, methenamine, and mupirocin.

The term "anti-bacterial effect" means the killing of, or inhibition or stoppage of the growth and/or reproduction of bacteria.

The term "efflux pump" as used herein refers to a protein assembly, which transports or exports substrate molecules from the cytoplasm or periplasm of a cell, in an energy-dependent or independent fashion. The term "efflux pump activity" as used herein refers to a mechanism responsible for export of substrate molecules, including antimicrobial agents, outside the cell. The term "efflux pump inhibitor" as used herein refers to a compound, which interferes with the ability of an efflux pump to transport or export a substrate, including antimicrobial agent.

The term "CrcZ" as used herein encompasses all forms of CrcZ and also includes biologically active fragments, for example, including one or more CrcZ A-rich motifs, variants, analogs, and derivatives thereof that retain biological activity (e.g., disrupting or interfering with bacterial biofilm formation).

A CrcZ RNA, DNA, nucleic acid, polynucleotide, or oligonucleotide refers to a molecule derived from any species of CrcZ-expressing bacteria. The molecule need not be physically derived from bacteria, but may be synthetically or recombinantly produced. A number of CrcZ nucleic acid sequences are known. Representative sequences of CrcZ (SEQ ID NO:1) and CrcZ A-rich motifs (SEQ ID NOS:2-6) from *Pseudomonas aeruginosa* are presented in the Sequence Listing. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct functionalized nanoparticles for treating a bacterial infection, as described herein.

By "fragment" is intended a molecule consisting of only a part of the intact full-length sequence and structure. For a nucleic acid, the fragment can include a 5' deletion a 3' deletion, and/or an internal deletion of the nucleic acid. Active fragments of a particular nucleic acid will generally include at least about 5-16 contiguous nucleotides of the full length molecule, but may include at least about 8-20 contiguous nucleotides of the full length molecule, and can include at least about 20-50 or more contiguous nucleotides of the full length molecule, or any integer between 5 nucleotides and the full length sequence, provided that the fragment in question retains biological activity (e.g., the ability to eradicate a bacterial infection). For a protein or peptide, the fragment can include a C-terminal deletion an N-terminal deletion, and/or an internal deletion of the polypeptide. Active fragments of a particular protein or peptide will generally include at least about 5-14 contiguous amino acid residues of the full length molecule, but may include at least about 15-25 contiguous amino acid residues of the full length molecule, and can include at least about 20-50 or more contiguous amino acid residues of the full length molecule, or any integer between 5 amino acids and the full length sequence, provided that the fragment in question retains biological activity (e.g., the ability to eradicate a bacterial infection).

The term "treatment" as used herein refers to (1) the prevention of infection or reinfection (prophylaxis), (2) the eradication of an existing infection, or (3) the reduction or elimination of symptoms of an infectious disease of interest (therapy).

By "therapeutically effective dose or amount" of nanoparticles is intended an amount that, when administered alone or in combination with an antibiotic, as described herein, brings about a positive therapeutic response, such as improved recovery from an infection, including any infection caused by Gram-positive or Gram-negative bacteria. Additionally, a therapeutically effective dose or amount may eradicate persister cells as well as other bacterial cells, including planktonic bacteria as well as bacteria in biofilms, increase ROS accumulation in macrophages, stimulate TNF-α secretion from activated macrophages, restore autophagy, and/or deplete glutathione, catalases, and hydroperoxide reductases. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

"Substantially purified" generally refers to isolation of a component such as a substance (compound, nanoparticle, nucleic acid, polynucleotide, RNA, DNA, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography, gel filtration, and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "recipient", "individual", "subject", "host", and "patient", are used interchangeably herein and refer to any vertebrate subject for whom diagnosis, treatment, or therapy is desired, particularly humans. By "vertebrate subject" is meant any member of the subphylum Chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

"Biocompatible" generally refers to a material and any metabolites or degradation products thereof that are generally non-toxic to the recipient and do not cause any significant adverse effects to the subject.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The term "hydrophilic polymer" refers to a material that has the property of dissolving in, absorbing, or mixing easily with water, and comprises repeating units constituting a molecular weight of at least 200 up to 8,000 or more. Hydrophilic polymers include, without limitation, polyethylene glycol (PEG) as well as other materials, which can be used to solubilize nanoparticles. Materials for this purpose include polyethylene glycol (PEG), polyoxyethylene, polymethylene glycol, polytrimethylene glycols, polyvinylpyrrolidones, poly lysine (D or L) and derivatives, and polyoxyethylene-polyoxypropylene block polymers and copolymers. The hydrophilic polymers can be linear or multiply branched, and may include multi-arm block copolymers. The hydrophilic polymer renders the nanoparticles soluble when attached thereto in sufficient numbers.

Nanoparticles for Treatment of Bacterial Infections

Compositions comprising nanoparticles comprising a thiol-binding metallic core conjugated to fluoroquinolone antibiotics and methods of using them in treating bacterial infections are provided. In particular, such nanoparticles are useful for treating chronic infections associated with production of bacterial biofilms, which are not responsive to conventional antibiotic treatment. Without being bound by theory, bacteria in biofilms tend to be more resistant to treatment with antibiotics, in part, because the biofilm extracellular matrix and outer layers of cells protect bacterial cells in the interior. In addition, many bacterial cells in a biofilm adopt a dormant phenotype, becoming metabolically inactive, which makes them less susceptible to antibiotics that need to be metabolized in order to be effective (e.g., penicillin requires cell wall remodeling in an active bacterial cell in order to cause cell death). Dormant cells in biofilms, which have entered a non-growing or extremely slow-growing physiological state, and as a result have become resistant to antimicrobial drugs, are referred to herein as "persister cells" because of their ability to persist after other active bacterial cells have been eradicated by the immune system or antimicrobial agents. Persister cells are often associated with chronic infections because of the difficulty of eradicating them with conventional antibiotic treatment.

Persister cells have the ability to limit production of reactive oxygen species (ROS) in macrophages, which reduces the bactericidal activity of fluoroquinolone antibiotics. Therefore, a thiol antioxidant inhibition strategy was implemented to improve the efficacy of fluoroquinolone antibiotics against persister cells. As mentioned above, nanoparticles are provided comprising a thiol-binding metallic core conjugated to a fluoroquinolone antibiotic. The use of a nanoparticle having a thiol-binding metallic core inhibits thiol-based antioxidants and raises intracellular levels of hydroxyl radicals that kill persister cells (see, e.g., Examples). The compositions and methods described herein are especially useful for treating chronic infections to render persister cells in biofilms more susceptible to fluoroquinolone antibiotic treatment.

The thiol-binding metallic core may comprise any metal that can bind to and inhibit thiol-based antioxidants. For example, the thiol-binding metallic core may comprise, without limitation, one or more of gold, silver, nickel, copper, aluminum, or cobalt, or an oxide, carbide, nitride, or alloy thereof. In certain embodiments, the nanoparticle is biocompatible with human cells.

Exemplary fluoroquinolone antibiotics that can be conjugated to the metallic core include, without limitation ciprofloxacin, ofloxacin, moxifloxacin, gemifloxacin, levofloxacin, and finafloxacin. See Example 2 for a description of an exemplary nanoparticle comprising a thiol-binding gold metallic core conjugated to 47 ciprofloxacin molecules. Ciprofloxacin is conjugated to the gold metallic core through a bond between an amino group of the ciprofloxacin and a gold atom.

In addition, nanoparticles may be functionalized with one or more other agents, including anionic moieties, polymers (e.g., PEGylated nanoparticles), cell transduction peptides (e.g., TAT), anti-microbial agents, and/or bacterial RNAs (e.g., CrcZ) that enhance delivery and/or the effectiveness of the nanoparticles in eradicating bacteria.

The functionalized nanoparticle may be an organic, inorganic, or hybrid nanoparticle having a size ranging from about 1 nm to about 500 nm in length. In some embodiments, the functionalized nanoparticle has dimensions of 500 nm or less, including 250 nm or less, or 200 nm or less, or 150 nm or less, or 100 nm or less, or 50 nm or less, or 40 nm or less, or 30 nm or less, or 25 nm or less, or 20 nm or less, or 15 nm or less, or 10 nm or less, or 5 nm or less, or 4 nm or less, or 3 nm or less, or 2 nm or less, or 1 nm or less.

In some embodiments, the outer surface of a nanoparticle is functionalized with an anionic moiety. The anionic moiety may include, for example, without limitation, a carboxylate functional group, a phosphate functional group, or a sulfate functional group.

In certain embodiments, the nanoparticle further comprises a nucleotide, wherein the nucleotide is conjugated to the thiol-binding metallic core. In some embodiments, the nucleotide is adenosine triphosphate (ATP), adenosine monophosphate (AMP), adenosine diphosphate (ADP), or an analog thereof. Exemplary nucleotide analogs include, without limitation, a phosphorothioate analog (e.g., ATPαS, ATPβS, ATPγS, ADPαS, ADPβS, AMPS), a deoxyribonucleotide analog (e.g., 2'-deoxyATP, 2'-deoxyADP, 2'-deoxyAMP), a 7-deaza purine nucleotide analog (e.g., 7-deazaadenosine-5'-triphosphate (7-deaza-ATP)), a phosphomethylphosphonic acid adenylate ester analog (e.g., β,γ-methyleneadenosine 5'-triphosphate (AMP-PCP)), or a combination thereof. In one embodiment, the nanoparticle comprises a gold metallic core conjugated to adenosine triphosphate (AuNC@ATP), AMP (AuNC@AMP), ADP (AuNC@ADP), or an analog thereof such as a phosphorothioate analog (e.g., ATPαS, ATPβS, ATPγS, ADPαS, ADPβS, AMPS), a deoxyribonucleotide analog (e.g., 2'-deoxyATP, 2'-deoxyADP, 2'-deoxyAMP), a 7-deaza purine nucleotide analog (e.g., 7-deazaadenosine-5'-triphosphate (7-deaza-ATP)), a phosphomethylphosphonic acid adenylate ester analog (e.g., β,γ-methyleneadenosine 5'-triphosphate (AMP-PCP)), or a combination thereof.

In some embodiments, the outer surface of a nanoparticle is functionalized with a hydrophilic polymer to solubilize the nanoparticle. Exemplary polymers that can be used for this purpose include, without limitation, polyethylene glycol (PEG), polyoxyethylene, polymethylene glycol, polytrimethylene glycols, polyvinyl-pyrrolidones, polylysine (D or L) and derivatives, and polyoxyethylene-polyoxypropylene block polymers and copolymers. The hydrophilic polymers can be linear or multiply branched, and may include multi-arm block copolymers. The hydrophilic polymer renders the nanoparticles soluble when attached thereto in sufficient numbers. Additionally, a polymer may also protect nanoparticles from protein adsorption and reduce immunological reactions to the nanoparticles, which helps to prolong their stability in the bloodstream.

In some embodiments, the outer surface of the nanoparticle is functionalized with a polyethylene glycol (PEG) polymer (i.e., PEGylated nanoparticle). The PEG polymer may be branched or unbranched. In some cases, the PEG polymer has an average molecular mass of 1000 Da or more, such as 1500 Da or more, including 2000 Da or more, or 3000 Da or more, or 4000 Da or more, or 5000 Da or more, or 6000 Da or more, or 7000 Da or more, or 8000 Da or more, or 9000 Da or more, or 10,000 Da or more, or 15,000 Da or more, or 20,000 Da or more. In certain instances, the PEG polymer has an average molecular mass of 2000 Da. In certain instances, the PEG polymer has an average molecular mass of 2000 Da.

In some embodiments, the PEG polymer is functionalized with the anionic moiety. For example, the PEG polymer may be functionalized with an acid moiety. In some embodiments, the PEG polymer comprises a carboxylate group (e.g., PEG carboxylic acid (PEG-COOH), hydroxyl PEG carboxylic acid, PEG-acetic acid, PEG glutaric acid, PEG succinic acid, PEG glutaramide acid, PEG succinamide acid). In other embodiments, the PEG polymer is functionalized with a cationic moiety such as an amine group (PEG-NH$_2$) or a neutral moiety such as a hydroxyl group (PEG-OH).

In certain embodiments, the nanoparticle further comprises a D-carbohydrate including, without limitation, D-glucose, D-mannitol, D-arabinose, or D-xylose, wherein the D-carbohydrate is attached to the outer surface of the nanoparticle.

In certain embodiments, the nanoparticle further comprises a D-amino acid including, without limitation, D-glutamic acid, D-leucine, D-methionine, D-tyrosine and D-tryptophan, wherein the D-amino acid is attached to the outer surface of the nanoparticle.

In certain embodiments, the nanoparticle is linked to an internalization sequence, a protein transduction domain, or a cell penetrating peptide to facilitate entry into a cell. Cell penetrating peptides that can be used include, but are not limited to, HIV-Tat, penetratin, transportan, octaarginine, nonaarginine, antennapedia, TP10, Buforin II, MAP (model amphipathic peptide), K-FGF, Ku70, mellittin, pVEC, Pep-1, SynB1, Pep-7, CADY, GALA, pHLIP, KALA, R7W, and HN-1, which can readily transport nanoparticles across plasma membranes (see, e.g., Jones et al. (2012) "Cell entry of cell penetrating peptides and tales of tails wagging dogs," J. Control Release. 2012, in press; Fonseca et al. (2009) Adv. Drug Deliv. Rev. 61(11):953-64; Schwarze et al. (1999) Science. 285(5433):1569-72; Derossi et al. (1996) J. Biol. Chem. 271(30):18188-18193; Fuchs et al. (2004) Biochemistry 43(9):2438-2444; and Yuan et al. (2002) Cancer Res. 62(15):4186-4190).

In certain embodiments, the nanoparticle is functionalized with a nucleic acid comprising a CrcZ RNA sequence or a biologically active fragment thereof, for example, including one or more CrcZ A-rich motifs, or a variant, analog, or derivative thereof that retains biological activity (e.g., disrupting or interfering with bacterial biofilm formation). CrcZ RNA sequences may be derived from any bacterial species expressing CrcZ. A number of CrcZ nucleic acid sequences are known. Representative sequences of CrcZ (SEQ ID NO:1) and CrcZ A-rich motifs (SEQ ID NOS:2-6) from *Pseudomonas aeruginosa* are presented in the Sequence Listing. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct functionalized nanoparticles for treating a bacterial infection, as described herein.

The nanoparticle is typically spherical in shape, but nanoparticles having other shapes may also be used. For example, the nanoparticle may have a shape such as, but not limited to, an ellipsoid, a rod, a cone, a cube, a cuboid (e.g., a rectangular box), a pyramid, or an irregular shape, etc. In certain instances, combinations of different shapes of nanoparticles may be included in a composition. In some embodiments, the nanoparticle is substantially spherical in shape, and thus may have dimensions measured as a diameter of a sphere. For example, nanoparticles may have an average diameter of 500 nm or less, including 250 nm or less, or 200 nm or less, or 150 nm or less, or 100 nm or less, or 50 nm or less, or 40 nm or less, or 30 nm or less, or 25 nm or less, or 20 nm or less, or 15 nm or less, or 10 nm or less, or 5 nm or less, or 4 nm or less, or 3 nm or less, or 2 nm or less, or 1 nm or less. In some instances, a substantially spherical nanoparticle has an average diameter of 2 nm or less.

Nanoparticles may have dimensions of 500 nm or less, including 250 nm or less, or 200 nm or less, or 150 nm or less, or 100 nm or less, or 50 nm or less, or 40 nm or less, or 30 nm or less, or 25 nm or less, or 20 nm or less, or 15 nm or less, or 10 nm or less, or 5 nm or less, or 4 nm or less, or 3 nm or less, or 2 nm or less, or 1 nm or less. In some instances, the nanoparticle has dimensions of 2 nm or less. In certain embodiments, the metallic core has a diameter of less than 10 nm. In some embodiments, the diameter ranges from about 1 nm to about 5 nm, including any diameter within this range such as 1 nm, 2 nm, 3 nm, 4 nm, or 5 nm. In one embodiment, the metallic core has a diameter of about 4 nm.

Conjugation

Surface functionalization of nanoparticles may be performed by any method known in the art. Functionalization of a nanoparticle involves conjugation of an agent (e.g., fluoroquinolone antibiotic, PEG, CrcZ, cell penetrating peptides, anionic moiety, and/or other agents or moieties) to an atom or molecule on the outer surface of the nanoparticle. A surface coating may be applied to nanoparticles to introduce functional groups to facilitate attachment of agents. For example, gold nanoparticles with surface coatings comprising thiol, carboxyl, amine, aldehyde, hydroxyl, or azide groups, PEG, dextran, streptavidin, or maleimide and compounds to facilitate bioconjugation are commercially available from a number of companies (e.g., SigmaAldrich (St. Louis, MO), and Cytodiagnostics (Burlington, Ontario, Canada), Creative Diagnostics (Shirley, NY), and Nanocs (New York, NY)). An agent may be conjugated to a nanoparticle directly or indirectly through a linker. Exemplary linkers include, without limitation, thioC6 linker (thiohexyl), PEG polymers, diethylenetriaminepentaacetic acid (DTPA), 1,4,7,10-tetraazacyclododecane-1,4,7,10-tetraacetic acid (DOTA), and hydrazide compounds. For a discussion of bioconjugation techniques, see, e.g., *Chemistry of Bioconjugates: Synthesis, Characterization, and Biomedical Applications* (R. Narain ed., Wiley, 2014), G. T. Hermanson Bioconjugate Techniques (Academic Press, 3$^{rd}$ edition, 2013), and *Bioconjugation Protocols: Strategies and Methods* (Methods in Molecular Biology, S. S. Mark ed., Humana Press, 2$^{nd}$ edition, 2011), Avvakumova et al. (2014) Trends Biotechnol. 32(1):11-20., Couto et al. (2017) Crit Rev Biotechnol. 37(2):238-250, Sivaram et al. (2018) Adv. Healthc Mater. 7(1), van Vught et al. (2014) Comput Struct Biotechnol J. 9:e201402001; Massa et al. (2016) Expert Opin Drug Deliv 13:1-15; Yeh et al. (2015) PLoS One 10(7):e0129681; Freise et al. (2015) Mol Immunol. 67(2 Pt A):142-152; herein incorporated by reference in their entireties.

A variety of conjugation methods and chemistries can be used to conjugate agents to a nanoparticle. Various zero-length, homo-bifunctional, and hetero-bifunctional cross-linking reagents can be used. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. Homo- and hetero-bifunctional reagents generally contain two identical or two non-identical sites, respectively, which may be reactive with amino, sulfhydryl, guanidino, indole, or nonspecific groups.

Suitable amino-reactive groups include, but are not limited to, N-hydroxysuccinimide (NHS) esters, imidoesters, isocyanates, acylhalides, arylazides, p-nitrophenyl esters, aldehydes, and sulfonyl chlorides. Suitable sulfhydryl-reactive groups include, but are not limited to, maleimides, alkyl halides, pyridyl disulfides, and thiophthalimides. In other embodiments, carbodiimides soluble in both water and organic solvent, are used as carboxyl-reactive reagents. These compounds react with free carboxyl groups forming a pseudourea that can then couple to available amines, yielding an amide linkage.

in some embodiments, an agent is conjugated to a nanoparticle using a homobifunctional crosslinker. In some embodiments, the homobifunctional crosslinker is reactive with primary amines. Homobifunctional crosslinkers that are reactive with primary amines include NHS esters, imidoesters, isothiocyanates, isocyanates, acylhalides, arylazides, p-nitrophenyl esters, aldehydes, and sulfonyl chlorides. Non-limiting examples of homobifunctional NHS esters include disuccinimidyl glutarate (DSG), disuccinimidyl suberate (DSS), bis(sulfosuccinimidyl)suberate (BS), disuccinimidyl tartarate (DST), disulfosuccinimidyl tartarate (sulfo-DST), bis-2-(succinimidooxycarbonyloxy)ethylsulfone (BSOCOES), bis-2-(sulfosuccinimidooxycarbonyloxy)ethylsulfone (sulfo-BSOCOES), ethylene glycolbis(succinimidylsuccinate) (EGS), ethylene glycolbis(sulfosuccinimidylsuccinate) (sulfo-EGS), dithiobis (succinimidylpropionate) (DSP), and dithiobis (sulfosuccinimidylpropionate (sulfo-DSP). Non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy) dipropionimidate (DM DP), dimethyl-,3'-(dimethylenedioxy)dipropionimidate (DDDP), dimethyl-3,3'-(tetramethylenedioxy)dipropionimidate (DTDP), and dimethyl-3,3'-dithiobispropionimidate (DTBP).

Non-limiting examples of homobifunctional isothiocyanates include: p-phenylenediisothiocyanate (DITC), and 4,4'-diisothiocyano-2,2'-disulfonic acid stilbene (DI DS). Non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate. Non-limiting examples of homobifunctional arylhalides include 1,5-difluoro-2,4-dinitrobenzene (DFDNB), and 4,4'-difluoro-3,3'-dinitrophenyl-sulfone. Non-limiting examples of homobifunctional aliphatic aldehyde reagents include glyoxal, malondialdehyde, and glutaraldehyde. Non-limiting examples of homobifunctional acylating reagents include nitrophenyl esters of dicarboxylic acids. Non-limiting examples of homobifunctional aromatic sulfonyl chlorides include phenol-2,4-disulfonyl chloride, and alpha-naphthol-2,4-disulfonyl chloride. Non-limiting examples of additional amino-reactive homobifunctional reagents include erythritolbiscarbonate, which reacts with amines to give biscarbamates.

In some embodiments, the homobifunctional crosslinker is reactive with free sulfhydryl groups. Homobifunctional crosslinkers reactive with free sulfhydryl groups include, e.g., maleimides, pyridyl disulfides, and alkyl halides. Non-limiting examples of homobifunctional maleimides include bismaleimidohexane (BMH), N,N'-(1,3-phenylene)bismaleimide, N,N'-(1,2-phenylene)bismaleimide, azophenyldimaleimide, and bis(N-maleimidomethyl)ether. Non-limiting examples of homobifunctional pyridyl disulfides include 1,4-di-3'-(2'-pyridyldithio)propionamidobutane (DPDPB). Non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyfiphenylhydrazine, and 1,2-di(bromoacetyfiamino-3-phenylpropane.

In some embodiments, an agent is conjugated to a nanoparticle using a heterobifunctional reagent. Suitable heterobifunctional reagents include amino-reactive reagents comprising a pyridyl disulfide moiety; amino-reactive reagents comprising a maleimide moiety; amino-reactive reagents comprising an alkyl halide moiety; and amino-reactive reagents comprising an alkyl dihalide moiety.

Non-limiting examples of hetero-bifunctional reagents with a pyridyl disulfide moiety and an amino-reactive NHS ester include N-succinimidyl-3-(2-pyridyldithio)propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio)toluene (SMPT), and sulfosuccinimidyl 6-α-methyl-α-(2-pyridyldithio)toluamidohexanoate (sulfo-LC-SMPT).

Non-limiting examples of heterobifunctional reagents comprising a maleimide moiety and an amino-reactive NHS ester include succinimidyl maleimidylacetate (AMAS), succinimidyl 3-maleimidylpropionate (BMPS), N-gamma-maleimidobutyryloxysuccinimide ester (GMBS) N-gamma-maleimidobutyryloxysulfosuccinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethylicyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

Non-limiting examples of heterobifunctional reagents comprising an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino) hexanoylamino)hexanoate (SIAXX), succinimidyl-6-(((4-(iodoacetyl)-amino)methyl)-cyclohexane-1-carbonyl) aminohexanoate (SIACX), and succinimidyl-4 ((iodoacetyl)-amino)methylcyclohexane-1-carboxylate (SIAC).

A non-limiting example of a hetero-bifunctional reagent comprising an amino-reactive NHS ester and an alkyl dihalide moiety is N-hydroxysuccinimidyl 2,3-dibromopropionate (SDBP). A non-limiting example of a hetero-bifunctional reagent comprising an alkyl halide moiety and an amino-reactive p-nitrophenyl ester moiety includes p-nitrophenyl iodoacetate (NPIA).

In another example, a 3-ThioC6 linker can be used to functionalize an agent with a thiol group to facilitate attachment to nanoparticles or other agents. For example, the 3-ThioC6 linker can be used to add a thiol group to the 3' terminus of a nucleic acid comprising a CrcZ RNA sequence or a CrcZ A-rich motif sequence. The free thiol can be used as a reactive functional group to attach maleimide compounds or for conjugation through disulfide linkages.

An alternative bioconjugation method uses click chemistry. Click chemistry reactions include the Huisgen 1,3-dipolar cycloaddition copper catalyzed reaction (Tornoe et al., 2002, J Organic Chem 67:3057-64), cycloaddition reactions such as Diels-Alder reactions, nucleophilic substitution reactions (especially to small strained rings like epoxy and aziridine compounds), reactions involving formation of urea compounds, and reactions involving carbon-carbon double bonds, such as alkynes in thiol-yne reactions. See, e.g., Kolb et al., 2004, Angew Chem Int Ed 40:3004-31; Evans, 2007, Aust J Chem 60:384-95; Millward et al. (2013) Integr Biol (Camb) 5(1):87-95), Lallana et al. (2012) Pharm Res 29(1):1-34, Gregoritza et al. (2015) Eur J Pharm Biopharm. 97(Pt B):438-453, Musumeci et al. (2015) Curr Med Chem. 22(17):2022-2050, McKay et al. (2014) Chem Biol 21(9):1075-1101, Ulrich et al. (2014) Chemistry 20(1):34-41, Pasini (2013) Molecules 18(8):9512-9530, and Wangler et al. (2010) Curr Med Chem. 17(11):1092-1116; herein incorporated by reference in their entireties.

Pharmaceutical Compositions

Nanoparticles, as described herein, can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the nanoparticles or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the nanoparticles (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising nanoparticles are in unit dosage form, meaning an amount of a composition appropriate for a single dose, in a premeasured or prepackaged form.

The compositions herein may optionally include one or more additional agents, such as antibiotics, adjuvants, immunostimulatory agents, vaccines, and/or other medications used to treat a subject for an infection. Compounded preparations may include nanoparticles and one or more other agents for treating an infection, such as, but not limited to, antibiotics including broad spectrum, bactericidal, or bacteriostatic antibiotics such as penicillins including penicillin G, penicillin V, procaine penicillin, benzathine penicillin, veetids (Pen-Vee-K), piperacillin, pipracil, pfizerpen, temocillin, negaban, ticarcillin, and Ticar; penicillin combinations such as amoxicillin/clavulanate, augmentin, ampicillin/sulbactam, unasyn, piperacillin/tazobactam, zosyn, ticarcillin/clavulanate, and timentin; tetacyclines such as chlortetracycline, doxycycline, demeclocycline, eravacycline, lymecycline, meclocycline, methacycline, minocycline, omadacycline, oxytetracycline, rolitetracycline, sarecycline, tetracycline, and tigecycline; cephalosporins such as cefacetrile (cephacetrile), cefadroxil (cefadroxyl; duricef), cefalexin (cephalexin; keflex), cefaloglycin (cephaloglycin), cefalonium (cephalonium), cefaloridine (cephaloradine), cefalotin (cephalothin; keflin), cefapirin (cephapirin; cefadryl), cefatrizine, cefazaflur, cefazedone, cefazolin (cephazolin; ancef, kefzol), cefradine (cephradine; velosef), cefroxadine, ceftezole, cefaclor (ceclor, distaclor, keflor, raniclor), cefonicid (monocid), cefprozil (cefproxil; cefzil), cefuroxime (zefu, zinnat, zinacef, ceftin, biofuroksym, xorimax), cefuzonam, loracarbef (lorabid) cefbuperazone, cefmetazole (zefazone), cefminox, cefotetan (cefotan), cefoxitin (mefoxin), cefotiam (pansporin), cefcapene, cefdaloxime, cefdinir (sefdin, zinir, omnicef, kefnir), cefditoren, cefetamet, cefixime (fixx, zifi, suprax), cefmenoxime, cefodizime, cefotaxime (claforan), cefovecin (convenia), cefpimizole, cefpodoxime (vantin, pecef, simplicef), cefteram, ceftamere (enshort), ceftibuten (cedax), ceftiofur (naxcel, excenel), ceftiolene, ceftizoxime (cefizox), ceftriaxone (rocephin), cefoperazone (cefobid), ceftazidime (meezat, fortum, fortaz), latamoxef (moxalactam), cefclidine, cefepime (maxipime), cefluprenam, cefoselis, cefozopran, cefpirome (cefrom), cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; quinolones/fluoroquinolones such as flumequine (Flubactin), oxolinic acid (Uroxin), rosoxacin (Eradacil), cinoxacin (Cinobac), nalidixic acid (NegGam, Wintomylon), piromidic acid (Panacid), pipemidic acid (Dolcol), ciprofloxacin (Zoxan, Ciprobay, Cipro, Ciproxin), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), enoxacin (Enroxil, Penetrex), balofloxacin (Baloxin), grepafloxacin (Raxar), levofloxacin (Cravit, Levaquin), pazufloxacin (Pasil, Pazucross), sparfloxacin (Zagam), temafloxacin (Omniflox), tosufloxacin (Ozex, Tosacin), clinafloxacin, gatifloxacin (Zigat, Tequin, Zymar-ophthalmic), moxifloxacin (Avelox, Vigamox), sitafloxacin (Gracevit), prulifloxacin (Quisnon), besifloxacin (Besivance), delafloxacin (Baxdela), gemifloxacin (Factive) and trovafloxacin (Trovan), ozenoxacin, danofloxacin (Advocin, Advocid), difloxacin (Dicural, Vetequinon), enrofloxacin (Baytril), ibafloxacin (Ibaflin), marbofloxacin (Marbocyl, Zenequin), orbifloxacin (Orbax, Victas), and sarafloxacin (Floxasol, Saraflox, Sarafin); macrolides such as azithromycin, clarithromycin, erythromycin, fidaxomicin, telithromycin, carbomycin A, josamycin, kitasamycin, midecamycin/midecamycin acetate, oleandomycin, solithromycin, spiramycin, troleandomycin, tylosin/tylocine, roxithromycin, telithromycin, cethromycin, solithromycin, tacrolimus, pimecrolimus, sirolimus, amphotericin B, nystatin, and cruentaren; sulfonamides such as sulfonamide, sulfacetamide, sulfadiazine, sulfadimidine, sulfafurazole (sulfisoxazole), sulfisomidine (sulfaisodimidine), sulfamethoxazole, sulfamoxole, sulfanitran, sulfadimethoxine, sulfamethoxypyridazine, sulfametoxydiazine, sulfadoxine, sulfametopyrazine, and terephtyl; aminoglycosides such as kanamycin A, amikacin, tobramycin, dibekacin, gentamicin, sisomicin, netilmicin, neomycins B, C, neomycin E (paromomycin), streptomycin, plazomicin, amikin, garamycin, kantrex, neo-fradin, netromycin, nebcin, humatin, spectinomycin (Bs), and trobicin; carbapenems such as imipenem, meropenem, ertapenem, doripenem, panipenem/betamipron, biapenem, tebipenem, razupenem (PZ-601), lenapenem, tomopenem, and thienamycin (thienpenem); ansamycins such as geldanamycin, herbimycin, rifaximin, and xifaxan; carbacephems such as loracarbef and lorabid; carbapenems such as ertapenem, invanz, doripenem, doribax, imipenem/cilastatin, primaxin, meropenem, and merrem; glycopeptides such as teicoplanin, targocid, vancomycin, vancocin, telavancin, vibativ, dalbavancin, dalvance, oritavancin, and orbactiv; lincosamides such as clindamycin, cleocin, lincomycin, and lincocin; lipopeptides such as daptomycin and cubicin; macrolides such as azithromycin, zithromax, surnamed, xithrone, clarithromycin, biaxin, dirithromycin, dynabac, erythromycin, erythocin, erythroped, roxithromycin, troleandomycin, tao, telithromycin, ketek, spiramycin, and rovamycine; monobactams such as aztreonam and azactam; nitrofurans such as furazolidone, furoxone, nitrofurantoin, macrodantin, and macrobid; oxazolidinones such as linezolid, zyvox, vrsa, posizolid, radezolid, and torezolid; polypeptides such as bacitracin, colistin, coly-mycin-S, and polymyxin B; drugs against mycobacteria such as clofazimine, lamprene, dapsone, avlosulfon, capreomycin, capastat, cycloserine, seromycin, ethambutol, myambutol, ethionamide, trecator, isoniazid, I.N.H., pyrazinamide, aldinamide, rifampicin, rifadin, rimactane, rifabutin, mycobutin, rifapentine, priftin, and streptomycin; and other antibiotics such as arsphenamine, salvarsan, chloramphenicol, chloromycetin, fosfomycin, monurol, monuril, fusidic acid, fucidin, metronidazole, flagyl, mupirocin, bactroban, platensimycin, quinupristin/dalfopristin, synercid, thiamphenicol, tigecycline, tigacyl, tinidazole, tindamax fasigyn, trimethoprim, proloprim, and trimpex; adjuvants, including aluminum salts (alum), such as aluminum hydroxide, aluminum phosphate, aluminum sulfate, etc.; oil-in-water emulsion formulations; (saponin adjuvants; Complete Freund's Adjuvant (CFA) and Incomplete Freund's Adjuvant (IFA); cytokines, such as interleukins (IL-1, IL-2, IL-4, IL-5, IL-6, IL-7, IL-12, interferons, macrophage colony stimulating factor (M-CSF), tumor necrosis factor (TNF), etc.; detoxified mutants of a bacterial ADP-ribosylating toxin such as a cholera toxin (CT), pertussis toxin (PT), or an *E. coli* heat-labile toxin (LT); oligonucleotides comprising CpG motifs; as well as other immunostimulatory molecules; and vaccines against bacteria and infectious diseases, including any vaccine comprising bacterial antigenic proteins or attenuated or dead bacteria and, optionally, adjuvants for boosting an immune response against bacteria, such as vaccines against tuberculosis, diphtheria, tetanus, pertussis, *Haemophilus influenzae* type B, cholera, typhoid, *Streptococcus pneumoniae*, and the like.

Alternatively, such agents can be contained in a separate composition from the composition comprising the nanoparticles and co-administered concurrently, before, or after the composition comprising the nanoparticles.

Administration

At least one therapeutically effective cycle of treatment with a composition comprising nanoparticles, as described herein, will be administered to a subject for treatment of a bacterial infection. Bacterial infections that can be treated by the methods described herein include bacterial infections caused by Gram negative bacteria such as, but not limited to, *Acinetobacter* (e.g., *Acinetobacter baumannii*), *Actinobacillus*, *Bordetella*, *Brucella*, *Campylobacter*, *Cyanobacteria*, *Enterobacter* (e.g., *Enterobacter cloacae*), *Erwinia*, *Escherichia coli*, *Franciscella*, *Helicobacter* (*Helicobacter pylori*), *Hemophilus* (e.g., *Hemophilus influenzae*), *Klebsiella* (e.g., *Klebsiella pneumoniae*), *Legionella* (e.g., *Legionella pneumophila*), *Moraxella* (e.g., *Moraxella catarrhalis*), *Neisseria* (e.g., *Neisseria gonorrhoeae*, *Neisseria meningitidis*), *Pasteurella*, *Proteus* (e.g., *Proteus mirabilis*), *Pseudomonas* (e.g., *Pseudomonas aeruginosa*), *Salmonella* (e.g., *Salmonella enteritidis*, *Salmonella typhi*), *Serratia* (e.g., *Serratia marcescens*), *Shigella*, *Treponema*, *Vibrio* (e.g., *Vibrio cholerae*), and *Yersinia* (e.g., *Yersinia pestis*), as well as Gram positive bacteria such as, but not limited to, Actinobacteria, such as *Actinomyces* (e.g., *Actinomyces israelii*), *Arthrobacter*, *Bifidobacterium*, *Corynebacterium* (e.g., *Corynebacterium diphtheriae*), *Frankia*, *Micrococcus*, *Micromonospora*, *Mycobacterium* (e.g., *Mycobacterium tuberculosis*, *Mycobacterium leprae*), *Nocardia*, *Propionibacterium*, and *Streptomyces*; Firmicutes, such as *Bacilli*, order Bacillales including *Bacillus*, *Listeria* (e.g., *Listeria monocytogenes*), and *Staphylococcus* (e.g., *Staphylococcus aureus*, *Staphylococcus epidermidis*), *Bacilli* (e.g., *Bacilli anthracis*, *Bacilli cereus*), order Lactobacillales, including *Enterococcus*, *Lactobacillus*, *Lactococcus*, *Leuconostoc*, *Pediococcus*, and *Streptococcus* (e.g., *Streptococcus pneumoniae*, *Streptococcus mutans*, *Streptococcus sanguinis*, *Streptococcus pyogenes*), Clostridia (e.g., Clostridioides *difficile*, *Clostridium perfringens*, *Clostridium botulinum*, *Clostridium tetani*, *Clostridium sordellii*), including *Acetobacterium*, *Clostridium*, *Eubacterium*, *Heliobacterium*, *Heliospirillum*, *Megasphaera*, *Pectinatus*, *Selenomonas*, *Zymophilus*, and *Sporomusa*, Mollicutes, including *Mycoplasma* (e.g., *Mycoplasma pneumoniae*), *Spiroplasma*, *Ureaplasma*, and *Erysipelothrix*.

In certain embodiments, the subject undergoing treatment with nanoparticles, as described herein, has an infection including, without limitation, an ear infection, a cutaneous infection, a lung infection, a catheter-associated urinary tract infection, a gastrointestinal infection, chronic suppurative otitis media (CSOM), an infection associated with cystic fibrosis, tuberculosis, or an infection in a wound. In some embodiments, the infection is associated with formation of a bacterial biofilm in the subject. In certain embodiments, the infection comprises pathogenic bacteria that are resistant to one or more antibiotics. In some embodiments, the subject has previously been treated for the infection with one or more antibiotics that have not successfully cleared the infection. In some embodiments, the infection is a chronic infection.

By "therapeutically effective dose or amount" of nanoparticles is intended an amount that, when administered alone or in combination with an antibiotic, as described herein, brings about a positive therapeutic response, such as improved recovery from an infection, including any infection caused by Gram-positive or Gram-negative bacteria. Additionally, a therapeutically effective dose or amount may eradicate persister cells as well as other bacterial cells, including planktonic bacteria and bacteria in biofilms. The exact amount required will vary from subject to subject, depending on the species, age, and general condition of the subject, the severity of the condition being treated, the particular type of nanoparticles and their functionalization, other antimicrobial agents or drugs employed in combination, the mode of administration, and the like. An appropriate "effective" amount in any individual case may be determined by one of ordinary skill in the art using routine experimentation, based upon the information provided herein.

In certain embodiments, multiple therapeutically effective doses of compositions comprising nanoparticles, and/or one or more other therapeutic agents, such as antibiotics, adjuvants, immunostimulatory agents, vaccines, and/or other drugs for treating an infection, or other medications will be administered. The compositions comprising nanoparticles are typically, although not necessarily, administered orally, via injection (subcutaneously, intravenously, or intramuscularly), by infusion, topically, or locally. Additional modes of administration are also contemplated, such as intra-arterial, intravascular, pulmonary, intralesional, intraparenchymatous, rectal, transdermal, transmucosal, intrathecal, intraocular, intraperitoneal, and so forth.

The preparations according to the invention are also suitable for local treatment. For example, compositions comprising nanoparticles may be administered directly to the site of infected tissue. The particular preparation and appropriate method of administration can be chosen to target the nanoparticles to sites of chronic infection and sites of bacterial biofilms where persister cells typically reside and require eradication.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising nanoparticles and/or other agents may be administered using the same or different routes of administration in accordance with any medically acceptable method known in the art.

In another embodiment, the pharmaceutical compositions comprising nanoparticles and/or other agents are administered prophylactically, e.g., to prevent infection. Such prophylactic uses will be of particular value for subjects who are immunodeficient, patients who have been treated with immunosuppressive agents, or who have a genetic predisposition or disease (e.g., acquired immunodeficiency syndrome (AIDS), cancer, diabetes, or cystic fibrosis) that makes them prone to developing infections.

In another embodiment, the pharmaceutical compositions comprising nanoparticles and/or antibiotics, and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

Those of ordinary skill in the art will appreciate which conditions the nanoparticles can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

In certain embodiments, multiple therapeutically effective doses of a composition comprising nanoparticles will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, once a week, every other week, and so forth. For example, in some embodiments, a composition comprising nanoparticles will be administered once-weekly, twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., once-weekly, twice-weekly or thrice-weekly administration of a therapeutically effective dose) for one or more weekly cycles until the desired therapeutic response is achieved. The agents can be administered by any acceptable route of administration as noted herein below. The amount administered will depend on the potency of the nanoparticle and its type of functionalization, the magnitude of the effect desired, and the route of administration.

Nanoparticles (again, preferably provided as part of a pharmaceutical preparation) can be administered alone or in combination with one or more other therapeutic agents, such as other agents for treating an infection, including, but not limited to, antibiotics including broad spectrum, bactericidal, or bacteriostatic antibiotics such as penicillins including penicillin G, penicillin V, procaine penicillin, benzathine penicillin, veetids (Pen-Vee-K), piperacillin, pipracil, pfizerpen, temocillin, negaban, ticarcillin, and Ticar; penicillin combinations such as amoxicillin/clavulanate, augmentin, ampicillin/sulbactam, unasyn, piperacillin/tazobactam, zosyn, ticarcillin/clavulanate, and timentin; tetacyclines such as chlortetracycline, doxycycline, demeclocycline, eravacycline, lymecycline, meclocycline, methacycline, minocycline, omadacycline, oxytetracycline, rolitetracycline, sarecycline, tetracycline, and tigecycline; cephalosporins such as cefacetrile (cephacetrile), cefadroxil (cefadroxyl; duricef), cefalexin (cephalexin; keflex), cefaloglycin (cephaloglycin), cefalonium (cephalonium), cefaloridine (cephaloradine), cefalotin (cephalothin; keflin), cefapirin (cephapirin; cefadryl), cefatrizine, cefazaflur, cefazedone, cefazolin (cephazolin; ancef, kefzol), cefradine (cephradine; velosef), cefroxadine, ceftezole, cefaclor (ceclor, distaclor, keflor, raniclor), cefonicid (monocid), cefprozil (cefproxil; cefzil), cefuroxime (zefu, zinnat, zinacef, ceftin, biofuroksym, xorimax), cefuzonam, loracarbef (lorabid) cefbuperazone, cefmetazole (zefazone), cefminox, cefotetan (cefotan), cefoxitin (mefoxin), cefotiam (pansporin), cefcapene, cefdaloxime, cefdinir (sefdin, zinir, omnicef, kefnir), cefditoren, cefetamet, cefixime (fixx, zifi, suprax), cefmenoxime, cefodizime, cefotaxime (claforan), cefovecin (convenia), cefpimizole, cefpodoxime (vantin, pecef, simplicef), cefteram, ceftamere (enshort), ceftibuten (cedax), ceftiofur (naxcel, excenel), ceftiolene, ceftizoxime (cefizox), ceftriaxone (rocephin), cefoperazone (cefobid), ceftazidime (meezat, fortum, fortaz), latamoxef (moxalactam), cefclidine, cefepime (maxipime), cefluprenam, cefoselis, cefozopran, cefpirome (cefrom), cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; quinolones/fluoroquinolones such as flumequine (Flubactin), oxolinic acid (Uroxin), rosoxacin (Eradacil), cinoxacin (Cinobac), nalidixic acid (NegGam, Wintomylon), piromidic acid (Panacid), pipemidic acid (Dolcol), ciprofloxacin (Zoxan, Ciprobay, Cipro, Ciproxin), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), enoxacin (Enroxil, Penetrex), balofloxacin (Baloxin), grepafloxacin (Raxar), levofloxacin (Cravit, Levaquin), pazufloxacin (Pasil, Pazucross), sparfloxacin (Zagam), temafloxacin (Omniflox), tosufloxacin (Ozex, Tosacin), clinafloxacin, gatifloxacin (Zigat, Tequin, Zymar-ophthalmic), moxifloxacin (Avelox, Vigamox), sitafloxacin (Gracevit), prulifloxacin (Quisnon), besifloxacin (Besivance), delafloxacin (Baxdela), gemifloxacin (Factive) and trovafloxacin (Trovan), ozenoxacin, danofloxacin (Advocin, Advocid), difloxacin (Dicural, Vetequinon), enrofloxacin (Baytril), ibafloxacin (Ibaflin), marbofloxacin (Marbocyl, Zenequin), orbifloxacin (Orbax, Victas), and sarafloxacin (Floxasol, Saraflox, Saraf in); macrolides such as azithromycin, clarithromycin, erythromycin, fidaxomicin, telithromycin, carbomycin A, josamycin, kitasamycin, midecamycin/midecamycin acetate, oleandomycin, solithromycin, spiramycin, troleandomycin, tylosin/tylocine, roxithromycin, telithromycin, cethromycin, solithromycin, tacrolimus, pimecrolimus, sirolimus, amphotericin B, nystatin, and cruentaren; sulfonamides such as sulfonamide, sulfacetamide, sulfadiazine, sulfadimidine, sulfafurazole (sulfisoxazole), sulfisomidine (sulfaisodimidine), sulfamethoxazole, sulfamoxole, sulfanitran, sulfadimethoxine, sulfamethoxypyridazine, sulfametoxydiazine, sulfadoxine, sulfametopyrazine, and terephtyl; aminoglycosides such as kanamycin A, amikacin, tobramycin, dibekacin, gentamicin, sisomicin, netilmicin, neomycins B, C, neomycin E (paromomycin), streptomycin, plazomicin, amikin, garamycin, kantrex, neo-fradin, netromycin, nebcin, humatin, spectinomycin (Bs), and trobicin; carbapenems such as imipenem, meropenem, ertapenem, doripenem, panipenem/betamipron, biapenem, tebipenem, razupenem (PZ-601), lenapenem, tomopenem, and thienamycin (thienpenem); ansamycins such as geldanamycin, herbimycin, rifaximin, and xifaxan; carbacephems such as loracarbef and lorabid; carbapenems such as ertapenem, invanz, doripenem, doribax, imipenem/cilastatin, primaxin, meropenem, and merrem; glycopeptides such as teicoplanin, targocid, vancomycin, vancocin, telavancin, vibativ, dalbavancin, dalvance, oritavancin, and orbactiv; lincosamides such as clindamycin, cleocin, lincomycin, and lincocin; lipopeptides such as daptomycin and cubicin; macrolides such as azithromycin, zithromax, sumamed, xithrone, clarithromycin, biaxin, dirithromycin, dynabac, erythromycin, erythocin, erythroped, roxithromycin, troleandomycin, tao, telithromycin, ketek, spiramycin, and rovamycine; monobactams such as aztreonam and azactam; nitrofurans such as furazolidone, furoxone, nitrofurantoin, macrodantin, and macrobid; oxazolidinones such as linezolid, zyvox, vrsa, posizolid, radezolid, and torezolid; polypeptides such as bacitracin, colistin, coly-mycin-S, and polymyxin B; drugs against mycobacteria such as clofazimine, lamprene, dapsone, avlosulfon, capreomycin, capastat, cycloserine, seromycin, ethambutol, myambutol, ethionamide, trecator, isoniazid, I.N.H., pyrazinamide, aldinamide, rifampicin, rifadin, rimactane, rifabutin, mycobutin, rifapentine, priftin, and streptomycin; and other antibiotics such as arsphenamine, salvarsan, chloramphenicol, chloromycetin, fosfomycin, monurol, monuril, fusidic acid, fucidin, metronidazole, flagyl, mupirocin, bactroban, platensimycin, quinupristin/dalfopristin, synercid, thiamphenicol, tigecycline, tigacyl, tinidazole, tindamax fasigyn, trimethoprim, proloprim, and trimpex; antimicrobial agents that cause DNA damage in bacteria, including quinolones (e.g., ciprofloxacin), beta-lactams (e.g., penicillins, cephalosporins, carbapenems, and monobactams), aminoglycosides (e.g., streptomycin, kanamycin, tobramycin, gentamicin, and neomycin), glycopeptide antibiotics (e.g., bleomycin), lipopeptide antibiotics (e.g., daptomycin), bacteriostatic antibiotics (e.g., chloramphenicol and linezolid), and methyl methanesulfonate; and adjuvants, including aluminum salts (alum), such as aluminum hydroxide, aluminum phosphate, aluminum sulfate, etc.; oil-in-water emulsion formulations; (saponin adjuvants; Complete Freund's Adjuvant (CFA) and Incomplete Freund's Adjuvant (IFA); cytokines, such as interleukins (IL-1, IL-2, IL-4, IL-5, IL-6, IL-7, IL-12, interferons, macrophage colony stimulating factor (M-CSF), tumor necrosis factor (TNF), etc.; detoxified mutants of a bacterial ADP-ribosylating toxin such as a cholera toxin (CT), pertussis toxin (PT), or an *E. coli* heat-labile toxin (LT); oligonucleotides comprising CpG motifs; as well as other immunostimulatory molecules; and vaccines such as vaccines against tuberculosis, diphtheria, tetanus, pertussis, *Haemophilus influenzae* type B, cholera, typhoid, and *Streptococcus pneumoniae*, and other vaccines comprising bacterial antigenic proteins or attenuated or dead bacteria for boosting an immune response against bacteria, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

Nanoparticles can be administered prior to, concurrent with, or subsequent to other agents. If provided at the same time as other agents, nanoparticles can be provided in the same or in a different composition. Thus, nanoparticles and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising nanoparticles and a dose of a pharmaceutical composition comprising at least one other agent, such as another drug for treating an infection, which in combination comprise a therapeutically effective dose, according to a particular dosing regimen. Similarly, nanoparticles and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Kits

Kits may comprise one or more containers of the compositions described herein comprising nanoparticles, or reagents for preparing such compositions, and optionally one or more antibiotics for treating a bacterial infection. Compositions can be in liquid form or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can further comprise a container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may also provide a delivery device pre-filled with the functionalized nanoparticles.

In addition to the above components, the subject kits may further include (in certain embodiments) instructions for practicing the subject methods (i.e., instructions for treating a bacterial infection with nanoparticles as described herein). These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), DVD, Blu-ray, flash drive, and the like, on which the information has been recorded. Yet another form of these instructions that may be present is a website address which may be used via the internet to access the information at a removed site.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-52 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A nanoparticle comprising a thiol-binding metallic core conjugated to a fluoroquinolone antibiotic.

2. The nanoparticle of aspect 1, wherein the fluoroquinolone antibiotic is selected from the group consisting of ciprofloxacin, ofloxacin, moxifloxacin, gemifloxacin, levofloxacin, and finafloxacin.
3. The nanoparticle of aspect 2, wherein the fluoroquinolone antibiotic is ciprofloxacin.
4. The nanoparticle of aspect 3, wherein the thiol-binding metallic core is conjugated to 47 ciprofloxacin molecules
5. The nanoparticle of aspect 3 or 4, wherein the ciprofloxacin is conjugated to the thiol-binding metallic core through a bond between an amino group of the ciprofloxacin and a metal atom of the metallic core.
6. The nanoparticle of any one of aspects 1 to 5, wherein the thiol-binding metallic core comprises one or more of gold, silver, nickel, copper, aluminum, or cobalt, or an oxide, carbide, nitride, or alloy thereof.
7. The nanoparticle of any one of aspects 1 to 6, wherein the metallic core has a diameter of less than 10 nm.
8. The nanoparticle of aspect 7, wherein the diameter ranges from about 1 nm to about 5 nm.
9. The nanoparticle of aspect 8, wherein the diameter is about 4 nm.
10. The nanoparticle of any one of aspects 1 to 9, further comprising an anionic moiety attached to the outer surface of the nanoparticle.
11. The nanoparticle of any one of aspects 1 to 10, further comprising a cell penetrating peptide attached to the outer surface of the nanoparticle.
12. The nanoparticle of aspect 11, wherein the cell-penetrating peptide is a human immunodeficiency virus (HIV) trans-activator of transcription (TAT) cell-penetrating peptide
13. The nanoparticle of aspect 12, wherein the TAT cell-penetrating peptide comprises the amino acid sequence of SEQ ID NO:7.
14. The nanoparticle of any one of aspects 1 to 13, further comprising an anionic moiety attached to the outer surface of the nanoparticle.
15. The nanoparticle of aspect 14, wherein the anionic moiety comprises a carboxylate functional group, a phosphate functional group, or a sulfate functional group.
16. The nanoparticle of any one of aspects 1 to 15, further comprising a polyethylene glycol (PEG) polymer, wherein the PEG polymer is attached to the outer surface of the nanoparticle.
17. The nanoparticle of aspect 16, wherein the PEG polymer is functionalized with the anionic moiety.
18. The nanoparticle of aspect 17, wherein the PEG polymer is polyethylene glycol carboxylic acid (PEG-COOH) or thiol-carboxyl polyethylene glycol (COOH-PEG-SH).
19. The nanoparticle of any one of aspects 1 to 18, further comprising an antimicrobial agent having bactericidal activity against persister cells or bacteria residing in biofilms, wherein the antimicrobial agent is attached to the outer surface of the nanoparticle.
20. The nanoparticle of aspect 19, wherein the antimicrobial agent is a D-carbohydrate, a D-amino acid, or a nucleic acid comprising a CrcZ RNA sequence or a CrcZ A-rich motif sequence.
21. The nanoparticle of aspect 20, wherein the CrcZ RNA sequence comprises:
   a) a nucleotide sequence of SEQ ID NO:1;
   b) a nucleotide sequence having at least 90% identity to the sequence of SEQ ID NO:1, wherein the nanoparticle is capable of rendering a persister cell susceptible to an antibiotic; or
   c) an RNA equivalent of a) or b).
22. The nanoparticle of aspect 20, wherein the CrcZ A-rich motif sequence comprises:

| | | |
|---|---|---|
| a) | ACAACAACAATAACAA; | (SEQ ID NO: 2) |
| b) | CAATAAGAA; | |
| c) | AACAAGAACAA; | (SEQ ID NO: 3) |
| d) | AGAACAACAAAA; | (SEQ ID NO: 4) |
| e) | ACAACAAGAACAA; | (SEQ ID NO: 5) |
| f) | AGAACAAGAACAA; | (SEQ ID NO: 6) |
| g) | AACAACAA; | |
| h) | AAAAACAA; | |
| or | | |
| i) | an RNA equivalent of a)-i). | |

23. The nanoparticle of any one of aspects 1 to 22, wherein the nanoparticle further comprises a linker connecting the antimicrobial agent or the cell penetrating peptide to the outer surface of the nanoparticle.
24. The nanoparticle of any one of aspects 1 to 23, wherein the nanoparticle is biocompatible with human cells.
25. The nanoparticle of any one of aspects 1 to 24, further comprising a nucleotide, wherein the nucleotide is conjugated to the thiol-binding metallic core.
26. The nanoparticle of aspect 25, wherein the nucleotide is adenosine triphosphate (ATP), adenosine monophosphate (AMP), adenosine diphosphate (ADP), or a phosphorothioate analog, deoxyribonucleotide analog, a 7-deaza purine nucleotide analog, or a phosphomethylphosphonic acid adenylate ester thereof.
27. The nanoparticle of aspect 26, wherein the phosphorothioate analog is ATPαS, ATPβS, ATPγS, ADPαS, ADPβS, or AMPS.
28. The nanoparticle of aspect 26, wherein the deoxyribonucleotide analog is deoxyadenosine monophosphate (dAMP), deoxyadenosine diphosphate (dADP), or deoxyadenosine triphosphate (dATP).
29. The nanoparticle of aspect 26, wherein the 7-deaza purine nucleotide analog is 7-deazaadenosine-5'-triphosphate (7-deaza-ATP).
30. The nanoparticle of aspect 26, wherein the phosphomethylphosphonic acid adenylate ester is β,γ-methyleneadenosine 5'-triphosphate (AMP-PCP).
31. A composition for treating an infection comprising the nanoparticle of any one of aspects 1 to 30.
32. The composition of aspect 31, further comprising a pharmaceutically acceptable excipient or carrier.
33. A method of treating an infection in a subject, the method comprising administering a therapeutically effective amount of the composition of aspect 31 or 32 to the subject.

34. The method of aspect 33, further comprising administering a therapeutically effective amount of at least one antibiotic in combination with the composition.
35. The method of aspect 33 or 34, wherein the subject has a chronic infection.
36. The method of aspect 35, wherein the infection is an ear infection, a cutaneous infection, a lung infection, a catheter-associated urinary tract infection, or a gastrointestinal infection.
37. The method of any one of aspects 33 to 36, wherein the infection is associated with formation of a bacterial biofilm in the subject.
38. The method of aspect 37, wherein the biofilm is in a chronic wound in the subject.
39. The method of any one of aspects 33 to 38, wherein the subject has chronic suppurative otitis media (CSOM), cystic fibrosis, or tuberculosis.
40. The method of any one of aspects 33 to 39, wherein the infection comprises pathogenic bacteria that are resistant to one or more antibiotics.
41. The method of any one of aspects 33 to 40, wherein the subject has previously been treated for the infection with one or more antibiotics that have not successfully cleared the infection.
42. The method of any one of aspects 33 to 41, wherein said treating eradicates all or most biofilm bacteria and planktonic bacteria.
43. The method of any one of aspects 33 to 42, wherein said treating eradicates all or most persister cells.
44. The method of aspect 43, wherein the persister cells are in a biofilm or are internalized by a macrophage.
45. The method of aspect 43 or 44, wherein the persister cells are multidrug tolerant persister cells.
46. The method of any of aspects 43 to 45, wherein the persister cells comprise Gram-negative or Gram-positive bacteria.
47. The method of aspect 46, wherein the persister cells comprise *Pseudomonas aeruginosa*.
48. The method of any one of aspects 33 to 47, wherein multiple cycles of treatment are administered to the subject.
49. The method of any one of aspects 33 to 48, wherein the composition is administered intravenously, subcutaneously, by inhalation, or topically.
50. The method of any one of aspects 33 to 49, wherein the composition is administered locally at the site of infected tissue.
51. The method of aspect 50, wherein the infection is an ear infection, and the composition is administered locally into the ear canal.
52. The method of any one of aspects 33 to 51, wherein the infection is a *Pseudomonas* infection in a subject who has cystic fibrosis.
53. A kit comprising the nanoparticle of any one of aspects 1 to 30 and instructions for treating a bacterial infection.
54. A method of eradicating bacteria in a biofilm, the method comprising contacting the biofilm with an effective amount of the nanoparticle of any one of aspects 1 to 30.
55. The method of aspect 54, further comprising contacting the biofilm with an effective amount of at least one antibiotic.
56. The method of aspect 54 or 55, wherein the biofilm is on a medical device, a personal hygiene article, toiletry, cosmetic, disinfectant, cleaning solution, or in a water treatment or distribution system.
57. A method of eradicating dormant bacteria comprising persister cells, the method comprising contacting the dormant bacteria with an effective amount of the nanoparticle of any one of aspects 1 to 30.
58. The method of aspect 57, further comprising contacting the dormant bacteria with an effective amount of at least one antibiotic.
59. The method of aspect 57 or 58, wherein the dormant bacteria are in a biofilm, in a liquid culture, or on an inanimate surface.
60. A method of killing fluoroquinolone-resistant bacteria, the method comprising contacting the fluoroquinolone-resistant bacteria with the nanoparticle of any one of aspects 1 to 30.
61. A method of increasing production of oxygen species (ROS) in a macrophage infected with persister bacteria, the method comprising contacting the macrophage with an effective amount of the nanoparticle of any one of aspects 1 to 30.
62. A method of increasing autophagy in a macrophage infected with persister bacteria, the method comprising contacting the macrophage with an effective amount of the nanoparticle of any one of aspects 1 to 30.

A method of increasing secretion of tumor necrosis factor-alpha (TNF-α) from a macrophage infected with persister bacteria, the method comprising contacting the macrophage with an effective amount of the nanoparticle of any one of aspects 1 to 30.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Targeting Intracellular Persistent Bacterial Infections and Persister Cells

Chronic bacterial infections are a significant problem in global health. They contribute to a total annual cost in the USA of around $94 billion (2-4). They provide a breeding ground for antimicrobial resistance, accounting for over 700,000 deaths each year, with major world health organizations estimating it could become the leading cause of death by 2050. This has spurred a world-wide call to action by the World Health Organization, the United Nations, the CDC, and many others recognizing the enormous unmet medical need to address antimicrobial resistance. A few examples of chronic bacteria persister cell-associated diseases include cystic fibrosis (CF) lung disease, chronic wounds, and chronic suppurative otitis media (CSOM). *Pseudomonas aeruginosa* (PA) infection in CF patients increases mean health care costs by $18500 annually (5). A lack of cure means infection with resistant strains progresses to end stage lung disease leading to either lung transplant or death. Chronic skin wounds include a wide range of areas, including burns, diabetic ulcers, and post-surgery (6-11). CSOM is a massive global health problem affecting 330 million people worldwide, making it the leading cause of permanent hearing loss in the developing world (12). It predominantly affects lower socioeconomic groups, including immigrants and indigenous populations, with an incidence as high as 45%. (12, 13)

Role of Persister Cells in Chronic Infections

PA is the leading bacterial cause of CSOM, a disease characterized by a chronically infected and discharging middle ear. Perforation of the tympanic membrane (TM), often a result of trauma or an acute middle ear infection, allows bacteria from the external ear canal to invade and colonize the middle ear. Like in other persister cell diseases, bacteria enter the host niche and establish a biofilm "community" of various phenotypes of bacteria, including persister cells within the biofilm (14, 15). Persister cells are metabolically inactive and evade antibiotics, which rely on metabolic mechanisms for effect (16). Repeated treatment with antimicrobials clears metabolically active bacteria converting the infection to inactive. When the surviving persister cells "wake up" and proliferate, the infection is active again (FIG. 1) (17).

Persister Cell Phenotypes are Induced in Times of Stress

Persister cell formation is stimulated under conditions that favor the activation of stress signaling pathways, such as the SOS response for DNA repair in response to sub-lethal concentrations of antibiotics, as well as stochastic activation of the alarmone (p)ppGpp in nutrient starvation during biofilm formation (FIG. 1) (17). In Gram-negative bacteria, like PA, the inner cytoplasmic membrane regulates the proton motive force (PMF) to generate the energy necessary for ATP synthesis by the F1-F0 ATPase (18). Thus, the reduction of PMF in persister cells results in a decrease in intracellular levels of ATP, which in turn leads to a reduction in the activity of energy-dependent targets such as protein synthesis, DNA synthesis, and peptidoglycan synthesis. These findings are the basis of the hypothesis that the ATP level of the cell is predictive of bactericidal antibiotic efficacy and explains bacterial tolerance to antibiotics (19). Although persister cells are metabolically inactive, they still need a minimum energy level (ATP) to stay alive. Therefore, abolishing the PMF by blocking the electron transport chain via the cytoplasmic membrane disruption kills persister cells.

Current Anti-Persister Strategies are Inadequate in Targeting Intracellular Persister Cells.

There are currently four existing strategies against persister cells: (i) Providing an energy source to "wake up" persister cells: Enhancing the efficacy of current antibiotics by shifting the persister metabolism from a quiescent to a replicating state by the addition of metabolites (e.g., mannitol, glucose, fructose, and fumarate) (22, 23). In vivo delivery of metabolite and antibiotic combination at the effective dose in intracellular persister cells is challenging because each component's pharmacokinetics is different. Another roadblock in this approach is that if the persister cells "wake up" in the absence of localized sufficient antibiotic concentrations, it will cause infection exacerbation (24). (ii) Disruption of the persister cell membrane with membrane-active compounds: Bacterial membranes are attractive anti-persister targets because they can be disrupted independently of growth (25-27). Unfortunately, most of these agents also indiscriminately disrupt mammalian membranes. Furthermore, serum binding and tissue penetration are problems intrinsic to membrane-active agents. For example, daptomycin is inactive against respiratory infections, which is thought to be due to high protein binding levels in epithelial lining fluid (28). Commonly associated nephrotoxicity with the membrane-active agents is also a problem. In culture models, the accumulation of oritavancin, an essential drug for killing intracellular *Staphylococcus aureus*, induces a lysosomal lipid storage disorder (29). The narrower safety margin is a roadblock for developing membrane-active agents and could impair clinical applications as anti-persister therapies. (iii) Anti-cancer drug repurposing: Several known anti-cancer drugs were recently shown to possess potent anti-persister activity (30, 31). Although this strategy is potentially advantageous in terms of cost, the considerable side effects of these anti-cancer drugs and their relatively high toxicity could impair clinical applications as anti-persister therapies.

(iv) Inducing reactive oxygen species (ROS) production to increase bactericidal antibiotic potency: Two distinct approaches have been proposed for increasing endogenous ROS concentrations to reach lethal levels. The first approach is an amplification of ROS accumulation via physical and electrochemical methods. Direct interaction of molecular oxygen (02) with light (400-470 nm wavelength) was shown to kill persister cells via ROS generation following photo-excitation of intracellular dyes (photosensitizers) (32). The generation of hydrogen peroxide ($H_2O_2$) by an electrochemical scaffold was shown to enter PA cells and lead to the formation of hydroxyl radicals (HO) (33). Although the ROS generation by physical and electrochemical methods could reach lethal levels, in vivo delivery of sufficient electric current impairs clinical applications as anti-persister therapies. The low penetration of visible light into tissue limits the application to superficial infections. The second approach is to amplify ROS accumulation via the inhibition of ROS protective genes. Mutational studies have demonstrated that bacteria strains with genetic deletions in antioxidants defense are more susceptible to killing by the superoxide radical (02) (generated via menadione), $H_2O_2$, and conventional antibiotics (34). Once a ROS threshold is exceeded, the death process becomes self-driven (i.e., self-sustainable) (35). Although inhibition of ROS-protective genes is attractive, it has proven difficult to obtain molecules that simultaneously inhibit the persister cells' antioxidant defense system and promote HO' production because medicinal chemistry does not generate such multifunctional compounds.

Strategy for Targeting Intracellular Bacterial Persister Cells

We propose a novel strategy for targeting intracellular bacterial persister cells. Persister cells are metabolically inactive (dormant) bacteria that are not targeted by traditional antimicrobial strategies. Thus, persister cells are a primary source of chronic and relapsing bacterial infections because they are not eradicated. Persister cells are able to limit reactive oxygen species (ROS) production in macrophages reducing the bactericidal activity of fluoroquinolones. We therefore developed a novel thiol antioxidant inhibition strategy that promotes hydroxyl radical formation following persister cell treatment with fluoroquinolones. We first approached this strategy by administering an antibiotic adjuvant, anionic functionalized gold nanocluster. We showed PA persister cell eradication in vitro, made fluoroquinolone-resistant bacteria susceptible, and demonstrated efficacy in vivo in our model. We have shown that this strategy is effective against extracellular persister cells. For complete eradication, we must target both extracellular and intracellular persister cells, particularly within host macrophages. To achieve this, we optimized our strategy by combining the drug and adjuvant on a single platform, a ciprofloxacin nanoformulation (AuNC).

When materials acquire the nanosize, they start to behave differently, and novel properties emerge. In contrast to the parent drug ciprofloxacin, AuNC has the following distinct advantages: (1) lowers the minimal inhibitory concentration (MIC) of ciprofloxacin-resistant PA near the ciprofloxacin breakpoint, (2) exhibits the anti-persister activity towards the persister cells generated by ciprofloxacin, (3) stimulates the secretion of tumor necrosis factor-α (TNF-α) involved in the innate defense clearance of PA.

This approach offers a potential cure for CSOM, a disease afflicting 330 million around the world. This new anti-persister strategy has implications for any predominantly PA chronic bacterial infection, including CF and chronic wounds on a grander scale. Beyond that, this approach may be applied to any persister cell bacterial infection, including TB, catheter-associated urinary tract infections, and gastro-intestinal infections (37, 38). This strategy can "rescue" the resistant bacteria's resistance profile, making them again susceptible to traditional therapeutics, and is a significant step in the global effort against antimicrobial resistance development.

Example 2

Hydroxyl Radical Formation to Eradicate Intracellular Persister Cells

The HO· is so reactive that no enzyme system can use it as a substrate. Once generated, the HO· damages DNA, RNA, proteins, and lipids, resulting in cell death. Thiol based antioxidants, especially glutathione and cysteine, are the only defense to protect against HO·. Therefore, a thiol antioxidant inhibition strategy, generation of HO· from endogenous $H_2O_2$, provides the best alternative strategy to kill intracellular persister cells with innocuous $H_2O_2$ levels. Blocking HO· production by iron chelator or quenching HO· with thiourea increased antibiotic-treated bacteria survival (36). We reason that a thiol antioxidant inhibition strategy to amplify endogenous ROS production and catalytic composition of the non-lethal level of $H_2O_2$ into extremely lethal HO· will potentiate both fluoroquinolone and macrophages against intracellular persister cells. No existing antimicrobials use this mode of action. Therefore, we designed and constructed AuNC, an anionic antibiotic composed of a gold core (4 nm) surrounded by 47 ciprofloxacin molecules stabilized via an amino-gold bond.

We explore fluoroquinolone adaptive resistance reversion by destabilizing antioxidant defenses and promoting catalytic decomposition of endogenous $H_2O_2$ to generate HO·. Although inhibition of ROS-protective genes is possible via genetic mutation to make bacterial cells hypersensitive to oxidative attack, the clinical application's main challenge is to find molecules that inhibit the persister cells' antioxidant defense system. Our novel engineered AuNC could inhibit thiol-based antioxidant via the formation of an Au—S bound and generate HO· via the catalytic decomposition of endogenous $H_2O_2$. A key advantage of our approach is that it allows for future application to systemic bacterial infections.

Glutathione depletion can be measured in exposed persister cells. To evaluate the effect of the thiol antioxidant inhibition strategy on glutathione, an Orbitrap ID-X Tribrid Mass Spectrometer System is used to examine if AuNC affects glutathione peroxidase by measuring the GSH/GSSG ratio. We further evaluate catalase and transcription of hydroperoxide reductases during exposure. We use purified OxyR from PA to demonstrate complex formation between OxyR and AuNC and its effect on catalase and hydroperoxide reductase gene expression.

Example 3

Defining the Molecular Mechanism Responsible for Persister Cell Hypersensitivity to the Thiol Antioxidant Inhibition Strategy Our thiol antioxidant inhibition strategy increases ROS accumulation via the depletion of glutathione, catalases, and hydroperoxide reductases. Glutathione (GSH) is a critical thiol molecule in the antioxidant defense of bacteria because it donates its electrons directly to HO·, which leads to glutathione disulfide (GSSG) (39). In vitro tests reveal that GSH and its oxidized form GSSG altered PA's sensitivity of ciprofloxacin by 4-fold (40). Additionally, the lack of GSH contributes to increased sensitivity to ciprofloxacin (41) and $O_2^-$ generating agents (methyl viologen and paraquat) (42, 43). Overall, these results show that PA GSH is critical for protection against oxidative attack and ciprofloxacin.

Nanoscale gold (Au) possesses a strong bonding interaction with GSH and cysteine (the immediate precursor of GSH) (44). Thiol forms strong and thermodynamically favorable covalent bonds with gold (Au—S) compared to amino groups (Au—N) (45). Without being bound by theory, we propose that the AuNC (i.e., ciprofloxacin bound gold nanoparticle via Au—N) may induce GSH depletion, which results from the formation of an Au—S bond occurring in the reaction between the gold core and either GSH or cysteine.

In addition to GSH, OxyR is the central regulator controlling bacterial response to $H_2O_2$. When $H_2O_2$ levels exceed safe limits, OxyR is activated via its two conserved cysteine residues (Cys1999 and Cys208) that react rapidly with $H_2O_2$ to drive the concentration back down to a non-lethal dose (46, 47). Since OxyR acts as an $H_2O_2$ sensor, the formation of Au—S bond between the gold core and cysteine residues from OxyR could impair the oxidation sensing mechanism (i.e., OxyR activation). One would therefore expect that protection against oxidative stress associated with overexpression of either catalases (katA and katB) or alkyl hydroperoxide reductases (ahpB and ahpCF) should be moderate compared to the expression induced by exogenous $H_2O_2$. We hypothesize that AuNC imposes ROS-driven death via a two-step mechanism. First, it destabilizes antioxidant defenses leading to the accumulation of intracellular $H_2O_2$. Subsequently, the catalytic decomposition of $H_2O_2$ into a highly toxic HO· on the surface of AuNC causes persister cell death.

Our Thiol Antioxidant Inhibition Strategy Hypersensitizes PA to Ciprofloxacin $H_2O_2$ contributes causatively to antibiotics lethality (48). $H_2O_2$ is generated as a downstream physiological consequence of antibiotics interacting with their traditional targets. Consequently, when the primary drug target is mutated, fluoroquinolone does not induce significant changes in $H_2O_2$ (48). Thus, the main challenge to reach lethal $H_2O_2$ levels in resistant bacteria is to design molecules that inhibit the antioxidant defense mechanisms. We used two PA strains, including PA01 and extensively drug-resistant (XDR) PA (ID 1674623 from Emery Pharma, Alameda, CA), which is resistant to Cefepime (MIC>32), Ceftazidime (MIC>32), Ciprofloxacin (MIC>8), Gentamicin (MIC>8), Imipenem (MIC>32), PIP/TAZO (MIC>128). The beneficial role of ciprofloxacin nanoformulation (AuNC) over the parent drug ciprofloxacin is demonstrated by the therapeutic window so-called selectivity index (SI=$IC_{50}$/MIC). The higher the SI, the more effective and safe an antibiotic will be during in vivo treatment for a given bacterial infection. SI value increases from 515.7 (parent drug ciprofloxacin) to 1116.7 (AuNC) if PA01 causes the bacterial infection. The SI value increases from 0.6 (parent drug ciprofloxacin) to 13 (AuNC) if PA (XDR) causes the bacterial infection (FIG. 2). Overall, these data suggest that destabilizing antioxidant defenses lead to AuNC-induced hypersensitivity observed in PA01 and PA (XDR). The MIC of PA (XDR) drops close to the ciprofloxacin breakpoint upon nanoformulation (AuNC) (FIG. 2).

Likely Targeting of Antioxidant Systems

Figure 3A:
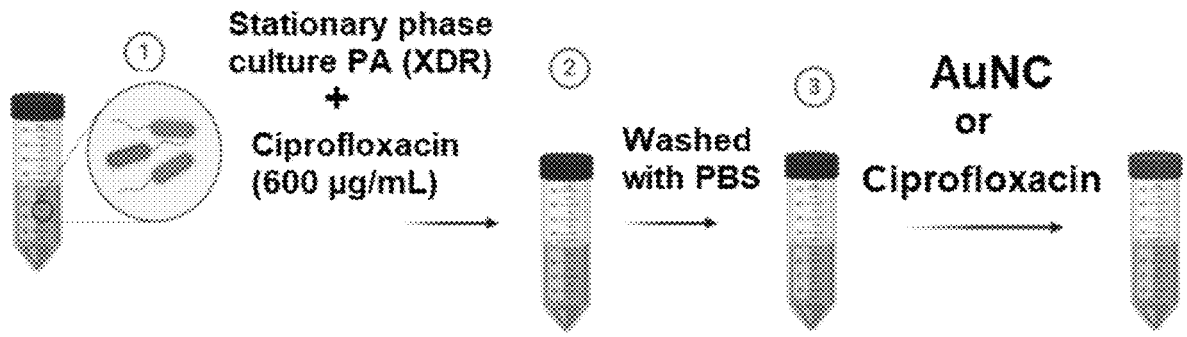
FIGS. 3A-3E. Ciprofloxacin nanoformulation (AuNC) imposes ROS-driven death via destabilization of antioxidant defenses leading to intracellular $H_2O_2$ accumulation. Subsequently, the decomposition of $H_2O_2$ into HO· causes persister cell death. Protocol showing the isolation of persister cells from stationary phase culture of PA (XDR) (FIG. 3A), AuNC eradicates persisters generated by ciprofloxacin, total population (black), isolate persisters level after 600 µg/mL ciprofloxacin (blue), survival persisters after second treatment with ciprofloxacin (3 µg/mL), sterilization of persister with AuNC (3 µg/mL) (FIG. 3B), AuNC enhances fluorescent intensity of $H_2O_2$ sensitive probe (dichlorofluorescin) compared to ciprofloxacin (green) and untreated control (blue) (FIG. 3C), ROS quantification using the area under the curve (AUC) shown that AuNC (red) trigger ROS accumulation 100% above the basal level (blue). While ciprofloxacin only induces 34% ROS accumulation (green) (FIG. 3D), UV-Vis absorption spectra showing that AuNC promotes the catalytic decomposition of $H_2O_2$ to generate HO·, which in turn react with the colorless TMB resulting in the formation of a blue colored product (abs at 652 nm) (FIG. 3E). Data shown reflect mean±SD of three replicates.
Figure 3B:
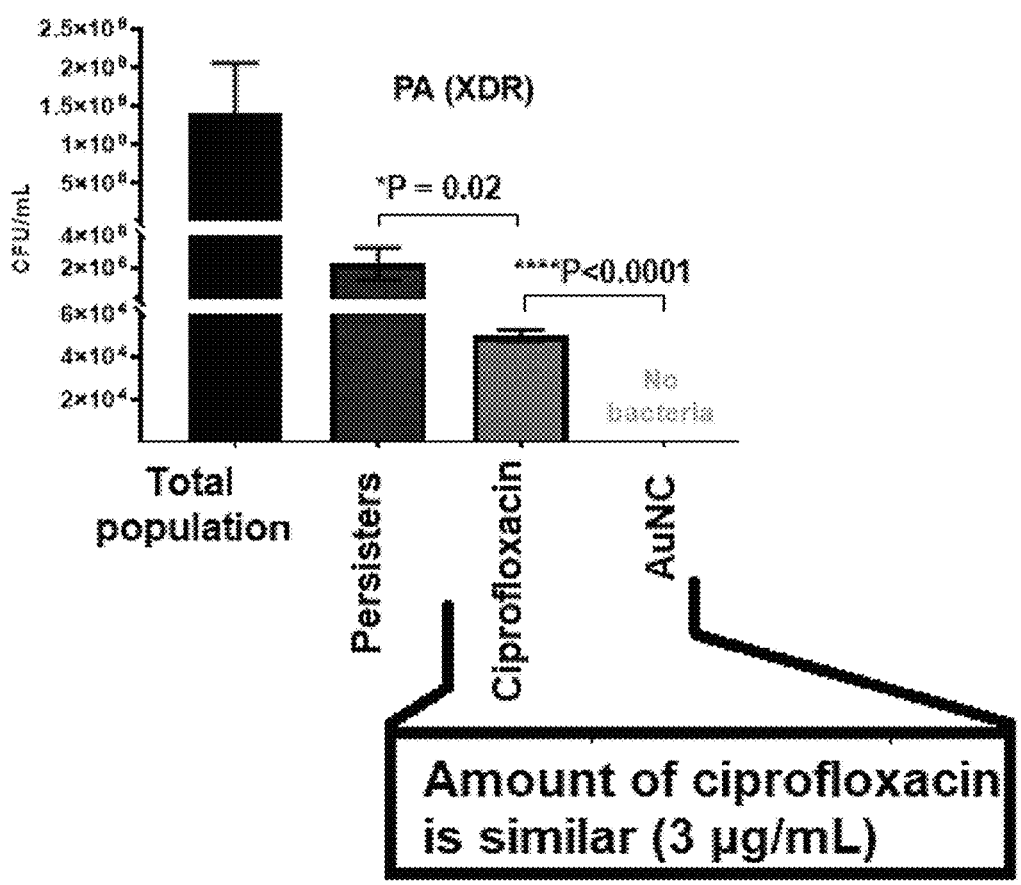
Figure 3C:
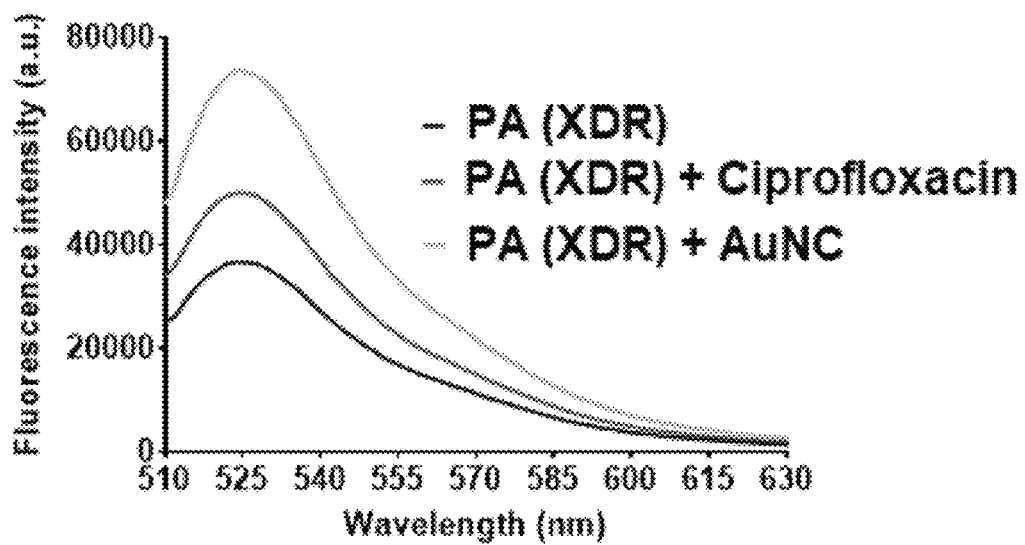
Figure 3D:
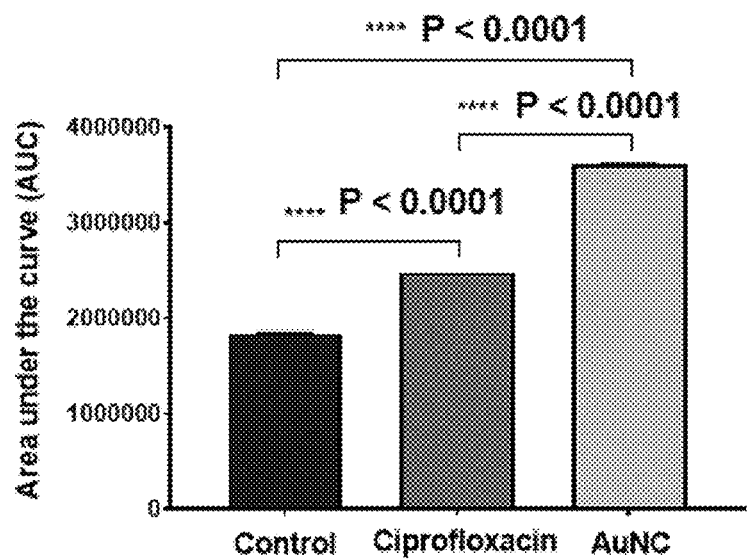

The hypersensitization by AuNC suggests targeting antioxidant systems. We further hypothesized that the thiol antioxidant inhibition strategy might potentiate persister cell killing. We sought to evaluate whether a clinically achievable concentration (i.e., equivalent to unbound human Cmax, 3 µg/mL) could eradicate ciprofloxacin-induced persister cells from PA (XDR). Therefore, ciprofloxacin concentration (i.e., 3 µg/mL) was the same for parent drug ciprofloxacin and AuNC. Ciprofloxacin-induced persister cells were generated by pretreating stationary phase cultures of PA (XDR) with ciprofloxacin (600 µg/mL, 9×MIC) for 24 h. The surviving population of persister cells was washed and suspended in PBS plus AuNC or ciprofloxacin for 24 h (FIG. 3A). After removing the drugs, the surviving bacteria were enumerated. We found that AuNC can eradicate persister cells, whereas parent drug ciprofloxacin fails (FIG. 3B). The steady-state level of $H_2O_2$ inside the unstressed aerobic bacterial cell has been projected to be about 50 nM (47). To assess whether persister cell hypersensitivity triggered by AuNC is linked to $H_2O_2$ accumulation, we quantified the in vivo $H_2O_2$ levels in PA (XDR) cells using an $H_2O_2$ indicator dye, dichlorofluorescin (48-50). The $H_2O_2$ level was quantified by measuring the area under the curve (AUC) (FIGS. 3B, 3C). We found that at a similar ciprofloxacin concentration (0.6 µg/mL), AuNC enhances the fluorescence intensity of $H_2O_2$ indicator dye by 100% over that in untreated PA (XDR) cells (FIG. 3C). Due to the primary drug target mutation in PA (XDR), the parent drug ciprofloxacin only triggered a slight increase of 34% in $H_2O_2$ (FIG. 3C). Together, these results are consistent with the hypothesis that AuNC imposes $H_2O_2$ accumulation via inhibition of the antioxidant defense mechanisms.

Peroxidase (Ahp) is estimated to keep the steady-state concentration of $H_2O_2$ at 50 nM (i.e., basal $H_2O_2$ level) (47). Upon treatment with AuNC (i.e., 0.6 µg/mL of ciprofloxacin), $H_2O_2$ accumulation was 100% higher than the basal level (100 nM of $H_2O_2$), consistent with the observed $H_2O_2$ accumulation in Ahp deficient mutants (51) is similar to the mutant that lacks Ahp. This data further supports the possible role of AuNC as an inhibitor of the antioxidant defense mechanisms. However, even 8 µM intracellular $H_2O_2$ does not produce enough DNA damage to cause death (52). Contrary to $H_2O_2$, the HO strongly affects the survival of persister cells (53).

Figure 3E:
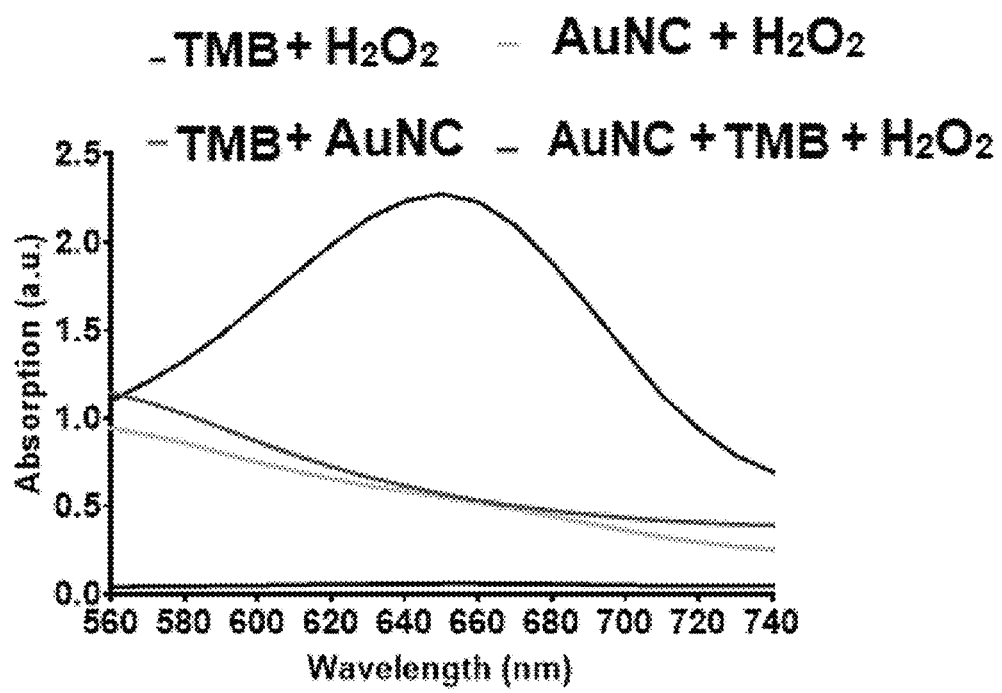

Thus, AuNC may impose ROS-driven death via a two-step mechanism. 1) Destabilizes antioxidant defenses leading to the accumulation of intracellular $H_2O_2$, and 2) the catalytic decomposition of $H_2O_2$ to a highly toxic HO on the surface of AuNC causes persister cell death. To test this hypothesis, we used the chromogenic reaction of 3,3,5,5-tetramethylbenzidine (TMB, colorless) by HO that results in a color change from colorless to blue by converting amino groups to imino groups (54). When AuNC is mixed with $H_2O_2$, in the presence of TMB at pH 7.4, an intense peak appears at 652 nm (blue product) (FIG. 3E). This data confirms the generation of HO that might lead to persister cell death upon treatment with AuNC.

Measuring the Glutathione Depletion in Persister Cells Exposed to the Thiol Antioxidant Inhibition Strategy We use a simultaneous analysis of ROS ($H_2O_2$ and $O_2^-$) and the reduced form of glutathione (GSH) content in persister cells by polychromatic flow cytometry (57). This approach helps study the balance between ROS content and GSH in persister cells receiving different treatments (PBS control, ciprofloxacin, and AuNC) and analyzing the relationship between GSH depletion and persister cell death. The staining is performed with the fluorescent dyes 2',7'-dichlorodihydrofluorescein diacetate ($H_2$DCFH-DA), hydroethidine (HE), and monobromobimane (MBB). MBB binds non-enzymatically with GSH and reacts much more rapidly with GSH than sulfhydryl proteins (58). When excited with a 405-nm violet laser or a UV lamp, MBB becomes fluorescent only after its conjugation with thiols. Thus, the total GSH pool can be detected by flow cytometry by MBB.

To further examine if AuNC affects glutathione peroxidase that catalases $H_2O_2$ by using glutathione, we measure the redox state of the GSH/glutathione disulfide (GSSG) couple in persister cells receiving different treatment (PBS control, ciprofloxacin, and AuNC). The GSH/GSSG ratio will be quantified using Orbitrap ID-X Tribrid Mass Spectrometer System in the Abu-Remaileh lab.

Example 4

Assessment of Complex Formation Between OxyR and AuNC

OxyR protein controls the transcription of catalases (katA and katB) and alkyl hydroperoxide reductases (ahpB and ahpCF) that protect persister cells against $H_2O_2$. We use purified PA OxyR protein to determine the binding affinity (Ka), enthalpy changes (ΔH), and binding stoichiometry (n) of the interaction between OxyR and AuNC using isothermal titration calorimetry (ITC). The syringe is filled with AuNC and the sample cells with OxyR. All ITC measurements are carried out in 50 nM HEPES-NaOH, pH 7.5, 200 mM NaCl, and 2 mM TCEP at 12° C. The binding reaction is started with one injection of 0.5 µL of AuNC to prevent artifacts, followed by 25 injections of 1.56 µL at intervals of 180 s, reaching a final volume of 39.5 µL with a stirring speed of 500 rpm. The reference cell (200 µL) is loaded with water during all experiments, and control titrations are performed to subtract the heat of dilution (i.e., titration of AuNC into the buffer) and mixing for each experiment. Isolation and quantification of PA OxyR protein are carried out using the BSA protein assay (Thermofisher) protocol (59).

TABLE 1

| Genes | qRT-PCR primers (F) | qRT-PCR primers (R) |
|---|---|---|
| ahpB | CCTTGCGTGCTTCGTTCC (SEQ ID NO: 8) | AGACCTCGCCGTGTTCCTC (SEQ ID NO: 9) |
| ahpCF | GCAAGTGGTCGGTCCTGAT (SEQ ID NO: 10) | AGAAGTGGGTGTCGGTGGT (SEQ ID NO: 11) |
| katA | GCGGCTACCTATCGCTACAA (SEQ ID NO: 12) | TCCGGCGAGAAACCGATAC (SEQ ID NO: 13) |
| katB | GAAACAGGTGGCTGAAGTCC (SEQ ID NO: 14) | CGACCTGTTCGGTTTCCTG (SEQ ID NO: 15) |

Example 5

Influence of the Thiol Antioxidant Inhibition Strategy on Macrophage Phagocytic Function
Persister Cells Induced by Macrophages Bacterial infection is met by the host defenses, including white blood cells, to kill the invader, one of which is the macrophage. Bacteria can use host macrophages as a "Trojan Horse" by surviving inside the host cell and changing into a persister cell (20, 21). Thus, intracellular persister cells provide a potential reservoir for recurrent or relapsing infection. The mechanism of persister cell formation in macrophages is still unclear, but it has been suggested that an ATP depletion, induced by macrophages in the bacterial cell, also causes persister cell transformation (21). We evaluate the effect of ketamine (an inhibitor of phagocyte NADPH oxidase activity) on the antimicrobial activity of AuNC and investigate the life cycle of the phagosome and activation of antimicrobial autophagy. We assess the effects of the thiol antioxidant inhibition strategy on phagosome maturation and reduces phagolysosomal leakage. We also examine whether the thiol antioxidant inhibition strategy activates phagocytosis, the mechanism of how macrophages eliminate cytosolic bacteria following phagosome rupture.
The Thiol Antioxidant Inhibition Strategy Improves the Killing of Intracellular Persister Cells We propose that the AuNC thiol antioxidant inhibition improves the killing of PA by restoring autophagy. Without being bound by theory, macrophages can kill engulfed bacteria using different mechanisms that can be activated sequentially, starting with an oxidative burst, which activates autophagy to remove bacteria from the cytosol (60, 61). Upon engulfment, PA first resides in the phagosome, and then following phagosome rupture can be detected in the cytosol (62). Superoxide dismutase (SOD) detoxifies ROS levels, protecting PA killing by macrophages allowing it to survive within the cytosol (63). Therefore, we reasonably presume that the AuNC may improve the killing of cytosolic PA by restoring autophagy.

Figure 5A:
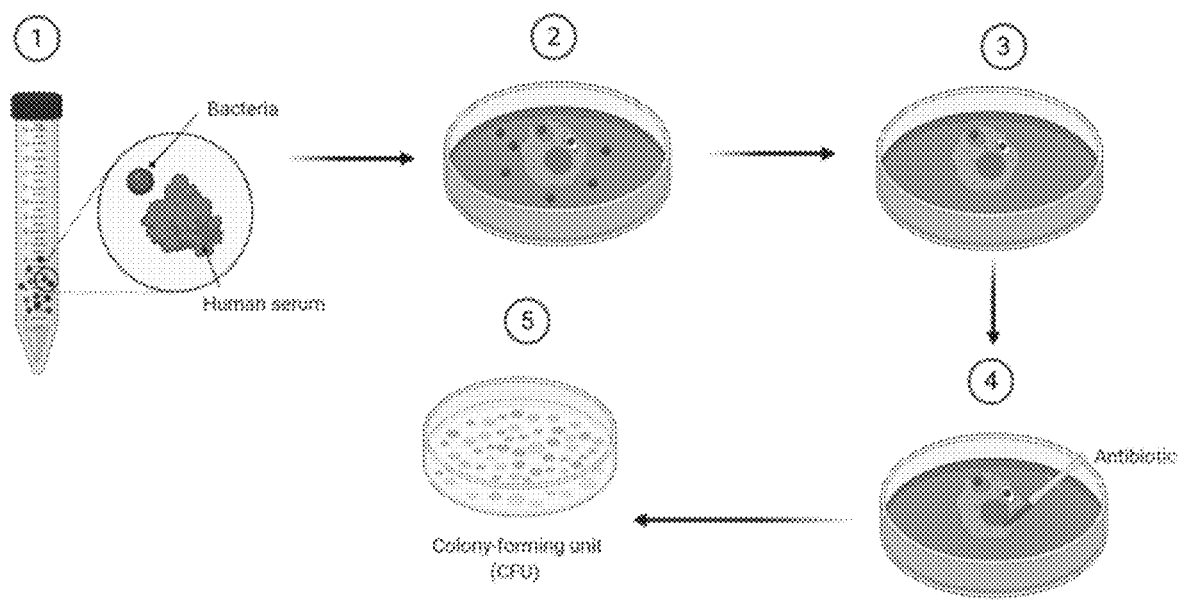
FIGS. 5A-5C. Ciprofloxacin nanoformulation (AuNC) eradicates intra-macrophage PA (XDR). Summary of experimental method (1) incubation of bacteria with 10% human serum in culture medium, (2) incubation of bacteria with cells at MOI of 10, (3) elimination of non-phagocytosed bacteria with 100×MIC gentamicin and elimination of gentamicin by washing, (4) incubation with ciprofloxacin or AuNC for 24 h, (5) determination of residual intracellular bacteria (colony-forming unit CFU) (FIG. 5A), For comparison purposes, the ciprofloxacin concentration was kept the same for parent drug ciprofloxacin and AuNC (i.e., equivalent to the unbound $C_{max}$ 3 µg/mL). Count of intra-macrophage bacteria in untreated RAW 264.7 cells compared to ciprofloxacin demonstrating no significant difference. Whereas, AuNC totally eradicate intracellular persister cells (FIG. 5B). Picture of the representative petri dishes showing no recovery of bacteria after incubation for 72 h (FIG. 5C). Abbreviations: MOI of 10 (multiplicity of infection) MIC (Minimum inhibitory concentration). Data shown reflect mean±SD of three replicates.
Figure 5B:
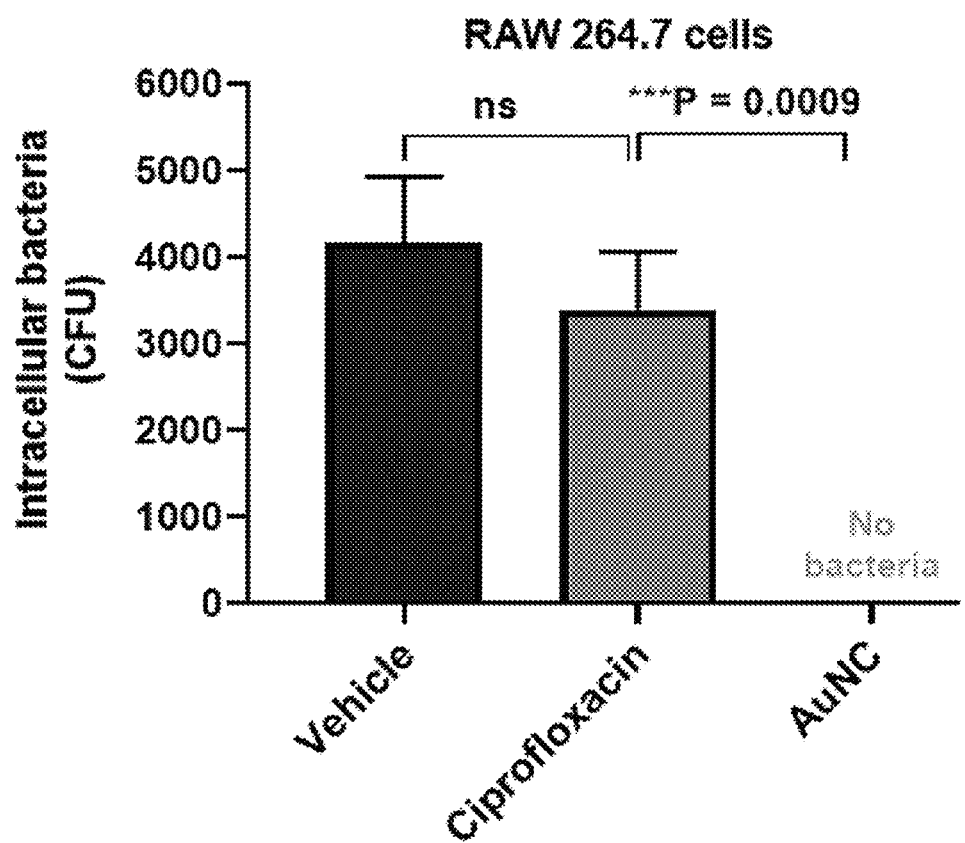
Figure 5C:
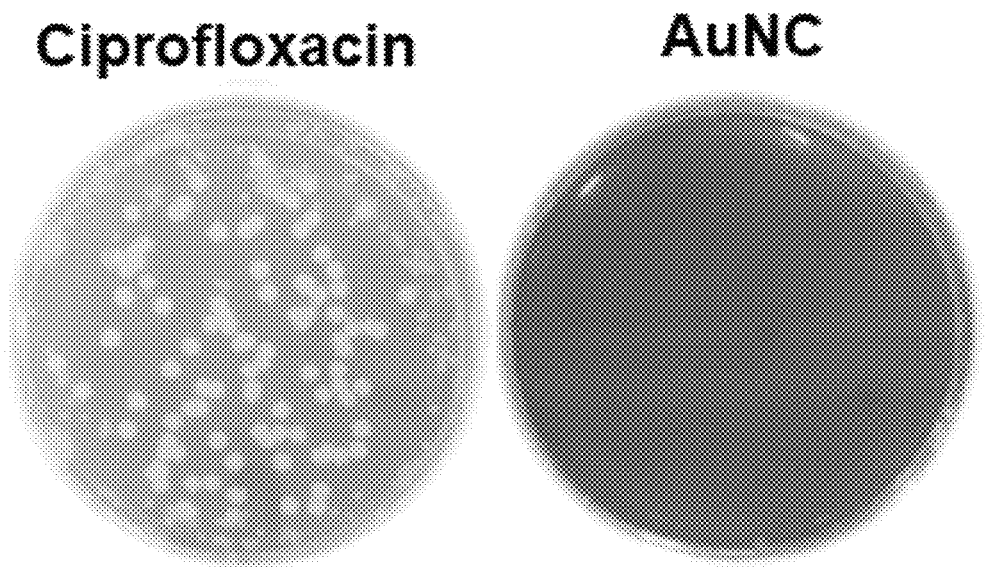

AuNC triggers increased ROS levels, which likely benefits the antimicrobial activity of macrophages. A published 24 h in vitro model of intracellular infection of phagocyte cells with PA was used to demonstrate the superior intracellular antimicrobial activity of AuNC over the parent drug ciprofloxacin (1) (FIG. 5A). For comparison purposes, the ciprofloxacin concentration was kept the same for parent drug ciprofloxacin and AuNC (i.e., equivalent to the unbound $C_{max}$ 3 µg/mL). We found that AuNC eradicates persister cells inside macrophages, whereas the parent drug ciprofloxacin fails (FIGS. 5B, 5C). However, a critical gap exists in our general understanding of how macrophages respond physiologically to the thiol antioxidant inhibition strategy. Here, we will examine how the thiol antioxidant inhibition strategy (i.e., increased ROS levels) contributes to macrophages killing and intracellular persister cell death.
Determining Whether AuNC Facilitates Phagosome Maturation (Phagolysosomes)

Phagosome maturation is when internalized bacteria are trafficked into a series of increasingly acidified environments, resulting in the bacteria's degradation. Phagosome maturation is a complex sequence, and a key event in this process is the progressive acidification of phagosomal lumen (74). According to the standard protocol for measuring phagosomal pH and quantitative immunofluorescence to study phagosome maturation by immunostaining of endogenous organelle markers (LAMP1 and LAMP2) (67, 75, 76), we evaluate the difference in the rate of acidification and maturation of phagosomes containing AuNC versus PA (XDR) at different time points (2 h, 6 h, 12 h, and 24 h) in the phagocytosis assay. For acidic labeling compartments, cells will be stained with Lysotracker Red DND-99 (ThermoFisher Scientific). Uninfected RAW 264.7 cells will be used as a negative control. Positive control Zymosan particles (yeast) (ThermoFisher Scientific).
Determining Whether AuNC Reduces Phagolysosomal Leakage Upon ingestion by macrophages, PA first resides in the phagosome and then escapes phagosomal killing by reducing phagolysosome structural integrity (77). Thus, decreasing phagolysosomal leakage could enhance PA killing in macrophages by either AuNC or macrophages. According to the standard protocol (78), we quantify phagolysosomal leakage triggering by PA, AuNC, and their combination. For combination ingestion, the AuNC are phagocytosed 1 h after internalization of PA (XDR). Porous amorphous 3 µm silica particles is our positive control. RAW 264.7 cells are loaded with 4 kDa FITC-dextran and 4 kDa TRITC dextran, that co-localizes within endolysosomal vesicles, allowing for quantification of phagolysosomal leakage. FITC-dextran fluorescence is quenched in a phagolysosome due to low pH, whereas the TRITC-dextran fluorescence is not affected by pH. Upon phagolysosomal leakage, there is an increase in FITC-dextran fluorescence in the cytoplasm and nuclear area since the FITC-dextran fluorescence is no longer quenched at a higher pH. TRITC-dextran also leaks into the cytoplasm and nucleus, but the quanta of fluorescence are weak compared to FITC-dextran. The nuclear area can be used for the quantification of dextran release. Phagolysosomal leakage can be quantified by drawing an ROI over the nuclear area and by measuring mean pixel intensity for every time point. Images are coded and blinded to group, then prepared by a separate researcher and interpreted by another separate researcher.
Determining Whether AuNC Promotes Activation of Antimicrobial Autophagy Inhibition of antimicrobial autophagy via the reduction of ROS levels is the causal contributor to cytosolic PA's survival (77). Thus, restoring antimicrobial autophagy via AuNC-induced ROS generation could enhance PA killing in macrophages. According to the standard protocol (79, 80), we measure whether autophagy plays a role in the antipersister activity of AuNC observed in FIG. 5B. The autophagy is assessed using immunofluorescence of LC3 and p62, two autophagy biomarkers. Uninfected RAW 264.7 cells are used as a negative control. Positive control is LPS (100 ng/ml) (81).

Evaluating the Capacity of the AuNC to Induce Macrophage Polarization

We evaluate the capacity of the AuNC (dose-dependent effect, the higher dose is 3 µg/mL) to induce the expression of RAW 264.7 cell marker genes of M1 (e.g., iNOS$^+$, CD80$^+$, MHCII$^+$) and M2 (e.g., Arg-1$^+$, CD163$^+$, CD206$^+$) using gene chip analysis and iNOS/Arginase-1 ratio by qPCR (90, 91). Positive controls are for M1 activation (LPS+IFN-γ) and M2 activation (IL4) (92). A negative control is cell medium treatment.

Evaluating the Capacity of the AuNC to Overcome M2 Macrophage Polarization

We also evaluate whether AuNC could repolarize macrophages from M2 to M1 phenotypes by assessing if AuNC can overcome IL4 induced M2 activation. We measure the efficacy of AuNC (3 mg/mL) following topical IL4 administration (200 ng; (93)) in our CSOM mice. We compare to infection in IL4+PBS as a negative control and AuNC only as a positive control.

Example 6

The Role of TNF-α on the Intracellular Antimicrobial Activity of the Thiol Antioxidant Inhibition Strategy Fluoroquinolones are generally considered to have concentration-dependent bactericidal activity. The ratio between the area under the serum concentration-time curve (AUC) and the MIC ratio (AUC/MIC) has been identified as the best predictor of bacterial eradication and bacterial resistance development. AUC/MIC ratio of 100-125 is required for successful bacterial eradication and limiting bacterial resistance development. Due to fluoroquinolone-resistance, which leads to an elevated MIC, most patients with PA infections fail to meet the target threshold of AUC/MIC 100. The combination of direct killing of the bacteria by antibiotics and stimulation of TNF-α to optimize bacterial eradication could solve this problem. In contrast to the parent drug, our AuNC directly kills bacteria at high concentrations (>MIC), while at low concentrations (<MIC), the killing of the remaining bacteria can be mediated by stimulation of the macrophages.

We assess the effect of AuNC induced TNF-α accumulation on NO production by macrophages. After exposure to the thiol antioxidant inhibition strategy, we measure nitric oxide (NO) production and examine the NO synthase (iNOS) potential synergy with AuNC using a selective iNOS inhibitor. To confirm TNF-α promotion in vivo, we measure TNF-α within the middle ear fluid in our CSOM model. To assess whether AuNC-induced TNF-α accumulation skews monocytes toward an M1 phenotype, we evaluate the ability of the AuNC to induce the expression of RAW 264.7 cell marker genes of M1 and M2 using gene chip analysis and qPCR. We also evaluate the repolarization of macrophages from M2 to M1 phenotypes by AuNC. Finally, we evaluate whether M2 activation (IL4) decreases the efficacy of AuNC in our CSOM mice.

Examining the Role of TNF-α on the Intracellular Antimicrobial Activity of the Thiol Antioxidant Inhibition Strategy Stimulation of TNF-α secretion from activated macrophages is an alternative mechanism by which AuNC induces eradication of intracellular persister cells in vivo. Tumor necrosis factor (TNF-α) is best known for its potent pro-inflammatory effects resulting from its ability to enhance the function of macrophages, dendritic cells, B lymphocytes, T lymphocytes, natural killer cells, and other types of immune cells (82). TNF-α enhances macrophage production and also has macrophage differentiation capabilities (83). Previous studies showed that TNFα mediates the control of intracellular infections by stimulating the antimicrobial activity of phagocytes (84, 85). This is because TNF-α is a potent stimulus for ROS production and triggers nitric oxide (NO) production by type 2 nitric oxide synthase at the infection site (85, 86). NO and ROS are critical for pathogen control. Previously it was shown that neutralization or deletion of TNF-α causes loss of control of intracellular pathogens in mice (87).

Figure 6:
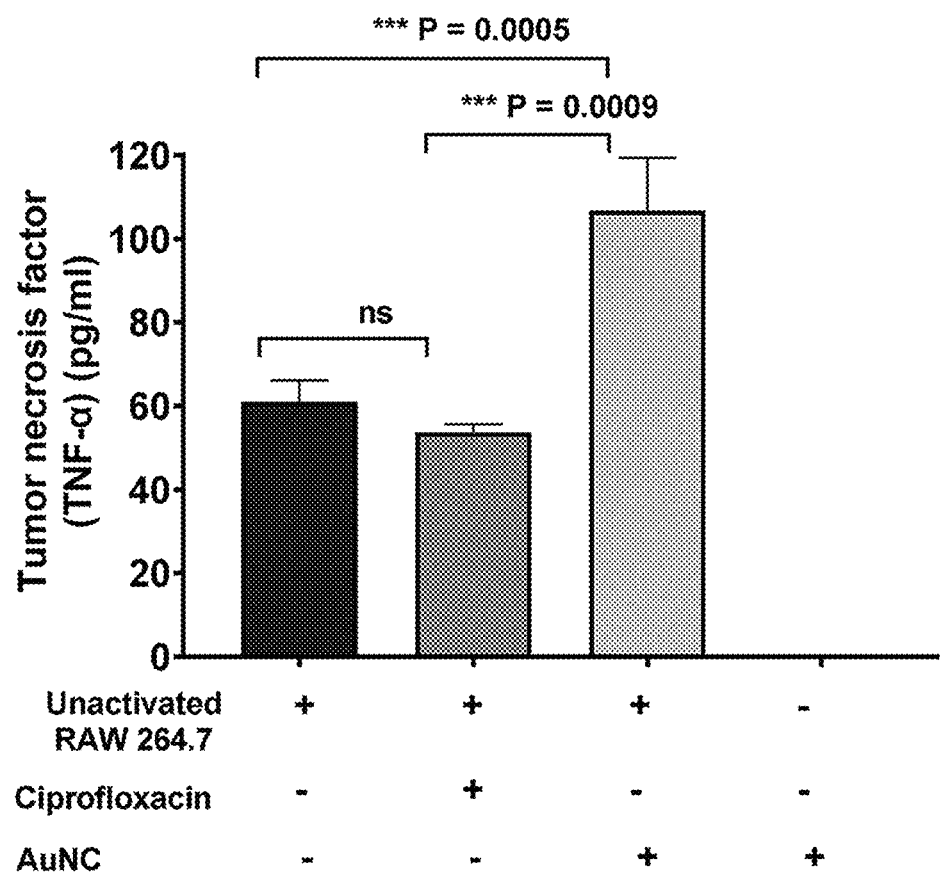
FIG. 6. AuNC stimulates the secretion of TNF-α. RAW 264.7 cells stimulated by AuNC had average TNF levels (106.79±12.7 pg/mL) that were nearly 2 times higher than ciprofloxacin (53.75±2 pg/mL). AuNC only was performed as a supplementary control, showing no interference with the assay. Data shown reflect mean±SD of three replicates.
Figure 7:
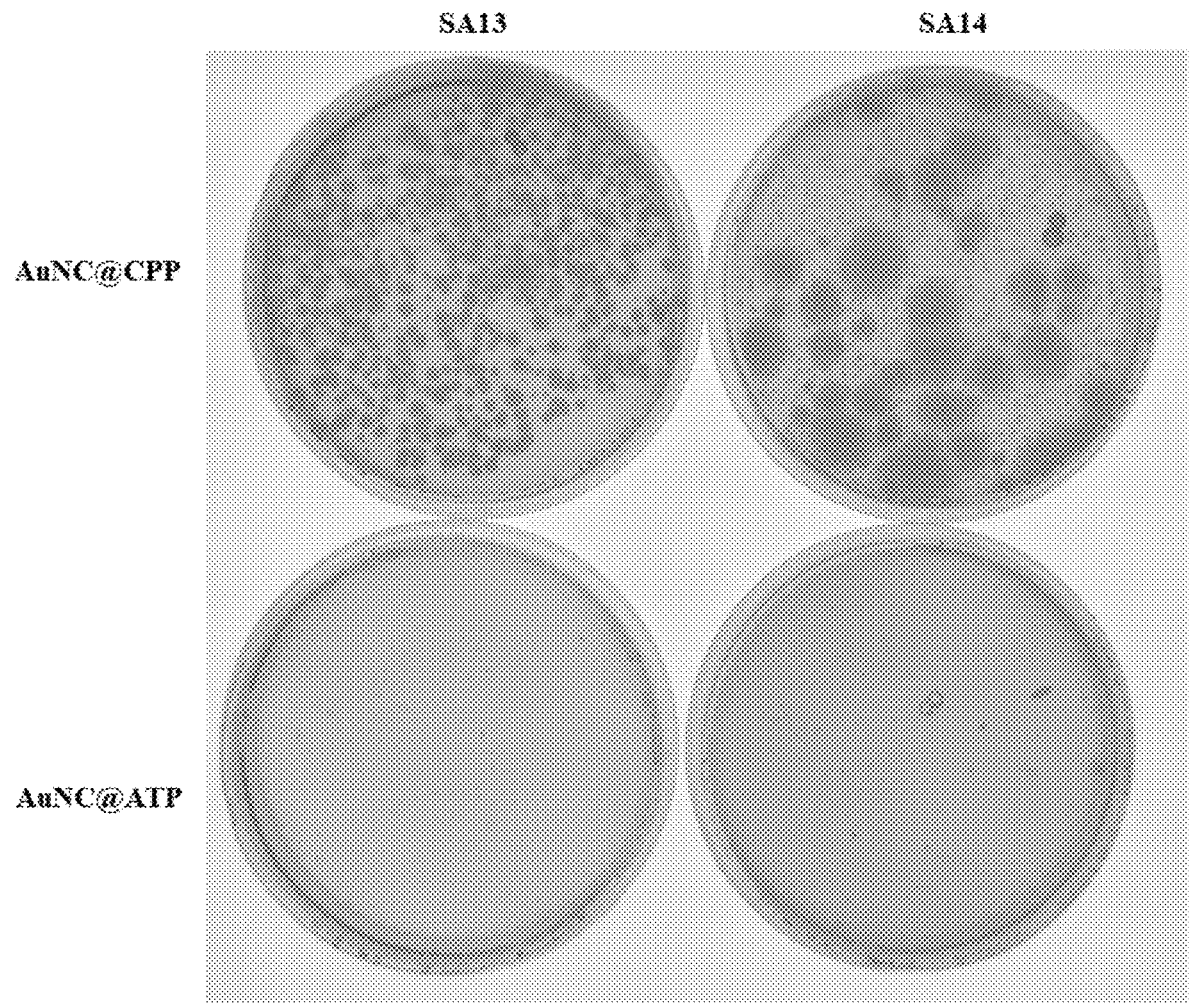
FIG. 7. Post ciprofloxacin exposure, 100% of the survived persister cells from otopathogenic *Staphylococcus aureus* (SA) are eradicate by AuNC@ATP. Left SA13 right SA14; top AuNC@CPP bottom AuNC@ATP.
Figure 8:
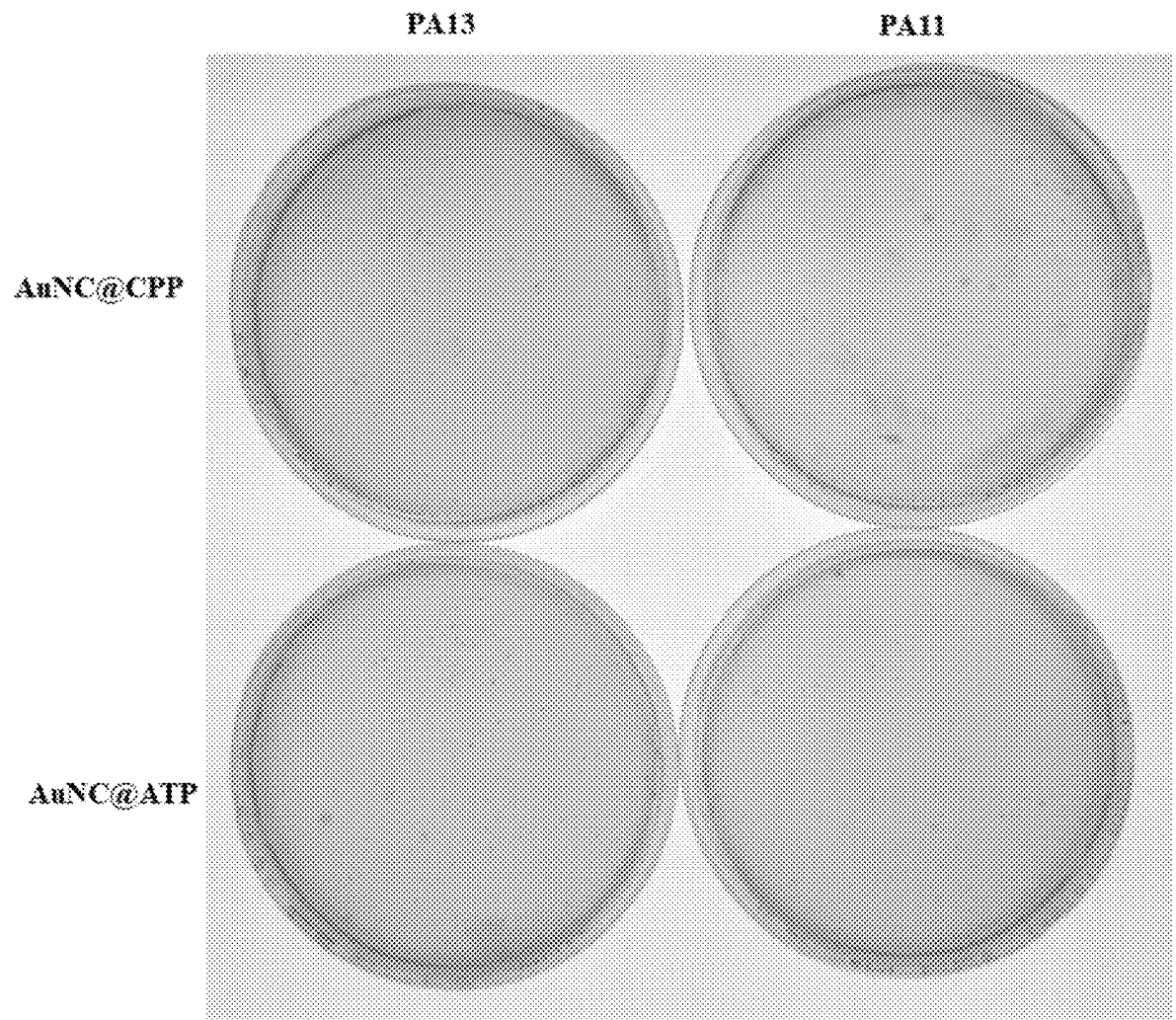
FIG. 8. Post ciprofloxacin exposure, 100% of the survived persister cells from otopathogenic *Pseudomonas aeruginosa* (PA) are eradicate by AuNC@ATP. Left PA13 right PA11; top AuNC@CPP bottom AuNC@ATP.

Our data show that stimulation of RAW 264.7 cells (i.e., monocyte/macrophage-like cells) with AuNC (i.e., 2 µg/mL of ciprofloxacin) led to significantly higher TNF-α accumulation than did the same concentrations of the parent drug ciprofloxacin (FIG. 6), supporting the potential contribution of TNF-α on the intracellular antimicrobial activity of the thiol antioxidant inhibition strategy. Furthermore, these data suggest that AuNC could potentially directly modulate the inflammatory response and direct macrophage differentiation towards an M1 phenotype, responsible for pathogen phagocytosis and killing, compared to M2 macrophages, involved in attenuating microbicidal activity (88, 89).

Assessing the Effect of AuNC Induced TNF-α Accumulation on NO Production by Macrophages When considering the possible mechanism by which TNF may help the intracellular antimicrobial activity of the thiol antioxidant inhibition strategy, it is essential to measure the NO levels produced by macrophages. We assess the NO levels in PA (XDR) infected macrophages incubated with various concentrations of AuNC. The negative control is the PA (XDR) infected macrophages without additional stimulation by AuNC. Intracellular NO levels are determined using the Griess reagent kit (ThermoFisher). The amount of NO is estimated using the standard nitrite curve from the kit.

Comparing the Antimicrobial Activity of AuNC in the Absence and Presence of an iNOS-Selective Inhibitor To assess whether the AuNC synergizes with nitric oxide synthase (iNOS), we evaluate the effect of L-N6-(1-iminoethyl)-lysine or L-NIL (iNOS-selective inhibitor) (87) on the antimicrobial activity of AuNC. RAW 264.7 cells are treated with L-NIL at a non-toxic concentration. After that, L-NIL-treated RAW 264.7 cells are infected with PA (XDR) and treated with AuNC, as illustrated in FIG. 5.

Assessing Whether AuNC-Induced TNF-α Accumulation Skews Monocytes Toward an M1 Phenotype In vivo, monocytes are recruited to and undergo terminal differentiation within the infection site, where they will encounter cytokines before interaction with PA. Differences in the polarization of macrophage phenotypes determine the efficacy in eradicating chronic PA. Pro-inflammatory (M1) macrophages are responsible for pathogen phagocytosis and killing, while M2 macrophages are involved in attenuating microbicidal activity (88, 89). In light of recent evidence on the benefits of promoting M1 macrophage, treatment with exogenous type III secretion protein PcrV directly drives macrophage differentiation toward an M1 phenotype, which accelerates macrophage-mediated PA clearance in a mouse model of PA catheter-associated biofilm infection. For that reason, the potential of AuNC to trigger macrophages differentiation toward an M1 phenotype must not be overlooked.

Example 7

CSOM Persister Cell Infection Model

There is a large unmet medical to develop treatments that can kill persister cells. Progress in this area has been hindered by the lack of a suitable animal model that replicates human persister cell infections. The persister cell problem is exemplified by the disease chronic suppurative otitis media (CSOM) afflicting 330 million worldwide. CSOM is a chronically discharging infected middle ear most frequently caused by *Pseudomonas aeruginosa* (PA), often resulting in permanent hearing loss and surgery.

We developed a novel persister cell model, optimized it to recapitulate the chronicity and microbial profile of human CSOM infections, validated it against standard microbiological benchmarks, and adopted it to include real-time in vivo tracking of PA (22). The key to the chronicity of CSOM in this model is the inoculation of the middle ear with the right dose of bacteria and with the correct phenotypes (i.e., larger amounts of persister cells). Through careful validation, we established that our model replicates the human CSOM condition in regards to 1) bacteriology, with the inclusion of PA persister cells, 2) chronicity, with infection recalcitrant to fluoroquinolone therapy lasting beyond six months, and 3) histology, with cochlear findings replicating temporal bone studies. By inoculating with chromosomally encoded luminescent PA01, we use an In Vivo Imaging System (IVIS) to track bacterial load quantitatively in real-time. Our model now allows the testing of novel therapeutic strategies for persistent PA persister cell infection.

While previous models studied acute infection, our novel model recapitulates critical features of human CSOM, including the presence of PA biofilms, induction of a persister cell phenotype in PA, and recalcitrance to fluoroquinolone therapy. As it replicates the human infection, we can directly assess the effects in vivo of potential therapeutics. Because we have designed our model with chromosomally encoded bioluminescence, we can track relapse and assess dose adjustments in real-time. This chromosomal bioluminescence also allows us to track bacteria intracellularly, which allows us to investigate this pathophysiology.

Figure 4A:
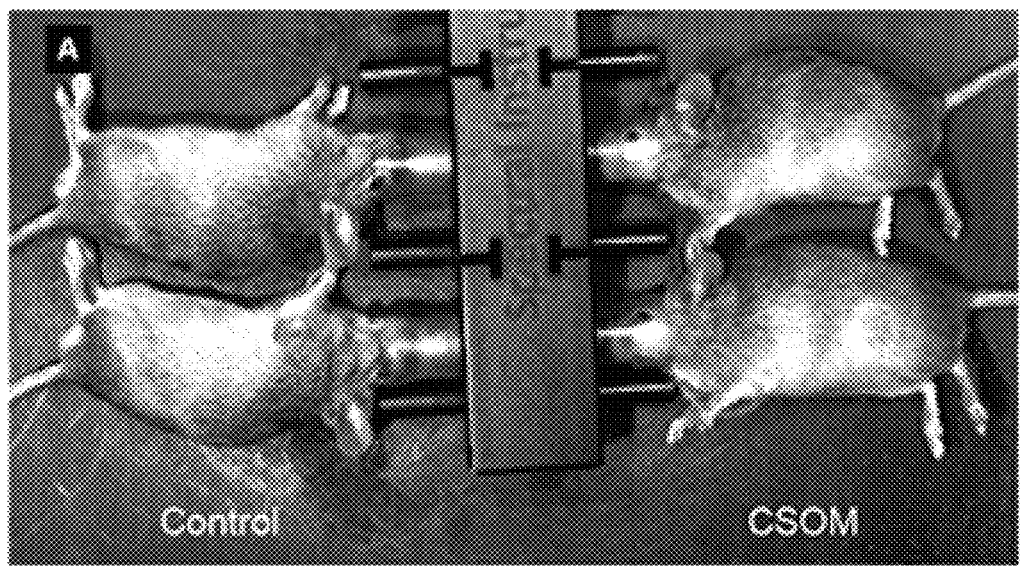
FIGS. 4A-4D. A Novel CSOM animal model. Real-time assessment of PA CSOM in vivo using IVIS (FIG. 4A). Photograph compare the luminescent signal from PAO1.lux (appears red) in PA inoculated mice (CSOM) and non-infected mice (control) day 12 after inoculation. Otomicroscope image showing copious exudate (FIG. 4B). Time dependent bacterial-bioluminescence during chronic middle ear infection in our CSOM model showing consistency over time (FIG. 4C). Combination (AuNC@CPP with ofloxacin) (24 µg of ofloxacin+296 µg of AuNC@CPP) has an antimicrobial activity superior to ofloxacin alone (24 µg). Combination induces up to a 10,000-fold reduction in bacterial burden compared to ofloxacin alone (FIG. 4D) D indicates that no middle ear effusion was able to be sampled due to technical constraints.
Figure 4B:
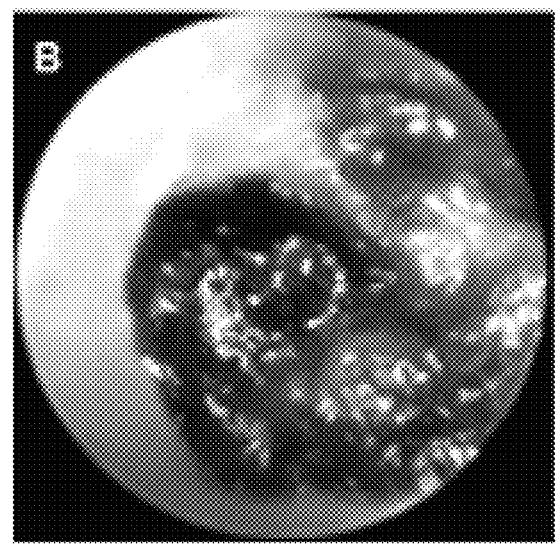
Figure 4C:
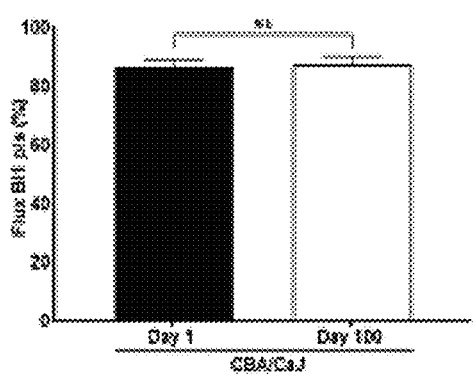
Figure 4D:
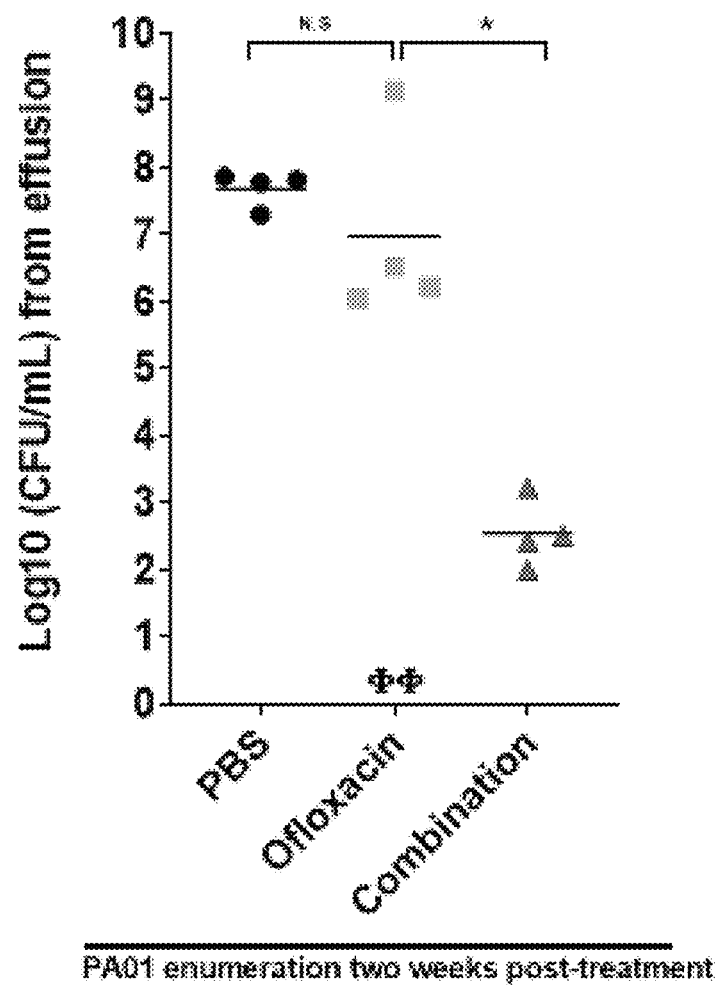

We use the validated animal model of PA persister cells in CSOM as a therapeutic platform to evaluate novel anti-persister compounds, such as AuNC. Real-time, quantifiable imaging of infections in our animal model for CSOM allows for monitoring the infection (55) (FIGS. 4A-4C). The relapse of infection is evaluated by tracking chromosomally encoded luminescent PA with the in vivo imaging system (IVIS). Using the platform, we previously demonstrated a paradigm shift (i.e., a novel thiol antioxidant inhibition strategy) in targeting bacteria in persister cells by co-administration of FLOXIN®Otic (ofloxacin) with an antibiotic adjuvant (anionic functionalized gold nanocluster, AuNC@CPP) that promotes hydroxyl radical formation. Comparison of the number of bacteria (CFU/mL) from middle ear effusion 14 days after the end of the following treatments: control (PBS), FLOXIN®Otic (24 μg of ofloxacin), and combination (24 μg of ofloxacin+296 μg of AuNC@CPP). There was no difference between the control and the ofloxacin. In contrast, the combination led to a 5 log reduction in bacteria 14 days after treatment. *$p \leq 0.05$ and not significant (N.S) (56) (FIG. 4D).

We confirm the efficacy of AuNC in our novel PA persister cell model using a method described previously (55, 56). In brief, first, we obtain stationary phase PA, and we treat them with ofloxacin for 4 hours to generate persister cells. Persister cells are then diluted with PBS to an optical density of 0.8. After creating a subtotal tympanic membrane perforation, we inoculate PA (5 μL, $1.6 \times 10^8$ CFU/mL) into the middle ear cavity, and the mice are allowed to rest with the ipsilateral ear up until recovery. We standardize our inoculum of persister cells by preparing PA fresh from stock, calculating the same CFU at each inoculum through CFU counting. Control mice receive equal volumes of sterile PBS. Disease progression is followed by capturing images with open emission using a LagoX In Vivo Imaging System (IVIS, Spectral Instruments Imaging, AZ USA). Luminescence is quantified with Aura software (Spectral Instruments Imaging, AZ USA). Cohorts receive twice-daily treatment for 14 days. We compare directly to Ciprofloxacin alone (24μ, the maximum available pharmaceutical topical dose), for which we expect to make a difference compared to the negative control. We use our older AuNC@CPP adjuvant with ciprofloxacin at the same level we previously demonstrated in vivo efficacy as a positive control. PBS serves as a negative control. The AuNC dose is 3000 μg/mL (i.e., 24 μg in 8 μL), to mimic the commercial formulation dose of topical ciprofloxacin.

Example 8

Subcellular Distribution of AuNC

We investigate the potential for direct persister cell killing by determining the subcellular distribution of AuNC. According to the standard protocol (64), we determine the intracellular localization of the AuNC in macrophages using transmission electron microscopy (TEM). TEM imaging is performed on the murine macrophage RAW 264.7 cell line exposed 24 h to AuNC (3 μg/mL). For TEM analysis, $1.5 \times 10^6$ cells are seeded per well, and after exposure to the AuNC, cells are fixed in freshly prepared 0.1 M glutaraldehyde solution. The cell pellets are then be postfixed in 2% osmium tetroxide. Ultrathin sections (approximately 60-80 nm) are cut and contrasted with uranyl acetate followed by lead citrate. Samples are examined using an FEI Tecnai Transmission Electron Microscope in the Stanford Nano Shared Facilities SNSF.

To understand the killing process, we need to know what exactly happens after AuNC uptake. Therefore, we test whether AuNC uptake results in ROS generation in the phagosomes and cytoplasm of uninfected and infected RAW 264.7 macrophages. To test the ROS generation in phagosomes, we conjugate AuNC with bovine serum albumin covalently coupled to dihydro-2',4,5,6,7,7'-hexafluorofluorescein (OxyBURST Green H2HFF BSA, ThermoFisher), allowing it to be a phagosomal ROS sensor. This strategy allows for the appropriate detection of phagosomal ROS regardless of the pH because H2HFF is a pH insensitive dye (65, 66). H2HFF-labeled AuNC will be used within 48 h of preparation due to autoxidation during storage. After incubation with AuNC (3 μg/mL) for 24 h, RAW 264.7 macrophages will be washed, and fluorescence will be recorded (excitation 480 nm, emission 530 nm) using flow cytometry. We then test whether AuNC uptake leads to enhanced cytosolic ROS production in uninfected and PA (XDR) infected macrophages using the fluorescent dyes 2' 7'-dichlorodihydrofluorescein diacetate (H2DCFH-DA). The dye is loaded within the uninfected and infected RAW 264.7 macrophages, then incubated with AuNC (3 μg/mL) for 24 h. RAW 264.7 macrophages will then be washed, and fluorescence is recorded (excitation 485 nm, emission 535 nm) using a plate reader (SpectraMax M2e).

Finally, we determine the concentration of AuNC in phagosomes. After 24 h exposure to the AuNC, phagosomes from RAW 267.4 mouse macrophages are isolated according to previous methods using sucrose ultracentrifugation in which the phagosomes float above cell debris and other organelles (67, 68). We perform the gold content analysis from phagosomes according to previous methods using inductively coupled plasma mass spectrometry (ICP-MS) (69) ROS activation has already been reported for gold nanoparticles, and ROS production by membrane protein assemblies called NADPH oxidase (NOX) is responsible for intracellular gold nanoparticle degradation inside the lysosome (70). Additionally, negatively charges nanoparticles are localized on the macrophage mitochondria (64). These findings suggest that negatively charged AuNC can interfere with the mitochondrial electron transport chain causing increases in cytosolic ROS level.

Example 9

Synthesis of Gold Nanoparticle Conjugated to Ciprofloxacin (AuNC@Cipro)

Freshly prepared aqueous solutions of $HAuCl_4$ (20 mM, 1 mL) and ciprofloxacin (60 mg) were mixed in water (17.4 mL). After that, an aqueous NaOH solution (1 M, 1.2 mL) was added to the mixture. A freshly prepared $NaBH_4$ solution (112 mM) was obtained by dissolving 43 mg of $NaBH_4$ in 2 mL of NaOH solution (1 M), followed by the addition of 8 mL of ultrapure water. After that, 0.1 mL of $NaBH_4$ solution was added to the solution, and the AuNC@Cipro was collected after 24 h. After synthesis, the solutions were dialyzed (dialysis membrane, MWCO=3000) for 2 days against Milli-Q water, which was changed every 8 h to remove the unconjugated ciprofloxacin. The resulting AuNC@Cipro were lyophilized and dried entirely before further use.

Example 10

Synthesis of Gold Nanoparticle Conjugated to Adenosine Triphosphate (AuNC@ATP)

Freshly prepared aqueous solutions of $HAuCl_4$ (20 mM, 1 mL) and adenosine triphosphate (100 mg) were mixed in water (17.4 mL). After that, an aqueous NaOH solution (1 M, 1.2 mL) was added to the mixture. A freshly prepared NaBH4 solution (112 mM) was obtained by dissolving 43 mg of $NaBH_4$ in 2 mL of NaOH solution (1 M), followed by the addition of 8 mL of ultrapure water. After that, 0.1 mL of $NaBH_4$ solution was added to the solution, and the AuNC@Cipro was collected after 24 h. After synthesis, the solutions were dialyzed (dialysis membrane, MWCO=3000) for 2 days against Milli-Q water, which was changed every 8 h to remove the unconjugated ciprofloxacin. The resulting AuNC@Cipro were lyophilized and dried entirely before further use.

Example 11

Synthesis of Polydopamine Nanoparticle Conjugated to Ciprofloxacin (PDA@Cipro)

Briefly, 1 mg/mL of dopamine hydrochloride and ciprofloxacin (15 mg) were dissolved in 10 mM at pH 10.5 and allowed to polymerize at room temperature (25° C.) over time. The synthesized PDA@Cipro were then washed with Tris buffer (pH 10.5) by repeated centrifugation at 16 100 g for 4 min and stored for use. The concentration of PDA@Cipro is determined from the absorbance at 808 nm ($E_{PDA}=7.3\times10^8$ $M^{-1}$ $cm^{-1}$).

REFERENCES

1. Buyck J M, Tulkens Pm Fau-Van Bambeke F, Van Bambeke F. Pharmacodynamic evaluation of the intracellular activity of antibiotics towards *Pseudomonas aeruginosa* PAO1 in a model of THP-1 human monocytes (1098-6596 (Electronic)).
2. Davies D. Understanding biofilm resistance to antibacterial agents. Nature reviews Drug discovery. 2003; 2(2): 114-22.
3. Koo H, Allan R N, Howlin R P, Stoodley P, Hall-Stoodley L. Targeting microbial biofilms: current and prospective therapeutic strategies. Nature Reviews Microbiology. 2017; 15(12):740.
4. Wolcott R, Rhoads D, Bennett M, Wolcott B, Gogokhia L, Costerton J, Dowd S. Chronic wounds and the medical biofilm paradigm. Journal of wound care. 2010; 19(2): 45-53.
5. Sansgiry S S, Joish V N, Boklage S, Goyal R K, Chopra P, Sethi S. Economic burden of *Pseudomonas aeruginosa* infection in patients with cystic fibrosis. J Med Econ. 2012; 15(2):219-24. Epub 2011 Nov. 17 06:00. PubMed PMID: 22084956.
6. Malic S, Hill K E, Hayes A, Percival S L, Thomas D W, Williams D W. Detection and identification of specific bacteria in wound biofilms using peptide nucleic acid fluorescent in situ hybridization (PNA FISH) (1350-0872 (Print)).
7. Dowd S E, Sun Y Fau-Secor P R, Secor Pr Fau-Rhoads D D, Rhoads Dd Fau Wolcott B M, Wolcott Bm Fau-James G A, James Ga Fau-Wolcott R D, Wolcott R D. Survey of bacterial diversity in chronic wounds using pyrosequencing, DGGE, and full ribosome shotgun sequencing (1471-2180 (Electronic)).
8. Kirketerp-Møller K, Jensen P O Fau-Fazli M, Fazli M Fau-Madsen K G, Madsen Kg Fau-Pedersen J, Pedersen J Fau-Moser C, Moser C Fau-Tolker-Nielsen T, Tolker-Nielsen T Fau-Hoiby N, Hoiby N Fau-Givskov M, Givskov M Fau-Bjarnsholt T, Bjarnsholt T. Distribution, organization, and ecology of bacteria in chronic wounds (1098-660X (Electronic)).
9. Tredget E E, Shankowsky Ha Fau-Rennie R, Rennie R Fau-Burrell R E, Burrell Re Fau-Logsetty S, Logsetty S. *Pseudomonas* infections in the thermally injured patient (0305-4179 (Print)).
10. Lipsky B A, Berendt Ar Fau-Deery H G, Deery Hg Fau-Embil J M, Embil Jm Fau-Joseph W S, Joseph Ws Fau-Karchmer A W, Karchmer Aw Fau-LeFrock J L, LeFrock J l Fau-Lew D P, Lew Dp Fau-Mader J T, Mader Jt Fau-Norden C, Norden C Fau-Tan J S, Tan J S. Diagnosis and treatment of diabetic foot infections (1537-6591 (Electronic)).
11. Percival S L, Suleman L, Vuotto C, Donelli G. Healthcare-associated infections, medical devices and biofilms: risk, tolerance and control (1473-5644 (Electronic)).
12. Monasta L, Ronfani L, Marchetti F, Montico M, Vecchi Brumatti L, Bavcar A, Grasso D, Barbiero C, Tamburlini G. Burden of disease caused by otitis media: systematic review and global estimates. PLoS One. 2012; 7(4): e36226. doi: 10.1371/journal.pone.0036226. PubMed PMID: 22558393; PMCID: PMC3340347.
13. Acuin J. Chronic Suppurative Otitis Media: Burden of Illness and Management Options. Switzerland: World Health Organization; 2004.
14. Bakaletz L O. Bacterial biofilms in otitis media: evidence and relevance. The Pediatric infectious disease journal. 2007; 26(10):S17-S9.

15. Lewis K. Persister cells and the paradox of chronic infections. Microbe. 2010; 5(10):429-37.
16. Conlon B P, Rowe S E, Gandt A B, Nuxoll A S, Donegan N P, Zalis E A, Clair G, Adkins J N, Cheung A L, Lewis K. Persister formation in *Staphylococcus aureus* is associated with ATP depletion. Nat Microbiol. 2016; 1(16051):16051. Epub 2016 Aug. 31 06:00. PubMed PMID: 27572649.
17. Harms A, Maisonneuve E, Gerdes K. Mechanisms of bacterial persistence during stress and antibiotic exposure. LID—aaf4268 [pii] (1095-9203 (Electronic)).
18. Mitchell P. Chemiosmotic coupling in oxidative and photosynthetic phosphorylation. 1966 (0006-3002 (Print)).
19. Conlon B P, Rowe S E, Gandt A B, Nuxoll A S, Donegan N P, Zalis E A, Clair G, Adkins J N, Cheung A L, Lewis K. Persister formation in *Staphylococcus aureus* is associated with ATP depletion. LID—16051 [pii] (2058-5276 (Electronic)).
20. Peyrusson F, Varet H A-O, Nguyen T K, Legendre R A-O, Sismeiro O, Coppee J Y, Wolz C A-O, Tenson T, Van Bambeke F A-O. Intracellular *Staphylococcus aureus* persisters upon antibiotic exposure (2041-1723 (Electronic)).
21. Rowe S E, Wagner N J, Li L, Beam J E, Wilkinson A D, Radlinski L C, Zhang Q, Miao E A-O, Conlon B A-O. Reactive oxygen species induce antibiotic tolerance during systemic *Staphylococcus aureus* infection (2058-5276 (Electronic)).
22. Murima P, McKinney J D, Pethe K. Targeting bacterial central metabolism for drug development (1879-1301 (Electronic)).
23. Gutierrez A, Jain S, Bhargava P, Hamblin M, Lobritz M A, Collins J J. Understanding and Sensitizing Density-Dependent Persistence to Quinolone Antibiotics (1097-4164 (Electronic)).
24. Yan J, Bassler B L. Surviving as a Community: Antibiotic Tolerance and Persistence in Bacterial Biofilms. Cell Host Microbe. 2019; 26(1):15-21. Epub 2019 Jul. 12 06:00. PubMed PMID: 31295420.
25. Huang H W, Charron N E. Understanding membrane-active antimicrobial peptides (1469-8994 (Electronic)).
26. Zhang N, Ma S. Recent development of membrane-active molecules as antibacterial agents (1768-3254 (Electronic)).
27. Hurdle J G, O'Neill Aj Fau-Chopra I, Chopra I Fau-Lee R E, Lee R E. Targeting bacterial membrane function: an underexploited mechanism for treating persistent infections (1740-1534 (Electronic)).
28. Silverman J A, Mortin Li Fau-Vanpraagh A D G, Vanpraagh Ad Fau-Li T, Li T Fau-Alder J, Alder J. Inhibition of daptomycin by pulmonary surfactant: in vitro modeling and clinical impact (0022-1899 (Print)).
29. Van Bambeke F, Saffran J Fau-Mingeot-Leclercq M-P, Mingeot-Leclercq Mp Fau-Tulkens P M, Tulkens P M. Mixed-lipid storage disorder induced in macrophages and fibroblasts by oritavancin (LY333328), a new glycopeptide antibiotic with exceptional cellular accumulation (0066-4804 (Print)).
30. Soo V W, Kwan B W, Quezada H, Castillo-Juarez I, Perez-Eretza B, Garcia-Contreras S J, Martinez-Vazquez M, Wood T K, Garcia-Contreras R. Repurposing of Anticancer Drugs for the Treatment of Bacterial Infections (1873-4294 (Electronic)).
31. Chowdhury N, Wood T L, Martinez-Vazquez M, Garcia-Contreras R, Wood T K. DNA-crosslinker cisplatin eradicates bacterial persister cells (1097-0290 (Electronic)).
32. Oppezzo O J, Forte Giacobone A F. Lethal Effect of Photodynamic Treatment on Persister Bacteria (1751-1097 (Electronic)).
33. *Sultana* ST, Call D R, Beyenal H. Eradication of *Pseudomonas aeruginosa* biofilms and persister cells using an electrochemical scaffold and enhanced antibiotic susceptibility (2055-5008 (Print)).
34. Brynildsen M P, Winkler Ja Fau-Spina C S, Spina Cs Fau-MacDonald I C, MacDonald Ic Fau-Collins J J, Collins J J. Potentiating antibacterial activity by predictably enhancing endogenous microbial ROS production (1546-1696 (Electronic)).
35. Hong Y A-O, Zeng J, Wang X, Drlica K, Zhao X A-O. Post-stress bacterial cell death mediated by reactive oxygen species (1091-6490 (Electronic)).
36. Kohanski M A, Dwyer Dj Fau-Hayete B, Hayete B Fau-Lawrence C A, Lawrence Ca Fau-Collins J J, Collins J J. A common mechanism of cellular death induced by bactericidal antibiotics (0092-8674 (Print)).
37. Fisher R A, Gollan B, Helaine S. Persistent bacterial infections and persister cells (1740-1534 (Electronic)).
38. Brauner A, Fridman O, Gefen O, Balaban N Q. Distinguishing between resistance, tolerance and persistence to antibiotic treatment (1740-1534 (Electronic)).
39. Smirnova G V, Oktyabrsky O N. Glutathione in bacteria (0006-2979 (Print)).
40. Zhang Y, Duan K. Glutathione exhibits antibacterial activity and increases tetracycline efficacy against *Pseudomonas aeruginosa* (1006-9305 (Print)).
41. Michie K L, Dees J L, Fleming D A-OX, Moustafa D A, Goldberg J B, Rumbaugh K P, Whiteley M. Role of *Pseudomonas aeruginosa* Glutathione Biosynthesis in Lung and Soft Tissue Infection. LID—10.1128/IAI.00116-20 [doi] LID—e00116-20(1098-5522 (Electronic)).
42. Van Laar T A, Esani S, Birges T J, Hazen B, Thomas J M, Rawat M. *Pseudomonas aeruginosa* gshA Mutant Is Defective in Biofilm Formation, Swarming, and Pyocyanin Production. LID—10.1128/mSphere.00155-18 [doi] LID—e00155-18(2379-5042 (Electronic)).
43. Wongsaroj L, Saninjuk K, Romsang A A-O, Duang-Nkern J, Trinachartvanit W, Vattanaviboon P, Mongkolsuk S A-O. *Pseudomonas aeruginosa* glutathione biosynthesis genes play multiple roles in stress protection, bacterial virulence and biofilm formation (1932-6203 (Electronic)).
44. Chen S J, Chang H T. Nile red-adsorbed gold nanoparticles for selective determination of thiols based on energy transfer and aggregation (0003-2700 (Print)).
45. Häkkinen H. The gold-sulfur interface at the nanoscale (1755-4349 (Electronic)).
46. Zheng M, Aslund F Fau-Storz G, Storz G. Activation of the OxyR transcription factor by reversible disulfide bond formation (0036-8075 (Print)).
47. Imlay J A. The molecular mechanisms and physiological consequences of oxidative stress: lessons from a model bacterium (1740-1534 (Electronic)).
48. Dwyer D J, Belenky P A, Yang J A-O, MacDonald I C, Martell J D, Takahashi N, Chan C T, Lobritz M A, Braff D, Schwarz E G, Ye J D, Pati M, Vercruysse M, Ralifo P S, Allison K R, Khalil A S, Ting A Y, Walker G C, Collins J J. Antibiotics induce redox-related physiological alterations as part of their lethality (1091-6490 (Electronic)).
49. Schuller-*Levis* GB, Sturman J A. "Activation" of alveolar leukocytes isolated from cats fed taurine-free diets (0065-2598 (Print)).

50. Voloboueva L A, Liu J Fau-Suh J H, Suh Jh Fau-Ames B N, Ames Bn Fau-Miller S S, Miller S S. (R)-alpha-lipoic acid protects retinal pigment epithelial cells from oxidative damage (0146-0404 (Print)).
51. Seaver L C, Imlay J A. Hydrogen peroxide fluxes and compartmentalization inside growing *Escherichia coli* (0021-9193 (Print)).
52. Jang S, Imlay J A. Micromolar intracellular hydrogen peroxide disrupts metabolism by damaging iron-sulfur enzymes (0021-9258 (Print)).
53. Kawano A, Yamasaki R, Sakakura T, Takatsuji Y, Haruyama T, Yoshioka Y, Ariyoshi W. Reactive Oxygen Species Penetrate Persister Cell Membranes of *Escherichia coli* for Effective Cell Killing (2235-2988 (Electronic)).
54. Liu Z Fau-Liu J, Liu J A-O, Mateti S Fau-Zhang C, Zhang C, Zhang Y, Chen L Fau-Wang J, Wang J Fau-Wang H, Wang H Fau-Doeven E H, Doeven Eh Fau-Francis P S, Francis Ps Auid-Orcid:—Fau-Barrow C J, Barrow Cj Fau-Du A, Du A A-O, Chen Y Auid-Orcid:—Fau-Yang W, Yang W A-O. Boron Radicals Identified as the Source of the Unexpected Catalysis by Boron Nitride Nanosheets (1936-086X (Electronic)).
55. Khomtchouk K M, Kouhi A, Xia A, Bekale L A, Massa S M, Sweere J M, Pletzer D, Hancock R E, Bollyky P L, Santa Maria P L. A novel mouse model of chronic suppurative otitis media and its use in preclinical antibiotic evaluation. Science Advances. 2020; 6(33):eabc1828. doi: 10.1126/sciadv.abc1828.
56. Laurent B, Peter L S M, Zhixin C, Xiaohua C, Anping X, Brian B, Jessica T, Jing C. Research Square. 2021. doi: 10.21203/rs.3.rs-127769/v1.
57. Cossarizza A, Ferraresi R Fau-Troiano L, Troiano L Fau-Roat E, Roat E Fau-Gibellini L, Gibellini L Fau-Bertoncelli L, Bertoncelli L Fau-Nasi M, Nasi M Fau-Pinti M, Pinti M. Simultaneous analysis of reactive oxygen species and reduced glutathione content in living cells by polychromatic flow cytometry (1750-2799 (Electronic)).
58. Hedley D W, Chow S. Evaluation of methods for measuring cellular glutathione content using flow cytometry (0196-4763 (Print)).
59. Tao K, Makino K Fau-Yonei S, Yonei S Fau-Nakata A, Nakata A Fau-Shinagawa H, Shinagawa H. Purification and characterization of the *Escherichia coli* OxyR protein, the positive regulator for a hydrogen peroxide-inducible regulon (0021-924X (Print)).
60. Huang J, Canadien V Fau-Lam G Y, Lam Gy Fau-Steinberg B E, Steinberg Be Fau-Dinauer M C, Dinauer Mc Fau-Magalhaes M A O, Magalhaes Ma Fau-Glogauer M, Glogauer M Fau-Grinstein S, Grinstein S Fau-Brumell J H, Brumell J H. Activation of antibacterial autophagy by NADPH oxidases (1091-6490 (Electronic)).
61. Lam G Y, Huang J Fau-Brumell J H, Brumell J H. The many roles of NOX2 NADPH oxidase-derived ROS in immunity (1863-2300 (Electronic)).
62. Garai P, Berry L, Moussouni M, Bleves S A-O, Blanc-Potard A A-O. Killing from the inside: Intracellular role of T355 in the fate of *Pseudomonas aeruginosa* within macrophages revealed by mgtC and oprF mutants (1553-7374 (Electronic)).
63. Cavinato L, Genise E, Luly F R, Di Domenico E G, Del Porto P, Ascenzioni F. Escaping the Phagocytic Oxidative Burst: The Role of SODB in the Survival of *Pseudomonas aeruginosa* Within Macrophages (1664-302X (Print)).
64. Srijampa S, Buddhisa S, Ngernpimai S, Leelayuwat C, Proungvitaya S, Chompoosor A, Tippayawat P A-O. Influence of Gold Nanoparticles with Different Surface Charges on Localization and Monocyte Behavior (1520-4812 (Electronic)).
65. VanderVen B C, Yates Rm Fau-Russell D G, Russell D G. Intraphagosomal measurement of the magnitude and duration of the oxidative burst (1600-0854 (Electronic)).
66. Chen C S. Phorbol ester induces elevated oxidative activity and alkalization in a subset of lysosomes (1471-2121 (Electronic)).
67. Hartlova A, Peltier J, Bilkei-Gorzo O, Trost M. Isolation and Western Blotting of Latex-Bead Phagosomes to Track Phagosome Maturation (1940-6029 (Electronic)).
68. Lührmann A, Haas A. A method to purify bacteria-containing phagosomes from infected macrophages (1381-5741 (Print)).
69. Carlander U, Midander K, Hedberg Y S, Johanson G, Bottai M, Karlsson H L. Macrophage-Assisted Dissolution of Gold Nanoparticles. ACS Applied Bio Materials. 2019; 2(3):1006-16. doi: 10.1021/acsabm.8b00537.
70. Balfourier A, Luciani N, Wang G, Lelong G, Ersen O, Khelfa A, Alloyeau D, Gazeau F A-O, Carn F A-O. Unexpected intracellular biodegradation and recrystallization of gold nanoparticles (1091-6490 (Electronic)).
71. Balce D R, Yates R M. Fluorometric Approaches to Measuring Reductive and Oxidative Events in Phagosomes (1940-6029 (Electronic)).
72. Tannich F, Tlili A, Pintard C, Chniguir A, Eto B, Dang P M, Souilem O, El-Benna J A-OX. Activation of the phagocyte NADPH oxidase/NOX2 and myeloperoxidase in the mouse brain during pilocarpine-induced temporal lobe epilepsy and inhibition by ketamine (1568-5608 (Electronic)).
73. Chen T L, Chang Cc Fau-Lin Y-L, Lin Y I Fau-Ueng Y-F, Ueng Yf Fau-Chen R-M, Chen R M. Signal-transducing mechanisms of ketamine-caused inhibition of interleukin-1 beta gene expression in lipopolysaccharide-stimulated murine macrophage-like Raw 264.7 cells (1096-0333 (Electronic)).
74. Kinchen J M, Ravichandran K S. Phagosome maturation: going through the acid test (1471-0080 (Electronic)).
75. Chow C W, Downey Gp Fau-Grinstein S, Grinstein S. Measurements of phagocytosis and phagosomal maturation (1934-2616 (Electronic)).
76. Dayam R M, Botelho R J. Quantitative Immunofluorescence to Study Phagosome Maturation (1940-6029 (Electronic)).
77. Garai P, Berry L, Moussouni M, Bleves S, Blanc-Potard A B. Killing from the inside: Intracellular role of T3SS in the fate of *Pseudomonas aeruginosa* within macrophages revealed by mgtC and oprF mutants. PLoS Pathog. 2019; 15(6):e1007812. Epub 2019 Jun. 21 06:00. PubMed PMID: 31220187.
78. Joshi G N, Gilberti R M, Knecht D A. Single Cell Analysis of Phagocytosis, Phagosome Maturation, Phagolysosomal Leakage, and Cell Death Following Exposure of Macrophages to Silica Particles (1940-6029 (Electronic)).
79. Ha S W, Weitzmann Mn Fau-Beck G R, Jr., Beck G R, Jr. Bioactive silica nanoparticles promote osteoblast differentiation through stimulation of autophagy and direct association with LC3 and p62 (1936-086X (Electronic)).
80. Li W, Li S, Li Y, Lin X, Hu Y, Meng T, Wu B, He R, Feng D. Immunofluorescence Staining Protocols for Major Autophagy Proteins Including L C3, P62, and ULK1 in Mammalian Cells in Response to Normoxia and Hypoxia (1940-6029 (Electronic)).

81. Xu Y, Jagannath C Fau-Liu X-D, Liu Xd Fau-Sharafkhaneh A, Sharafkhaneh A Fau-Kolodziejska K E, Kolodziejska Ke Fau-Eissa N T, Eissa N T. Toll-like receptor 4 is a sensor for autophagy associated with innate immunity (1074-7613 (Print)).
82. Parameswaran N, Patial S. Tumor necrosis factor-α signaling in macrophages (1045-4403 (Print)).
83. Witsell A L, Schook L B. Tumor necrosis factor alpha is an autocrine growth regulator during macrophage differentiation (0027-8424 (Print)).
84. Bogdan C. Nitric oxide synthase in innate and adaptive immunity: an update (1471-4981 (Electronic)).
85. Yazdanpanah B, Wiegmann K Fau-Tchikov V, Tchikov V Fau-Krut O, Krut O Fau-Pongratz C, Pongratz C Fau-Schramm M, Schramm M Fau-Kleinridders A, Kleinridders A Fau-Wunderlich T, Wunderlich T Fau-Kashkar H, Kashkar H Fau-Utermohlen O, Utermohlen O Fau-Bruning J C, Bruning Jc Fau-Schutze S, Schutze S Fau-Kronke M, Kronke M. Riboflavin kinase couples TNF receptor 1 to NADPH oxidase (1476-4687 (Electronic)).
86. Schleicher U, Paduch K, Debus A, Obermeyer S, Konig T, Kling J C, Ribechini E, Dudziak D, Mougiakakos D, Murray P J, Ostuni R, Korner H, Bogdan C. TNF-Mediated Restriction of Arginase 1 Expression in Myeloid Cells Triggers Type 2 NO Synthase Activity at the Site of Infection (2211-1247 (Electronic)).
87. Zganiacz A, Santosuosso M Fau-Wang J, Wang J Fau-Yang T, Yang T Fau Chen L, Chen L Fau-Anzulovic M, Anzulovic M Fau-Alexander S, Alexander S Fau-Gicquel B, Gicquel B Fau-Wan Y, Wan Y Fau-Bramson J, Bramson J Fau-Inman M, Inman M Fau-Xing Z, Xing Z. TNF-alpha is a critical negative regulator of type 1 immune activation during intracellular bacterial infection (0021-9738 (Print)).
88. Shapouri-Moghaddam A, Mohammadian S, Vazini H, Taghadosi M, Esmaeili S A, Mardani F, Seifi B, Mohammadi A, Afshari J T, Sahebkar A A-O. Macrophage plasticity, polarization, and function in health and disease (1097-4652 (Electronic)).
89. Panagi I, Jennings E, Zeng J, Gunster R A, Stones C D, Mak H, Jin E, Stapels D A C, Subari N Z, Pham T H M, Brewer S M, Ong S Y Q, Monack D M, Helaine S, Thurston T L M. *Salmonella* Effector SteE Converts the Mammalian Serine/Threonine Kinase GSK3 into a Tyrosine Kinase to Direct Macrophage Polarization (1934-6069 (Electronic)).
90. Davis M J, Tsang Tm Fau-Qiu Y, Qiu Y Fau-Dayrit J K, Dayrit Jk Fau-Freij J B, Freij Jb Fau-Huffnagle G B, Huffnagle Gb Fau-Olszewski M A, Olszewski M A. Macrophage M1/M2 polarization dynamically adapts to changes in cytokine microenvironments in *Cryptococcus neoformans* infection (2150-7511 (Electronic)).
91. Taciak B, Biafasek M, Braniewska A, Sas Z, Sawicka P, Kiraga L, Rygiel T, Król MA-O. Evaluation of phenotypic and functional stability of RAW 264.7 cell line through serial passages (1932-6203 (Electronic)).
92. Orecchioni M, Ghosheh Y, Pramod A B, Ley K. Macrophage Polarization: Different Gene Signatures in M1(LPS+) vs. Classically and M2(LPS−) vs. Alternatively Activated Macrophages (1664-3224 (Electronic)).
93. Celik M, Labuz D, Keye J, Glauben R, Machelska H. IL-4 induces M2 macrophages to produce sustained analgesia via opioids. LID—133093 [pii] LID—10.1172/jci.insight.133093 [doi] LID—e133093 (2379-3708 (Electronic)).

What is claimed is:

1. A method of treating an infection in a subject, the method comprising administering to the subject a therapeutically effective amount of a composition comprising a nanoparticle comprising a thiol-binding metallic core conjugated to a fluoroquinolone antibiotic, wherein the diameter of the nanoparticle is in a range from about 1 nm to about 5 nm.

2. The method of claim 1, further comprising administering a therapeutically effective amount of at least one antibiotic in combination with the composition.

3. The method of claim 1, wherein the subject has a chronic infection.

4. The method of claim 3, wherein the infection is an ear infection, a cutaneous infection, a lung infection, a catheter-associated urinary tract infection, or a gastrointestinal infection.

5. The method of claim 1, wherein the subject has chronic suppurative otitis media (CSOM), cystic fibrosis, or tuberculosis.

6. The method of claim 1, wherein the composition is administered intravenously, subcutaneously, by inhalation, or topically.

7. The method of claim 1, wherein the infection is an ear infection, and the composition is administered locally into the ear canal.

8. A method of eradicating bacteria in a biofilm or dormant bacteria comprising persister cells, the method comprising contacting the biofilm or the dormant bacteria with an effective amount of a nanoparticle comprising a thiol-binding metallic core conjugated to a fluoroquinolone antibiotic, wherein the diameter of the nanoparticle is in a range from about 1 nm to about 5 nm.

9. The method of claim 8, wherein the biofilm is on a medical device, a personal hygiene article, toiletry, cosmetic, disinfectant, cleaning solution, or in a water treatment or distribution system.

10. The method of claim 1, wherein the fluoroquinolone antibiotic is selected from the group consisting of ciprofloxacin, ofloxacin, moxifloxacin, gemifloxacin, levofloxacin, and finafloxacin.

11. The method of claim 10, wherein the thiol-binding metallic core is conjugated to 47 ciprofloxacin molecules.

12. The method of claim 10, wherein the ciprofloxacin is conjugated to the thiol-binding metallic core through a bond between an amino group of the ciprofloxacin and a metal atom of the metallic core.

13. The method of claim 1, wherein the thiol-binding metallic core comprises one or more of gold, silver, nickel, copper, aluminum, or cobalt, or an oxide, carbide, nitride, or alloy thereof.

14. The method of claim 1, wherein the metallic core has a diameter of about 4 nm.

15. The method of claim 1, wherein the nanoparticle further comprises a cell penetrating peptide, an anionic moiety, or a polyethylene glycol (PEG) polymer attached to the outer surface of the nanoparticle.

16. The method of claim 15, wherein the anionic moiety comprises a carboxylate functional group, a phosphate functional group, or a sulfate functional group.

17. The method of claim 15, wherein the PEG polymer is functionalized with the anionic moiety.

18. The method of claim 1, wherein the nanoparticle further comprises an antimicrobial agent having bactericidal activity against persister cells or bacteria residing in biofilms, wherein the antimicrobial agent is attached to the outer surface of the nanoparticle.

19. The method of claim 18, wherein the antimicrobial agent is a D-carbohydrate, a D-amino acid, or a nucleic acid comprising a CrcZ RNA sequence or a CrcZ A-rich motif sequence.

20. The method of claim 1, wherein the nanoparticle further comprises a nucleotide, wherein the nucleotide is conjugated to the thiol-binding metallic core.

21. The method of claim 20, wherein the nucleotide is adenosine triphosphate (ATP), adenosine monophosphate (AMP), adenosine diphosphate (ADP), or a phosphorothioate analog, deoxyribonucleotide analog, a 7-deaza purine nucleotide analog, or a phosphomethylphosphonic acid adenylate ester thereof.

22. The method of claim 1, wherein the composition further comprises a pharmaceutically acceptable excipient or carrier.

23. A method of eradicating intra-macrophage bacteria in a subject, the method comprising administering to the subject a therapeutically effective of a nanoparticle comprising a thiol-binding metallic core conjugated to a fluoroquinolone antibiotic, wherein the diameter of the nanoparticle is in a range from about 1 nm to about 5 nm.

\* \* \* \* \*